(12) United States Patent
Rao et al.

(10) Patent No.: US 12,037,597 B2
(45) Date of Patent: *Jul. 16, 2024

(54) PROKARYOTIC-EUKARYOTIC HYBRID VIRAL VECTOR FOR DELIVERY OF LARGE CARGOS OF GENES AND PROTEINS INTO HUMAN CELLS

(71) Applicant: The Catholic University of America, Washington, DC (US)

(72) Inventors: Venigalla B. Rao, Silver Spring, MD (US); Jingen Zhu, Washington, DC (US)

(73) Assignee: The Catholic University of America, Washington, DC (US)

( * ) Notice: Subject to any disclaimer, the term of this patent is extended or adjusted under 35 U.S.C. 154(b) by 443 days.

This patent is subject to a terminal disclaimer.

(21) Appl. No.: 17/488,542

(22) Filed: Sep. 29, 2021

(65) Prior Publication Data
US 2022/0010335 A1 Jan. 13, 2022

Related U.S. Application Data

(62) Division of application No. 16/990,289, filed on Aug. 11, 2020, now Pat. No. 11,155,835.

(60) Provisional application No. 62/888,576, filed on Aug. 19, 2019.

(51) Int. Cl.
*C12N 15/86* (2006.01)

(52) U.S. Cl.
CPC .... *C12N 15/86* (2013.01); *C12N 2750/14133* (2013.01); *C12N 2750/14134* (2013.01); *C12N 2795/10133* (2013.01); *C12N 2795/10134* (2013.01)

(58) Field of Classification Search
None
See application file for complete search history.

(56) References Cited

U.S. PATENT DOCUMENTS

| | | | |
|---|---|---|---|
| 9,163,262 B2 | 10/2015 | Rao | |
| 9,328,149 B2 | 5/2016 | Rao et al. | |
| 11,155,835 B2 * | 10/2021 | Rao | C12N 15/86 |
| 2006/0035364 A1 | 2/2006 | Wright et al. | |
| 2014/0336245 A1 | 11/2014 | Mingozzi et al. | |
| 2016/0222414 A1 | 8/2016 | Rabinowitz et al. | |

FOREIGN PATENT DOCUMENTS

| | | |
|---|---|---|
| WO | 99/63348 A1 | 12/1999 |
| WO | 02/094995 A2 | 11/2002 |
| WO | 03/040720 A1 | 5/2003 |
| WO | 2019/169159 A1 | 9/2019 |

OTHER PUBLICATIONS

Ozturk, et al. (Jul. 2019) "A Modular linked-AAV building block system for gene and protein delivery", 60(9): abstract 2901 (Presented over Apr. 28-May 2, 2019). (Year: 2019).*
J. W. Yoo, D. J. Irvine, D. E. Discher, S. Mitragotri, Bio-inspired, bioengineered and biomimetic drug delivery carriers. Nat. Rev. Drug Discov. 10, 521-535 (2011).
M. P. Stewart, A. Sharei, X. Ding, G. Sahay, R. Langer, K. F. Jensen, In vitro and ex vivo strategies for intracellular delivery. Nature 538, 183-192 (2016).
M. Giacca, S. Zacchigna, Virus-mediated gene delivery for human gene therapy. J. ontrolled Release 161, 377-388 (2012).
B. Cao, M. Yang, C. Mao, Phage as a Genetically Modifiable Supramacromolecule in Chemistry, Materials and Medicine. Acc. Chem. Res. 49, 1111-1120 (2016).
M. Karimi, H. Mirshekari, S. M. Moosavi Basri, S. Bahrami, M. Moghoofei, M. R. Hamblin, Bacteriophages and phage-inspired nanocarriers for targeted delivery of therapeutic cargos. Adv. Drug Deliv. Rev. 106, 45-62 (2016).
Z. Zhang, V. I. Kottadiel, R. Vafabakhsh, L. Dai, Y. R. Chemla, T. Ha, V. B. Rao, A promiscuous DNA packaging machine from bacteriophage T4. PLoS Biol. 9, e1000592 (2011).
G. Leffers, V. B. Rao, A discontinuous headful packaging model for packaging less than headful length DNA molecules by bacteriophage T4. J. Mol. Biol. 258, 839-850 (1996).
Q. Li, S. B. Shivachandra, Z. Zhang, V. B. Rao, Assembly of the small outer capsid protein, Soc, on bacteriophage T4: a novel system for high density display of multiple large anthrax toxins and foreign proteins on phage capsid. J. Mol. Biol. 370, 1006-1019 (2007).
A. Bruttin, H. Brussow, Human volunteers receiving *Escherichia coli* phage T4 orally: a safety test of phage therapy. Antimicrob. Agents Chemother. 49, 28742878 (2005).
P. Tao, M. Mahalingam, B. S. Marasa, Z. Zhang, A. K. Chopra, V. B. Rao, In vitro and in vivo delivery of genes and proteins using the bacteriophage T4 DNA packaging machine. Proc. Natl. Acad. Sci. 110, 5846-5851 (2013).
P. Tao, M. Mahalingam, J. Zhu, M. Moayeri, J. Sha, W. S. Lawrence, S. H. Leppla, A. K. Chopra, V. B. Rao, A Bacteriophage T4 Nanoparticle-Based Dual Vaccine against Anthrax and Plague. mBio 9, (2018).
P. Tao, M. Mahalingam, M. L. Kirtley, C. J. van Lier, J. Sha, L. A. Yeager, A. K. Chopra, V. B. Rao, Mutated and bacteriophage T4 nanoparticle arrayed F1-V immunogens from Yersinia pestis as next generation plague vaccines. PLoS Pathog. 9, e1003495 (2013).
P. Tao, X. Wu, V. Rao, Unexpected evolutionary benefit to phages imparted by bacterial CRISPR-Cas9. Sci. Adv. 4, eaar4134 (2018).

(Continued)

*Primary Examiner* — Robert M Kelly
(74) *Attorney, Agent, or Firm* — Ajay A. Jagtiani; Miles & Stockbridge P.C.

(57) ABSTRACT

Described is hybrid viral vector comprising: a first virus such as bacteriophage T4; one or more second virus such as adeno-associated virus (AAV) attached to the first virus through cross-bridges, such as avidin-biotin cross-bridges; one or more DNA molecules packaged in the first virus; one or more nucleic acid molecules packaged in the second virus; and one or more proteins displayed on the surface of the first virus. Also described are methods of making and using such a hybrid viral vector.

4 Claims, 49 Drawing Sheets
(24 of 49 Drawing Sheet(s) Filed in Color)
Specification includes a Sequence Listing.

(56) References Cited

OTHER PUBLICATIONS

P. Tao, X. Wu, W. C. Tang, J. Zhu, V. Rao, Engineering of Bacteriophage T4 Genome Using CRISP R-Cas9. ACS Synth. Biol. 6, 1952-1961 (2017).
R. J. Samulski, N. Muzyczka, AAV-Mediated Gene Therapy for Research and Therapeutic Purposes. Annu. Rev. Virol. 427-451 (2014).
Z. Chen, L. Sun, Z. Zhang, A. Fokine, V. Padilla-Sanchez, D. Hanein, W. Jiang, M. G. Rossmann, V. B. Rao, Cryo-EM structure of the bacteriophage T4 isometric head at 3.3—A resolution and its relevance to the assembly of cosahedral viruses. Proc. Natl. Acad. Sci. 114, E8184-E8193 (2017).
A. Fokine, M. Z. Islam, Z. Zhang, V. D. Bowman, V. B. Rao, M. G. Rossmann, Structure of the three N-terminal Immunoglobulin domains of the highly immunogenic outer capsid protein from a T4-like bacteriophage. J. Virol. 85, 8141-8148 (2011).
C. Summerford, R. J. Samulski, Membrane-associated heparan sulfate proteoglycan is a receptor for adeno-associated virus type 2 virions. J. Virol. 72, 1438-1445 (1998).
G. A. Farr, L. G. Zhang, P. Tattersall, Parvoviral virions deploy a capsid-tethered lipolytic enzyme to breach the endosomal membrane during cell entry. Proc. Natl. Acad. Sci. 102, 17148-17153 (2005).
P. J. Schatz, Use of peptide libraries to map the substrate specificity of a peptide-modifying enzyme: a 13 residue consensus peptide specifies biotinylation in *Escherichia coli*. Biotechnology 11, 1138-1143 (1993).
D. Grimm, J. S. Lee, L. Wang, T. Desai, B. Akache, T. A. Storm, M. A. Kay, In vitro and invivo gene therapy vector evolution via multispecies interbreeding and retargeting of 750 adeno-associated viruses. J. Virol. 82, 5887-5911 (2008).
G. S. Arnold, A. K. Sasser, M. D. Stachler, J. S. Bartlett, Metabolic biotinylation provides a unique platform for the purification and targeting of multiple AAV vector serotypes. Mol. 753 Ther. 14, 97-106 (2006).
V. B. Rao, M. Feiss, Mechanisms of DNA Packaging by Large Double-Stranded DNA 755 Viruses. Annu. Rev. Virol. 2, 851-378 (2015).
P. O. Seglen, B. Grinde, A. E. Solheim, Inhibition of the lysosomal pathway of protein degradation in isolated rat hepatocytes by ammonia, methylamine, chloroquine and leupeptin. Eur. J. Biochem. 95, 215-225 (1979).
2. Zadori, J. Szelei, M. C. Lacoste, Y. Li, S. Gariepy, P. Raymond, M. Allaire, I. R. Nabi, P. Tijssen, A viral phospholipase A2 is required for parvovirus infectivity. Dev. Cell. 1, 291-302 (2001).
M. Penaud-Budloo, C. Le Guiner, A. Nowrouzi, A. Toromanoff, Y. Cherel, P. Chenuaud, M. Schmidt, C. von Kalle, F. Rolling, P. Moullier, R. O. Snyder, Adeno-associated virus vector genomes persist as episomal chromatin in primate muscle. J. Virol. 82, 7875-7885 (2008).
K. T. Gause, A. K. Wheatley, J. Cui, Y. Yan, S. J. Kent, F. Caruso, Immunological Principles Guiding the Rational Design of Particles for Vaccine Delivery. ACS Nano 11, 54-68 (2017).
J. J. Barr, R. Auro, M. Furlan, K. L. Whiteson, M. L. Erb, J. Pogliano, A. Stotland, R. Wolkowicz, A. S. Cutting, K. S. Doran, P. Salamon, M. Youle, F. Rohwer, Bacteriophage adhering to mucus provide a non-host-derived immunity. Proc. Natl. Acad. Sci. 110, 10771-10776 (2013).
M. A. Liu, Immunologic basis of vaccine vectors. Immunity 33, 504-515 (2010).
T. R. Flotte, S. Lu, DNA Vaccination in 2018: An Update. Hum. Gene Ther. 29, 963-965 (2018).
A. Impagliazzo, F. Milder, H. Kuipers, M. V. Wagner, X. Zhu, R. M. Hollman, R. van Meersbergen, J. Huizingh, P. Wanningen, J. Verspuij, M. de Man, Z. Ding, A. Apetri, B. Kukrer, E. Sneekes-Vriese, D. Tomkiewicz, N. S. Laursen, P. S. Lee, A. Zakrzewska, L. Dekking, J. Tolboom, L. Tettero, S. van Meerten, W. Yu, W. Koudstaal, J. Goudsmit, A. B. Ward, W. Meijberg, I. A. Wilson, K. Radosevic, A stable trimeric influenza hemagglutinin stem as a broadly protective Immunogen. Science 349, 1301-1306 (2015).
P. Tao, J. Zhu, M. Mahalingam, H. Batra, V. B. Rao, Bacteriophage T4 nanoparticles for vaccine delivery against Infectious diseases. Adv. Drug Deliv. Rev. (2018). DOI10.1016/j.addr.2018.06.025.
D. Breitfeld, L. Ohl, E. Kremmer, J. Ellwart, F. Sallusto, M. Lipp, R. Forster, Follicular B helper T cells express CXC chemokine receptor 5, localize to B cell follicles, and support immunoglobulin production. J. Exp. Med. 192, 1545-1552 (2000).
C. Havenar-Daughton, M. Lindqvist, A. Heit, J. E. Wu, S. M. Reiss, K. Kendric, S. Belanger, S. P. Kasturi, E. Landais, R. S. Akondy, H. M. McGuire, M. Bothwell, P. A. Vagefi, E. Scully, I. P. C. P. Investigators, G. D. Tomaras, M. M. Davis, P. Poignard, R. Ahmed, B. D. Walker, B. Pulendran, M. J. McElrath, D. E. Kaufmann, S. Crotty, CXCL 13 is a plasma biomarker of germinal center activity. Proc. Natl. Acad. Sci. 113, 2702-2707 (2016).
J. J. Moon, B. Huang, D. J. Irvine, Engineering nano- and microparticles to tune immunity. Adv. Mater. 24, 3724-3746 (2012).
A. Iwasaki, R. Medzhitov, Toll-like receptor control of the adaptive immune responses. Nat.Immunol. 5, 987-995 (2004).
K. Schwarz, T. Stomi, V. Manolova, A. Didierlaurent, J. C. Sirard, P. Rothlisberger, M. F. Bachmann, Role of Toll-like receptors in costimulating cytotoxic T cell responses. Eur. J. Immunol. 33, 1465-1470 (2003).
P. R. Johnson, B. C. Schnepp, M. J. Connell, D. Rohne, S. Robinson, G. R. Krivulka, C. I. Lord, R. Zinn, D. C. Montefiori, N. L. Letvin, K. R. Clark, Novel adeno-associated virus vector vaccine restricts replication of simian Immunodeficiency virus in macaques. J. Virol. 79, 955-965 (2005).
R. Ni, J. Zhou, N. Hossain, Y. Chau, Virus-inspired nucleic acid delivery system: Linking virus and viral mimicry. Adv. Drug Deliv. Rev. 106, 3-26 (2016).
P. Tao, M. Mahalingam, J. Zhu, M. Moayeri, M. L. Kirtley, E. C. Fitts, J. A. Andersson, W. S. Lawrence, S. H. Leppla, A. K. Chopra, V. B. Rao, A Bivalent Anthrax-Plague Vaccine That Can Protect against Two Tier-1 Bioterror Pathogens, Bacillus anthracis and Yersinia pestis. Front. Immunol. 8, 687 (2017).
Office Action received in Chinese Application No. 202080065773.1 issued Jul. 5, 2022.
Office Action received in Japanese Application No. 2022-510123 mailed Aug. 9, 2022.
Office Action received in Korean Application No. 10-2022-7008043 dated Aug. 22, 2022.
Karimi et al., "Bacteriophages and Phage-Inspired Nanocarriers for Targeted Delivery of Therepeutic Cargos", Adv Drug Deliv Rev. (2016).
Pranjol et al., "Bacteriophage-Derived Vectors for Targeted Cancer Gene Therapy", Viruses, vol. 7, pp. 268-284 (2015).
Zhu et al., "A prokaryotic-eukaryotic hybrid vector for delivery of large cargos of genes and proteins into human cells", Science Advances (2019).
International Search Report and Written Opinion received in International PCT Application No. PCT/IB2020/057588 mailed Nov. 20, 2020.
Zhu, J. et al., "A prokaryotic-eukaryotic hybrid viral vector for delivery of large cargos of genes and proteins into human cells", Science advances, vol. 5, article No. eaax0064, pp. 1-14 (2019).
Takahashi, et al. (2000) "Structural requirement for the two-step dimerization of human immunodeficiency virus type I genome", RNA, 6: 96-102. (Year: 2000).
Burova and Ioffe (2005) "Chromatographic purification of recombinant adenoviral and adeno-associated viral vectors: methods and implications", Gene Therapy, 12: S5-S17. (Year: 2005).
Office Action received in Chinese Application No. 202080065773.1 issued Oct. 25, 2022.
Karimi et al., "Bacteriophages and Phage-Inspired Nanocarriers for Targeted Delivery of Therapeutic Cargos", Adv. Drug. Deliv. Rev., 106(Pt A): pp. 45-62 (2016).
Decision on Rejection received in Japanese Application No. 2022-510123 issued Jan. 11, 2023.
Office Action received in Korean Application No. 10-2022-7008043 dated Feb. 27, 2023.

(56) References Cited

OTHER PUBLICATIONS

Zhu et al., "A prokaryotic-eukaryotic hybrid vector for delivery of large cargos of genes and proteins into human cells", Science Advances, 5(8) 2019, eaax0064, 14 pages.
Non-Final Office Action received in U.S. Appl. No. 17/359,711 mailed Jan. 21, 2022.
Final Office Action received in U.S. Appl. No. 17/359,711 mailed Feb. 11, 2022.
Zhu et al., "A universal bacteriophage T4 nanoparticle platform to design multiplex SARS-COV-2 vaccine candidates by CRISPR engineering", Science Advances, 7, Article eabh 1547, pp. 1-18 (2021).
Karimi et al., "Bacteriophages and Phage-Inspired Nanocarriers for Targeted Delivery of Therapeutic Cargos", Adv. Drug. Deliv. Rev., pp. 45-62 (2016).
Pranjol et al., "Bacteriophage-Derived Vectors for Targeted Cancer Gene Therapy", Viruses, 7, pp. 268-284 (2015).
Official Action received in Canadian Application No. 3,148,369 dated May 11, 2023.
Official Action received in Chinese Application No. 202080065773.1 dated Mar. 15, 2023.
1 Extended European Search Report received in European Application No. 20855101.0 dated Aug. 28, 2023.

\* cited by examiner

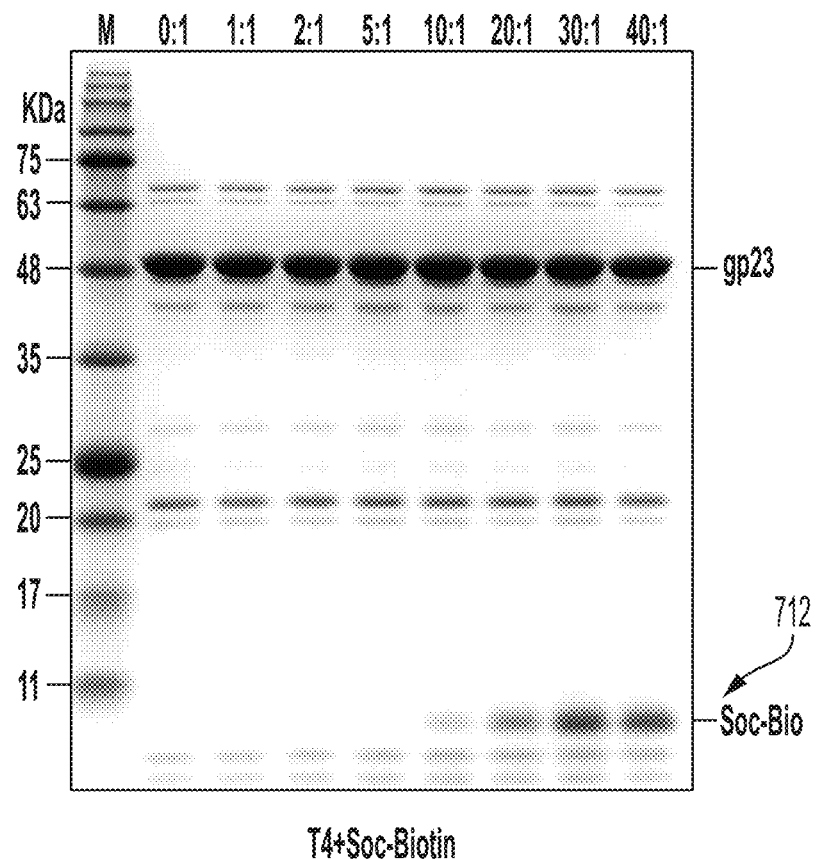
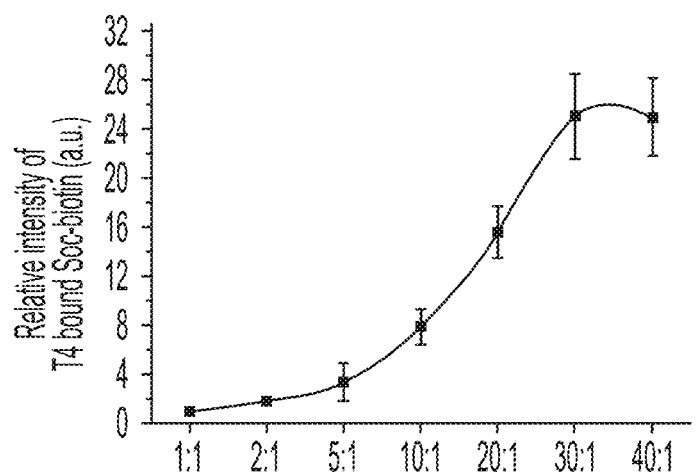
FIG. 5

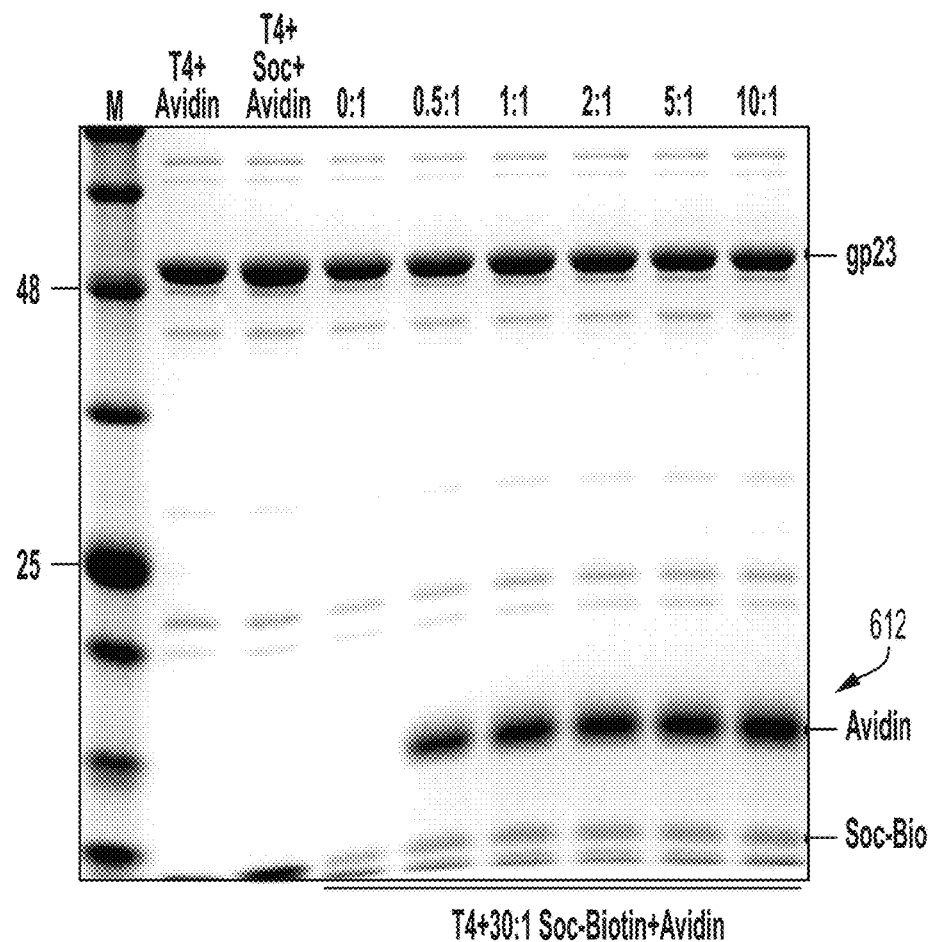
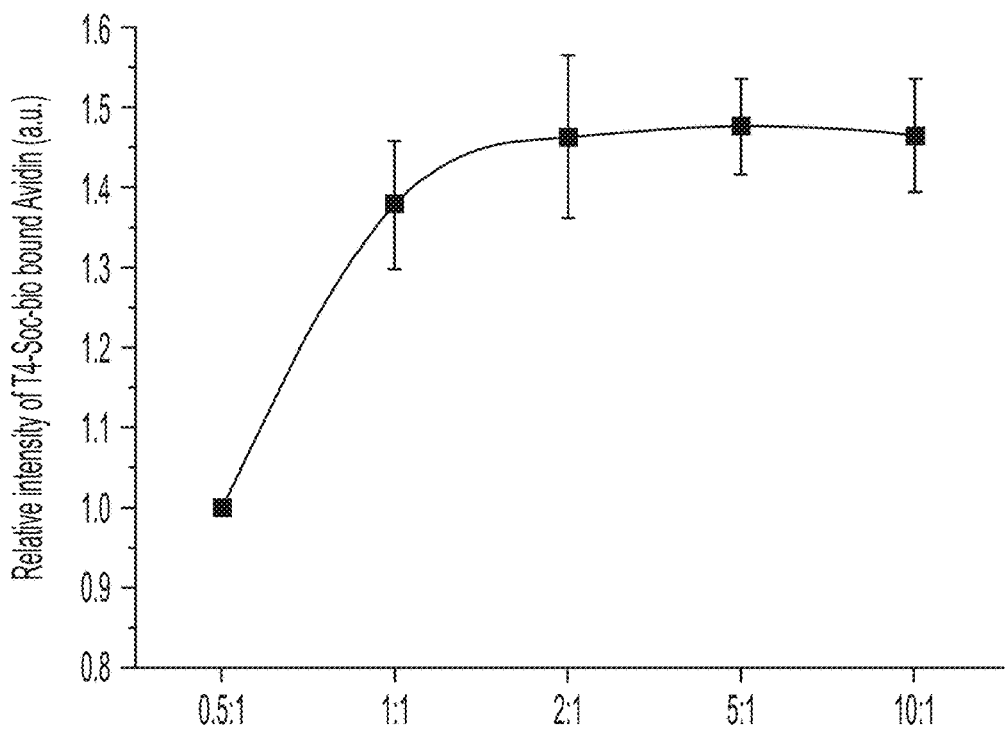
FIG. 6

SEQUENCE LISTING

```
<160> NUMBER OF SEQ ID NOS: 8

<210> SEQ ID NO 1
<211> LENGTH: 50
<212> TYPE: DNA
<213> ORGANISM: Artificial Sequence
<220> FEATURE:
<223> OTHER INFORMATION: Synthetic primer: FW1

<400> SEQUENCE: 1
atcgagtggc acgagggtct ttcgatgact tttacagttg atataactcc            50

<210> SEQ ID NO 2
<211> LENGTH: 64
<212> TYPE: DNA
<213> ORGANISM: Artificial Sequence
<220> FEATURE:
<223> OTHER INFORMATION: Synthetic primer: FW2

<400> SEQUENCE: 2
ttctagctag cggtcttaac gacatcttcg aggcacagaa gatcgagtgg cacgagggtc   60
ttcg                                                              64

<210> SEQ ID NO 3
<211> LENGTH: 39
<212> TYPE: DNA
<213> ORGANISM: Artificial Sequence
<220> FEATURE:
<223> OTHER INFORMATION: Synthetic primer: RW

<400> SEQUENCE: 3
ataaagcttt tatggatagg tatagatgat accagtttc                        39

<210> SEQ ID NO 4
<211> LENGTH: 30
<212> TYPE: DNA
<213> ORGANISM: Artificial Sequence
<220> FEATURE:
<223> OTHER INFORMATION: Synthetic primer: AN-F

<400> SEQUENCE: 4
cgcggaagct tcgatcaact acgcagacag                                  30

<210> SEQ ID NO 5
<211> LENGTH: 30
<212> TYPE: DNA
<213> ORGANISM: Artificial Sequence
<220> FEATURE:
<223> OTHER INFORMATION: Synthetic primer: HD-AN-R

<400> SEQUENCE: 5
gtttgcctcg agggccgcgg cgtctgcctc                                  30
```

```
<210> SEQ ID NO 6
<211> LENGTH: 45
<212> TYPE: DNA
<213> ORGANISM: Artificial Sequence
<220> FEATURE:
<223> OTHER INFORMATION: Synthetic primer: HD-AN-F

<400> SEQUENCE: 6
ccgcggccct cgaggcaaac aaagcctacg accggcagct cgaca          45

<210> SEQ ID NO 7
<211> LENGTH: 30
<212> TYPE: DNA
<213> ORGANISM: Artificial Sequence
<220> FEATURE:
<223> OTHER INFORMATION: Synthetic primer: AN-R

<400> SEQUENCE: 7
gagaacgtac ggcagctggt actccgagtc                            30

<210> SEQ ID NO 8
<211> LENGTH: 15
<212> TYPE: PRT
<213> ORGANISM: Artificial Sequence
<220> FEATURE:
<223> OTHER INFORMATION: Synthetic: biotin acceptor peptide (BAP)

<400> SEQUENCE: 8

Gly Leu Asn Asp Ile Phe Glu Ala Gln Lys Ile Glu Trp His Glu
1               5                   10                  15
```

US 12,037,597 B2

PROKARYOTIC-EUKARYOTIC HYBRID VIRAL VECTOR FOR DELIVERY OF LARGE CARGOS OF GENES AND PROTEINS INTO HUMAN CELLS

CROSS-REFERENCE TO RELATED APPLICATIONS

This application is a divisional application of U.S. patent application Ser. No. 16/990,289 filed on Aug. 11, 2020, entitled "A PROKARYOTIC-EUKARYOTIC HYBRID VIRAL VECTOR FOR DELIVERY OF LARGE CARGOS OF GENES AND PROTEINS INTO HUMAN CELLS" which claims benefit of priority of U.S. patent application Ser. No. 62/888,576 filed on Aug. 19, 2019, entitled "A PROKARYOTIC-EUKARYOTIC HYBRID VIRAL VECTOR FOR DELIVERY OF LARGE CARGOS OF GENES AND PROTEINS INTO HUMAN CELLS". The entire contents and disclosures of this patent application are incorporated herein by reference in their entirety.

GOVERNMENT INTEREST STATEMENT

This invention was made with the United States government support under Grant Nos. AI111538 and AI081726 awarded by NIAID AND NIH. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "109007-23530US01_ST25.txt" created on Aug. 7, 2020 and is 2,079 bytes in size. The sequence listing contained in this .txt file is part of the specification and is hereby incorporated by reference herein in its entirety.

BACKGROUND

Field of the Invention

The present invention relates generally to protein and nucleic acid delivery components, compositions, mechanisms and methods of delivery thereof.

Background of the Invention

Delivery of genes and proteins into target cells would be essential for mechanistic research and the prevention and treatment of many human diseases such as cancer, infectious diseases and genetic diseases. However, formulating a vehicle that can efficiently and safely deliver both genes and proteins into the target cell is still a major challenge. The present application overcomes the shortcomings of the prior art as described herein.

SUMMARY

According to a first broad aspect, the present invention provides a product comprising a hybrid viral vector (e.g. T4-AAV) comprising: a first virus (e.g. bacteriophage T4); one or more second virus (e.g. adeno-associated virus, AAV) attached to the head of the prokaryotic virus through cross-bridges (e.g. avidin-biotin cross-bridges).

According to a second broad aspect, the present invention provides a method comprising the following steps: designing an avidin-biotin cross-bridges; attaching one end of the cross-bridge (Soc or Hoc) to the first virus (bacteriophage T4); and attaching the other end of the cross-bridge (avidin) to the second virus (AAV).

According to a third broad aspect, the present invention provides a method comprising the following steps: exposing cells of a biological specimen to a hybrid viral vector (T4-AAV) thereby bind the vector to the cells or administering the hybrid vector to a biological specimen, wherein the vector comprises one or more molecules of nucleic acid packaged in either the first or second vector or both, wherein there are optionally one or more Soc-fused proteins displayed on the surface of the first virus, and wherein the vector is internalized within the cells, wherein internalization of the vector within the cells causes the release of the packaged nucleic acid into the cytosol of each of the cells, wherein the release of the packaged one or more molecules of nucleic acid into the cytosol of each of the cells causes entry of the one or more molecules of nucleic acid into the nucleus of each of the cells, wherein the entry of the one or more molecules of nucleic acid into the nucleus of each of the cells causes transcription of the DNA or reverse transcription of the RNA and over-expression of protein(s) encoded by the nucleic acid.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The accompanying drawings, which are incorporated herein and constitute part of this specification, illustrate exemplary embodiments of the invention, and, together with the general description given above and the detailed description given below, serve to explain the features of the invention.

FIG. 5 is a graph showing attachment of BAP to Hoc according to one embodiment of the present invention.

FIG. 6 is a graph showing the biotinylation of Hoc-BAP according to one embodiment of the present invention.

DETAILED DESCRIPTION OF THE INVENTION

Definitions

Figure 1:
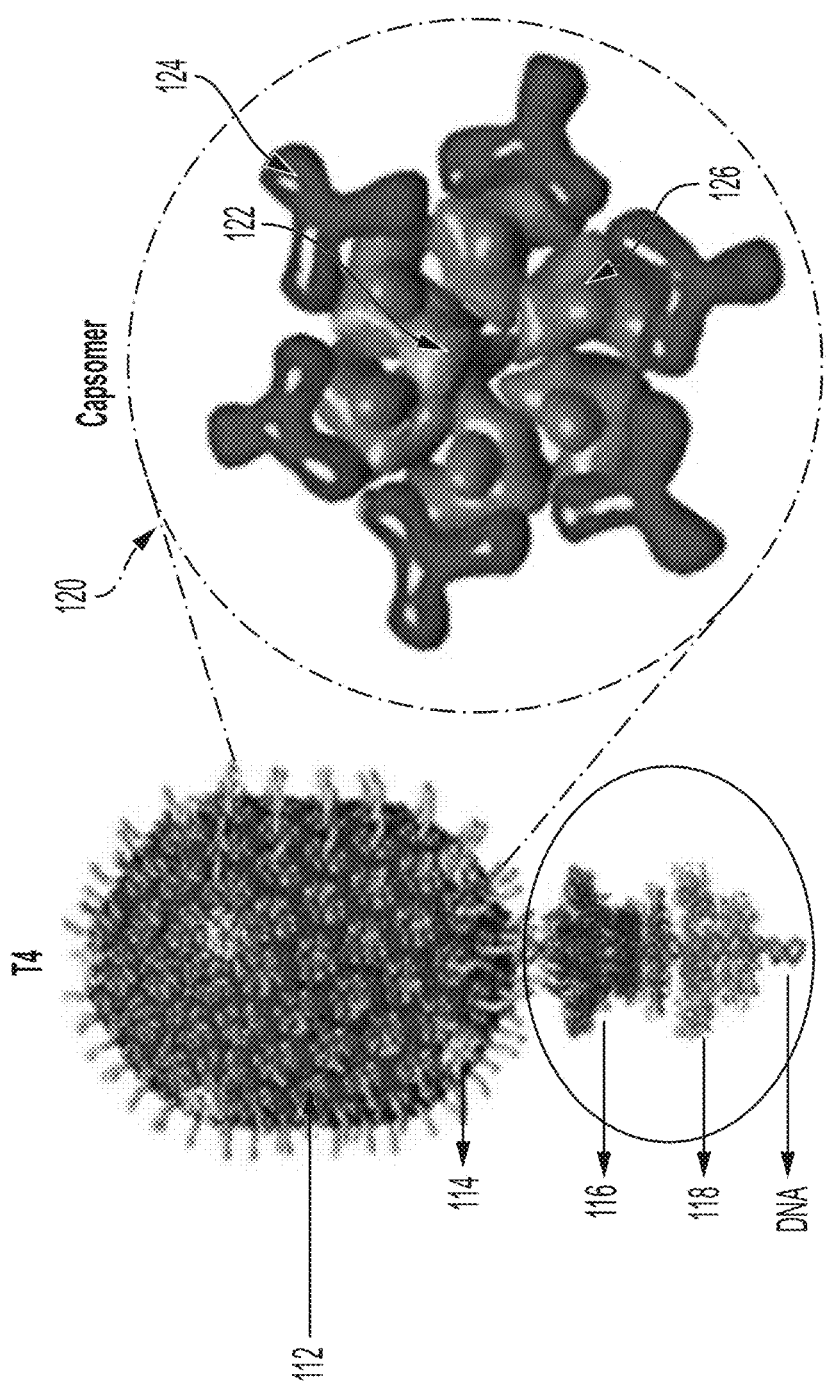
FIG. 1 is a schematic diagram of the bacteriophage T4 according to one embodiment of the present invention.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present invention, the term "comprising", the term "having", the term "including," and variations of these words are intended to be open-ended and mean that there may be additional elements other than the listed elements.

For purposes of the present invention, directional terms such as "top," "bottom," "upper," "lower," "above," "below," "left," "right," "horizontal," "vertical," "up," "down," etc., are used merely for convenience in describing the various embodiments of the present invention. The embodiments of the present invention may be oriented in various ways. For example, the diagrams, apparatuses, etc., shown in the drawing figures may be flipped over, rotated by 90° in any direction, reversed, etc.

For purposes of the present invention, a value or property is "based" on a particular value, property, the satisfaction of a condition, or other factors, if that value is derived by performing a mathematical calculation or logical decision using that value, property or other factor.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "bind," the term "binding" and the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "vector", "vehicle", and "nanoparticle" are used interchangeably. These terms refer to a virus or a hybrid viral particle that can be used to deliver genes or proteins.

For purposes of the present invention, the term "tropism" refers to the tendency of a virus to infect a particular host cell or tissue.

For purposes of the present invention, the term "biological sample" and the term "biological specimen" refers to either a part or the whole of a human, vertebrate animal, invertebrate animal, microbe or plant in vitro or in vivo. The term includes but is not limited to material of human, vertebrate animal, invertebrate animal, microbe or plant origin such as human, animal, microbial or plant tissue sections, cell or tissue cultures, suspension of human, vertebrate animal, invertebrate animal, microbial or plant cells or isolated parts thereof, human or animal biopsies, blood samples, cell-containing fluids and secretion.

For purposes of the present invention, the term "capsid" and the term "capsid shell" refers to the protein shell of a virus comprising several structural subunits of proteins. The capsid encloses the nucleic acid core of the virus.

For purposes of the present invention, the term "nucleic acid" refers to polymers of nucleotides of any length, and include DNA and RNA. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term should also be understood to include both linear and circular DNA. The term as used herein also encompasses cDNA, that is complementary, or copy, DNA produced from an RNA template, for example by the action of reverse transcriptase.

For purposes of the present invention, the term "immune response" refers to a specific response of the immune system of a biological specimen to antigen or immunogen. Immune response may include the production of antibodies and cellular immunity.

For purposes of the present invention, the term "immunity" refers to a state of resistance of a biological specimen to an infecting organism or substance. It will be understood that an infecting organism or substance is defined broadly and includes parasites, toxic substances, cancer cells and other cells as well as bacteria and viruses.

For purposes of the present invention, the term "immunization conditions" refers to factors that affect an immune response including the amount and kind of immunogen or adjuvant delivered to a biological specimen, method of delivery, number of inoculations, interval of inoculations, the type of biological specimen and its condition. "Vaccine" refers to pharmaceutical formulations able to induce immunity.

For purposes of the present invention, the term "immunization dose" refers to the amount of antigen or immunogen needed to precipitate an immune response. This amount will vary with the presence and effectiveness of various adjuvants. This amount will vary with the biological specimen and the antigen, immunogen and/or adjuvant but will generally be between about 0.1 µg/ml or less and about 100 µg per inoculation.

For purposes of the present invention, the term "neck protein" and the term "tail protein" refers to proteins that are involved in the assembly of any part of the necks or tails of a virus particle, in particular bacteriophages. Tailed bacteriophages belong to the order Caudovirales and include three families: The Siphoviridae have long flexible tails and constitute the majority of the tailed viruses. Myoviridae have long rigid tails and are fully characterized by the tail sheath that contracts upon phage attachment to bacterial host. The smallest family of tailed viruses are podoviruses (phage with short, leg-like tails). For example, in T4 bacteriophage gp10 associates with gp11 to forms the tail pins of the baseplate. Tail-pin assembly is the first step of tail assembly. The tail of bacteriophage T4 consists of a contractile sheath surrounding a rigid tube and terminating in a multiprotein baseplate, to which the long and short tail fibers of the phage are attached. Once the heads are packaged with DNA, the proteins gp13, gp14 and gp15 assemble into a neck that seals of the packaged heads, with gp13 protein directly interacting with the portal protein gp20 following DNA packaging and gp14 and gp15 then assembling on the gp13 platform. Neck and tail proteins in T4 bacteriophage may include but are not limited to proteins gp6, gp25, gp53, gp8, gp10, gp11, gp7, gp29, gp27, gp5, gp28, gp12, gp9, gp48, gp54, gp3, gp18, gp19, gp13, gp14, gp15 and gp63.

For purposes of the present invention, the term "purified" refers to the component in a relatively pure state—e.g. at least about 90% pure, or at least about 95% pure or at least about 98% pure.

DESCRIPTION

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Delivery of genes and proteins into target cells forms would be essential for mechanistic research and the prevention and treatment of many human diseases such as cancer, infectious diseases and genetic diseases. Viral vectors have been exploited as a vehicle of delivering genes and proteins into target cells. Commonly used viral vectors include eukaryotic viral vectors and prokaryotic viral vectors.

Eukaryotic viral vectors such as adenoviruses, adeno-associated viruses (AAV), retroviruses and/or lentiviruses have naturally evolved to deliver their genomes efficiently into mammalian cells, making them capable of delivering genes into human cells. However, eukaryotic viral vectors such as AAV are not efficient delivery vehicle, because of their limited delivery capacity: (1) they can only deliver one or two genes and 4-8 kb in size; and (2) they are not suitable for delivering proteins. Furthermore, their tropism to and toxicity for human cells, pre-existing immunity, and safety concerns restrict their broad application[2].

Prokaryotic viral vectors, such as bacteriophage (phage) T4, overcome the drawbacks of eukaryotic viral vectors[4-13]. However, phages are also not efficient delivery vehicles because they lack natural mechanisms to enter mammalian cells or reach appropriate intracellular compartments following entry. FIG. 1, 112 is a structural model of phage, T4. As shown in the surface view 120 in FIG. 1, the T4 head capsomer consists of capsid protein gp23* ("*" represents the cleaved mature form of gp23) 126, and two non-essential outer capsid proteins, Soc 124 and Hoc 122. It was discovered that Soc and Hoc can be used for the display of a variety of foreign proteins, including short polypeptides, large domains, full-length proteins, or multimeric complexes[8, 10]. These findings raised the question of whether an eukaryotic viral particle can be attached to the phage to make a more efficient delivery vehicle for cell-associated biological specimen. In one embodiment, the present invention provides a hybrid viral vector uniquely designed for delivering of genes and proteins into target cells with high efficiency. The methods and composition of the present invention may be used for effective vaccine, genetic therapies and research tools in the biotechnology fields.

Design and Construction of T4-AAV Hybrid Viral Vector

Figure 2:
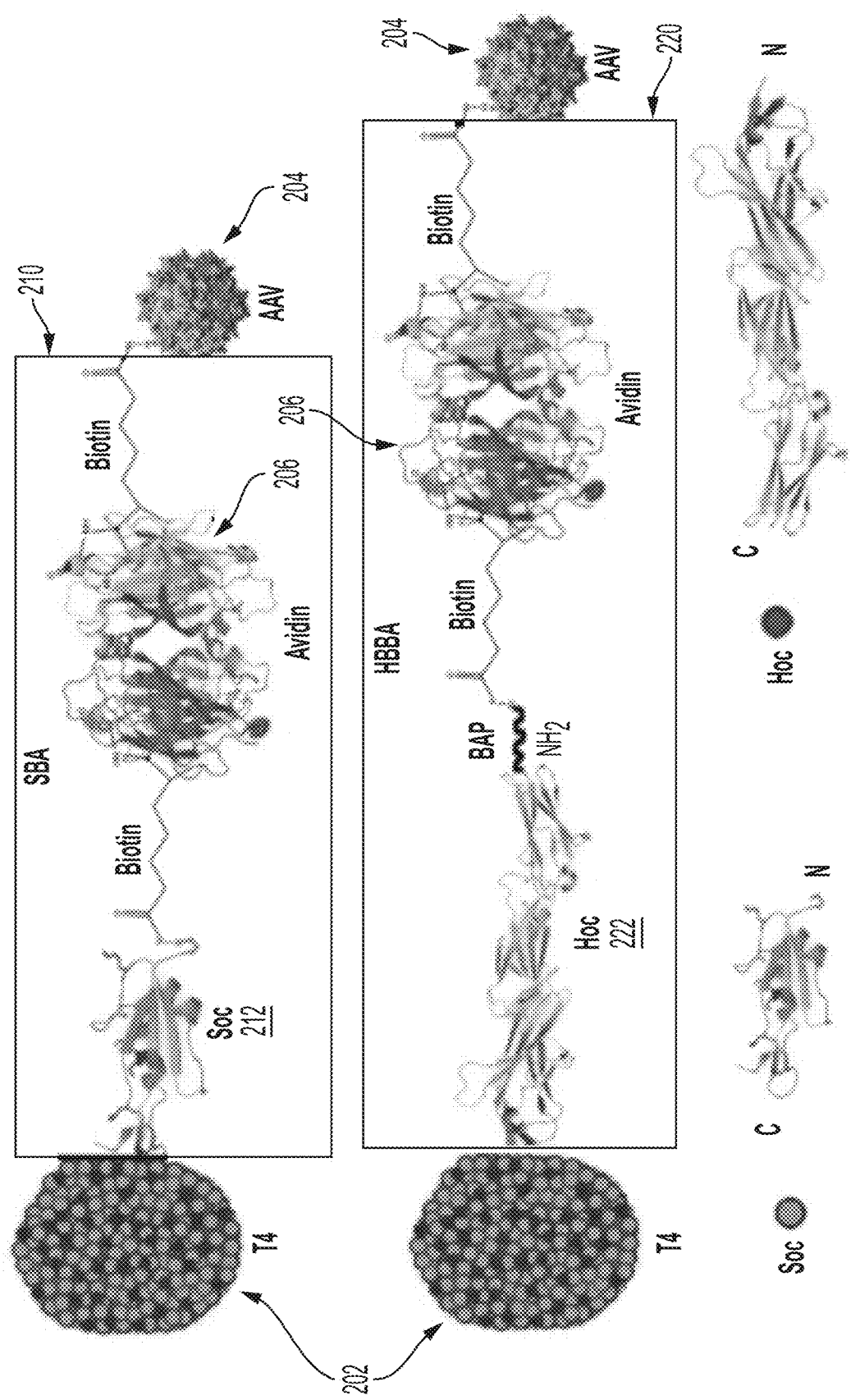
FIG. 2 is a schematic diagram of the T4-AAV hybrid viral vector according to one embodiment of the present invention.

In one embodiment, the present invention provides a T4-AAV hybrid viral vector by attached AAV to a T4 head through a biotin-avidin bridge. As shown in FIG. 2, AAV is attached to T4 head by two types of bridge molecules, Soc-biotin-avidin (SBA) 210 and Hoc-biotin acceptor peptide (BAP)-biotin-avidin (HBBA) 220. Soc 212 and Hoc 222 attach to the T4 head 202 and avidin 206 attaches to biotinylated AAV 204 on the other side.

In one embodiment, the present invention provides a method of producing the Soc-bridged T4-AAV hybrid viral vector, comprising steps: (1) biotinylation of Soc protein; (2) attaching the biotinylated Soc (Soc-biotin) protein to T4 head to produce T4-Soc-biotin; (3) attaching avidin to T4-Soc-biotin to produce T4-Soc-avidin (TSA); (4) biotinylation of AAV; (5) attaching biotinylated AAV to TSA by binding the biotin on AAV to avidin.

In another embodiment, the present invention provides a method of producing the Hoc-bridged T4-AAV hybrid viral vector, comprising steps: (1) attaching biotin acceptor peptide (BAP) to Hoc protein to produce Hoc-BAP; (2) biotinylation of Hoc-BAP to form HBB; (2) attaching avidin to HBB to form HBBA; (3) attaching HBBA to T4 head to produce THA; (4) biotinylation of AAV; (5) attaching biotinylated AAV to THA by binding the biotin on AAV to avidin.

Creating TSA

Figure 3:
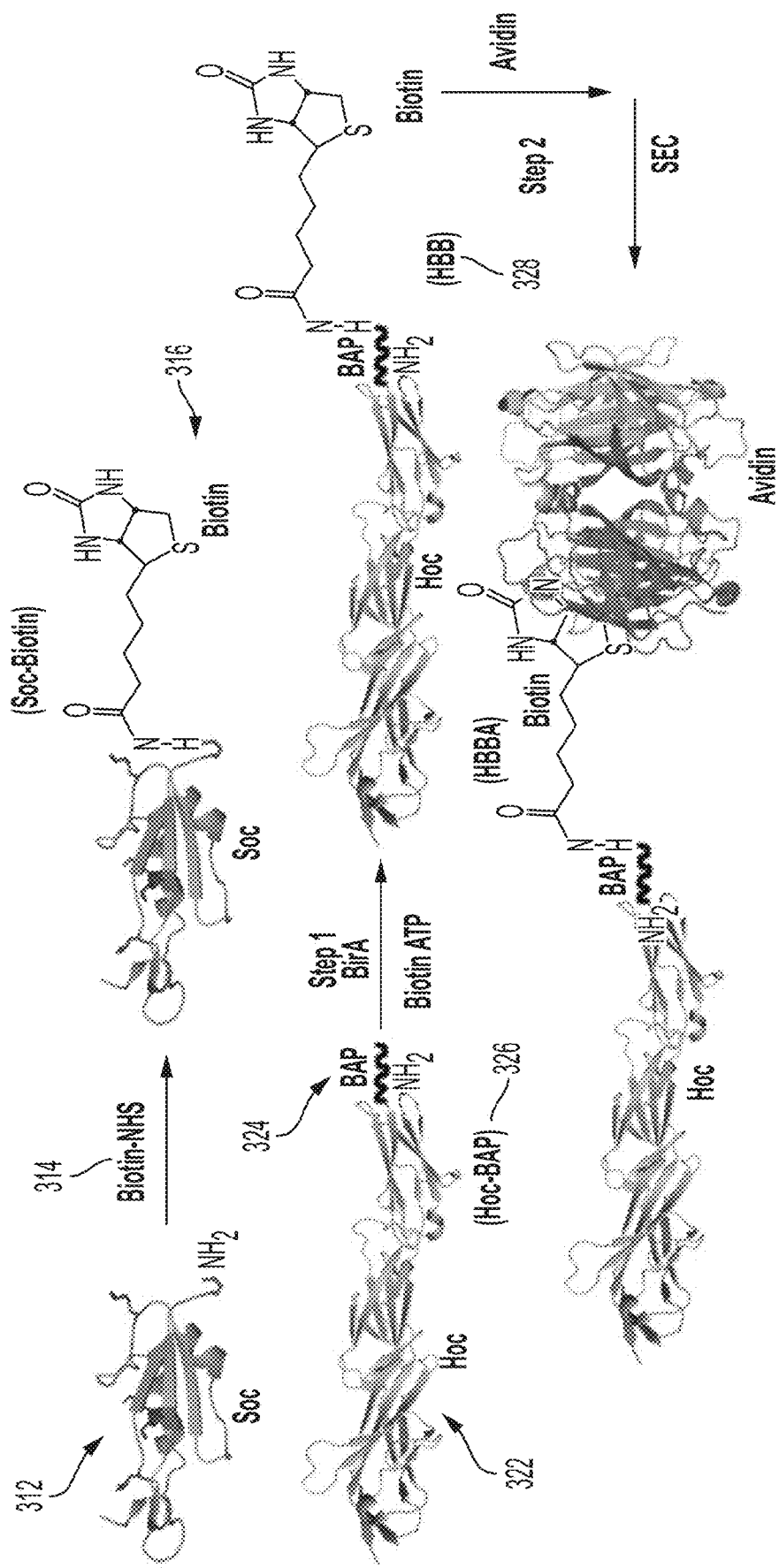
FIG. 3 is a schematic diagram showing the steps of T4-AAV assembly according to one embodiment of the present invention.
Figure 4:
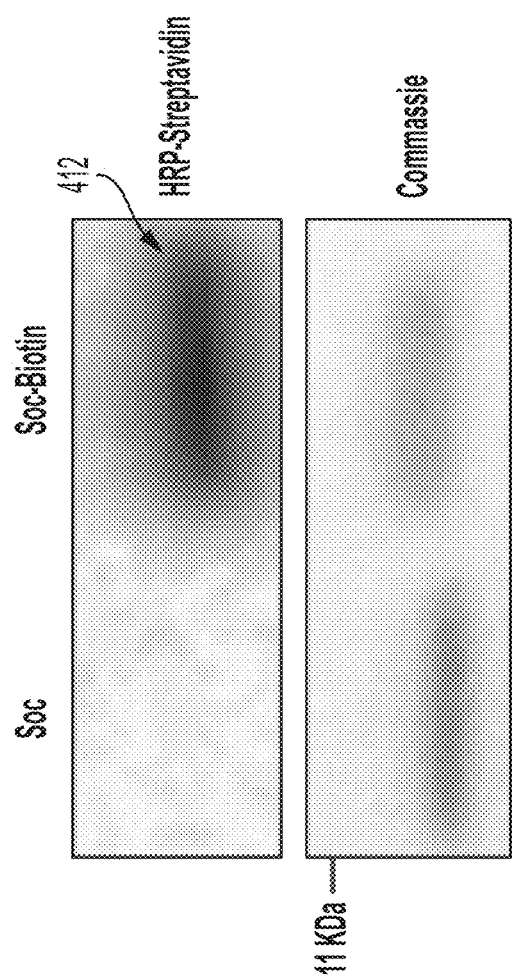
FIG. 4 is a graph showing the biotinylation of Soc protein according to one embodiment of the present invention.

FIG. 3 illustrates the steps of creating Soc-biotin. To produce Soc-Biotin 316, the purified Soc protein 312 was first biotinylated by activation with biotin-N-hydroxysuccinimide-ester (NHS) 314 (FIG. 3). The efficient biotinylation of Soc 412 is confirmed, as shown in FIG. 4.

Next, Soc-biotin is attached to the T4 head. As shown in FIG. 5, binding of biotinylated Soc increases with an increasing ratio of Soc-biotin molecules to capsid binding sites, as indicated by the increasing amount of Soc-biotin 712. At a ratio of 30:1, the relative intensity of T4 bound Soc-biotin peaks (FIG. 5), suggesting nearly all the capsid binding sites were occupied by Soc-biotin. Subsequently, avidin binds to T4-Soc-biotin forming TSA. Binding of avidin to T4-Soc-biotin also increases with an increasing ratio of avidin to T4-Soc-biotin ratio, as indicated by the increasing amount of avidin in TSA 612 (FIG. 6). At a ratio of 2:1, the relative intensity of T4-Soc-Biotin bound avidin peaks, suggesting nearly all T4-Soc-biotin has avidin attached (FIG. 6).

Creating THA

Figure 7:
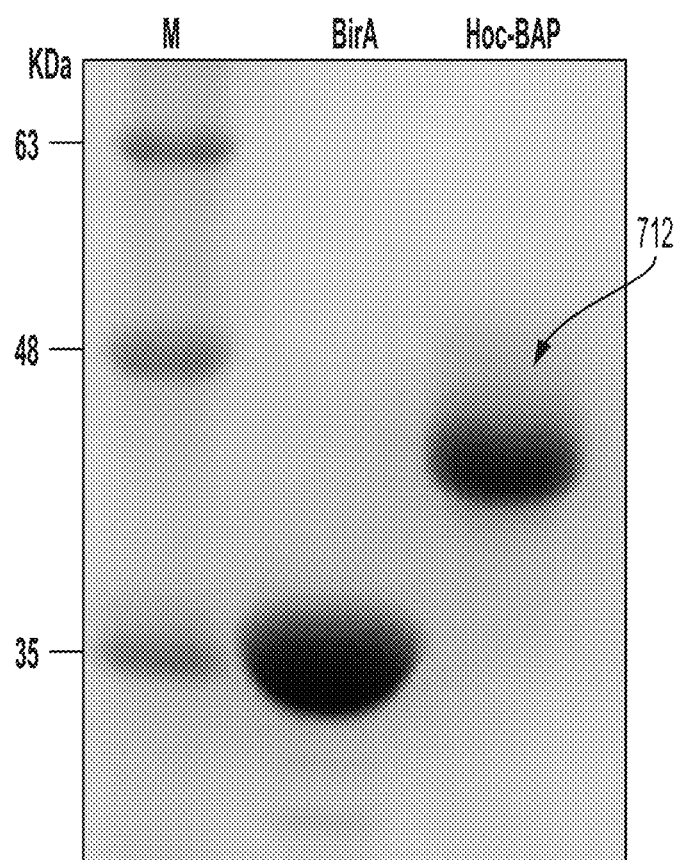
FIG. 7 is a graph showing the attachment of Soc-biotin to T4 at different ratio according to one embodiment of the present invention.
Figure 8:
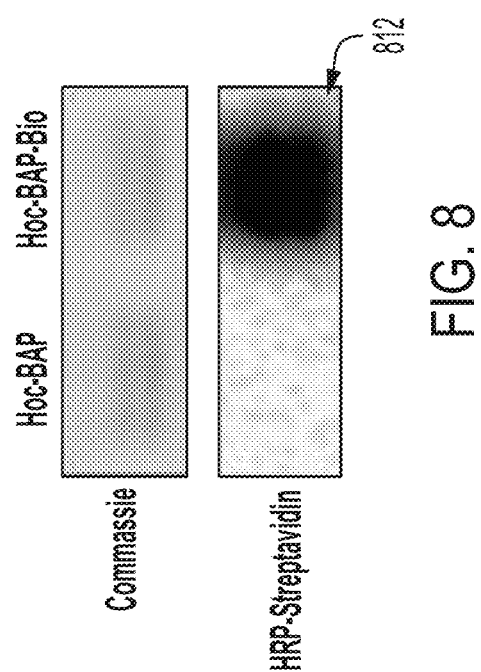
FIG. 8 is a graph showing the attachment of avidin to T4-Soc-biotin at different ratio according to an exemplary embodiment of the present invention.

FIG. 3 illustrates the steps of creating Hoc-biotin. To produce Hoc bridges, BAP 324 is first attached to the N-terminus of Hoc 322 (FIG. 3). The attachment of BAP to Hoc 712 is confirmed as shown in FIG. 7. The Hoc-BAP 326 is then biotinylated using biotin ligase (BirA), as shown in FIG. 3. Biotinylation of Hoc-BAP 812 is confirmed, as shown in FIG. 8.

Figure 9:
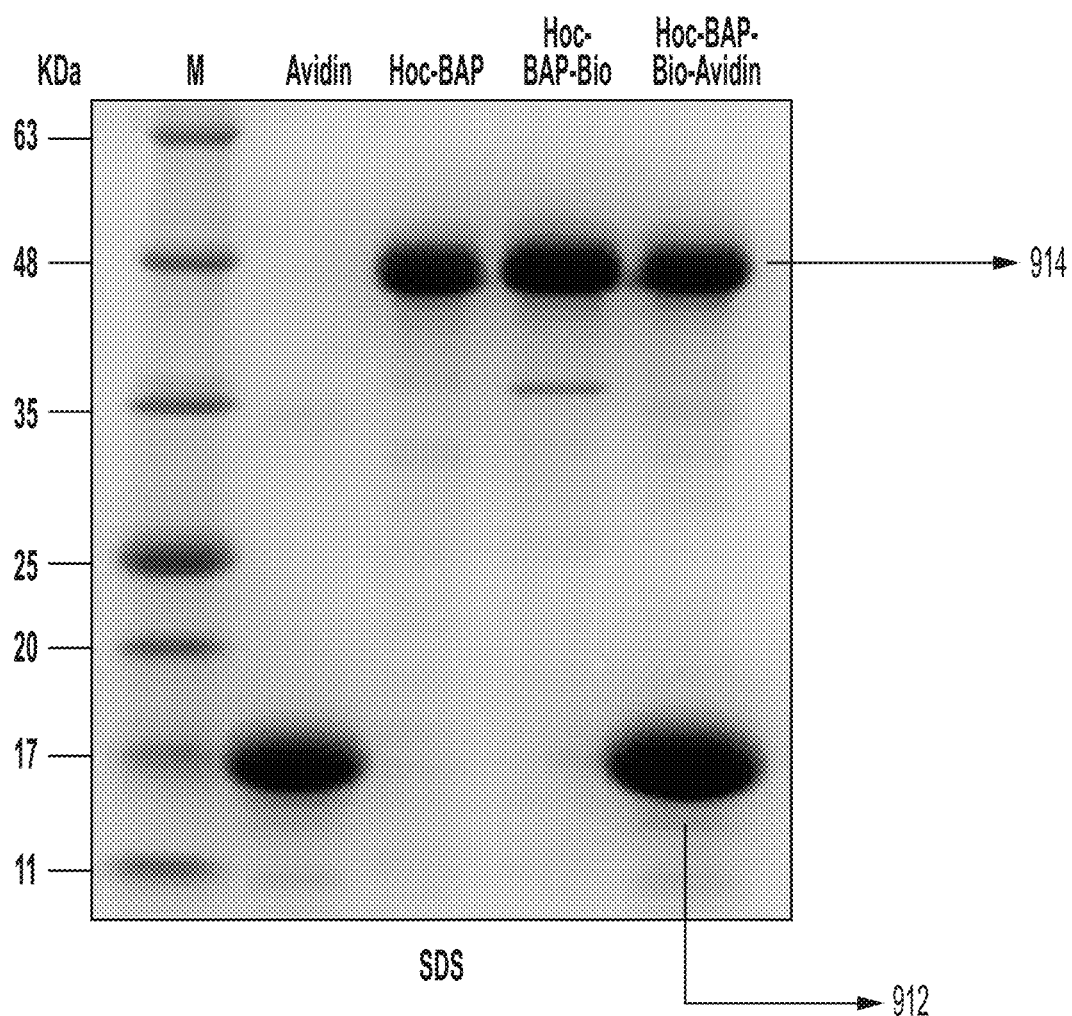
FIG. 9 is a graph showing the attachment of avidin to Hoc-BAP-biotin according to an exemplary embodiment of the present invention.
Figure 10:
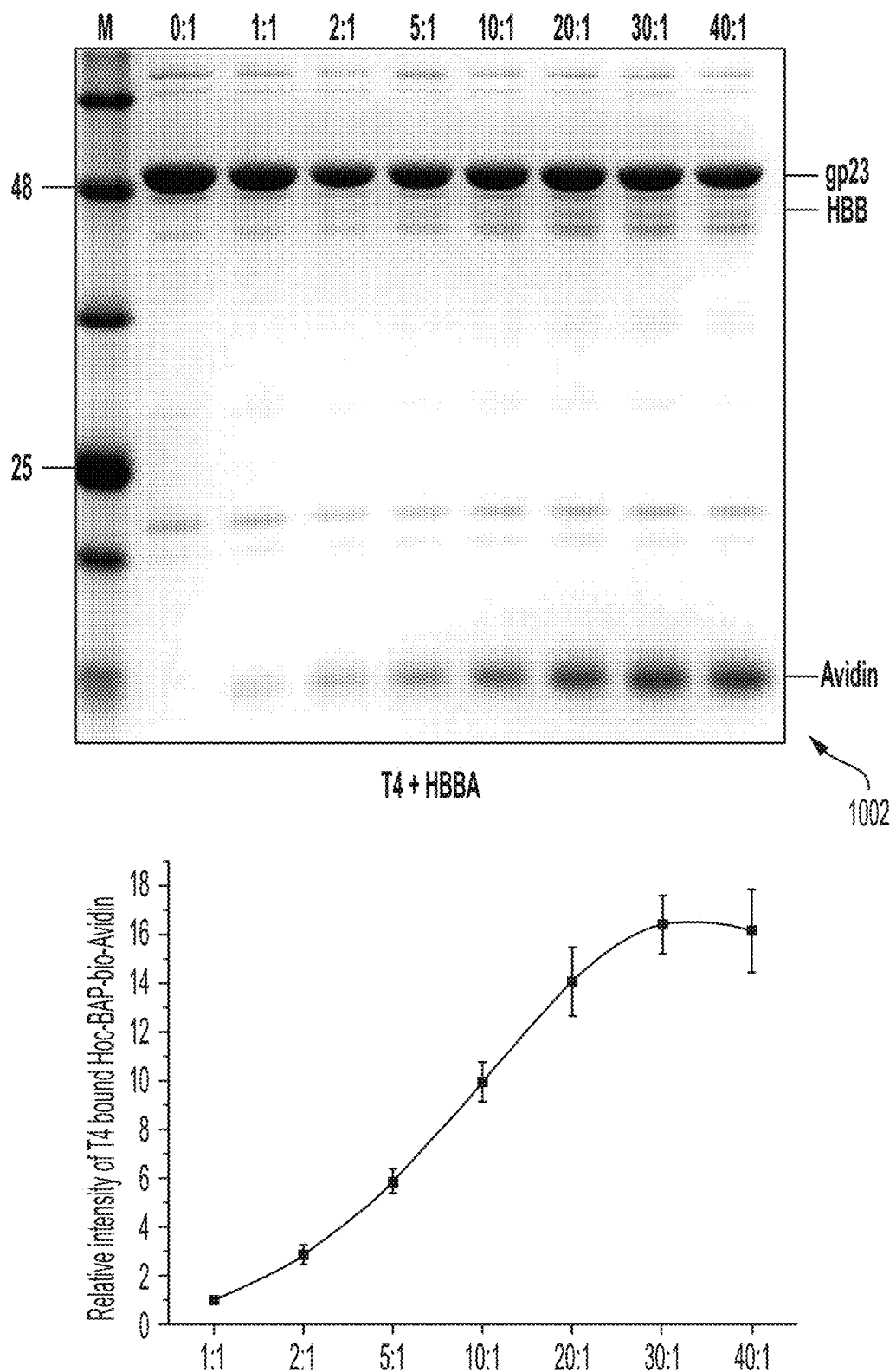
FIG. 10 is a graph showing the attachment of HBBA to T4 at different ratio according to an exemplary embodiment of the present invention.

Subsequently, avidin is attached to biotinylated Hoc-BAP (HBB) 328, forming HBBA. HBBA is then attached to T4 to efficiently form THA 912 (FIG. 9). Binding of HBBA increases with an increasing ratio of HBBA molecules to capsid binding sites, as indicated by the increasing amount to avidin in THA 1002. At a ratio of 30:1, the relative intensity of T4 bound Hoc-BAP-biotin-avidin peaks (FIG. 10), suggesting nearly all binding sites occupied.

Biotinylation and Attachment of AAV

Figure 11:
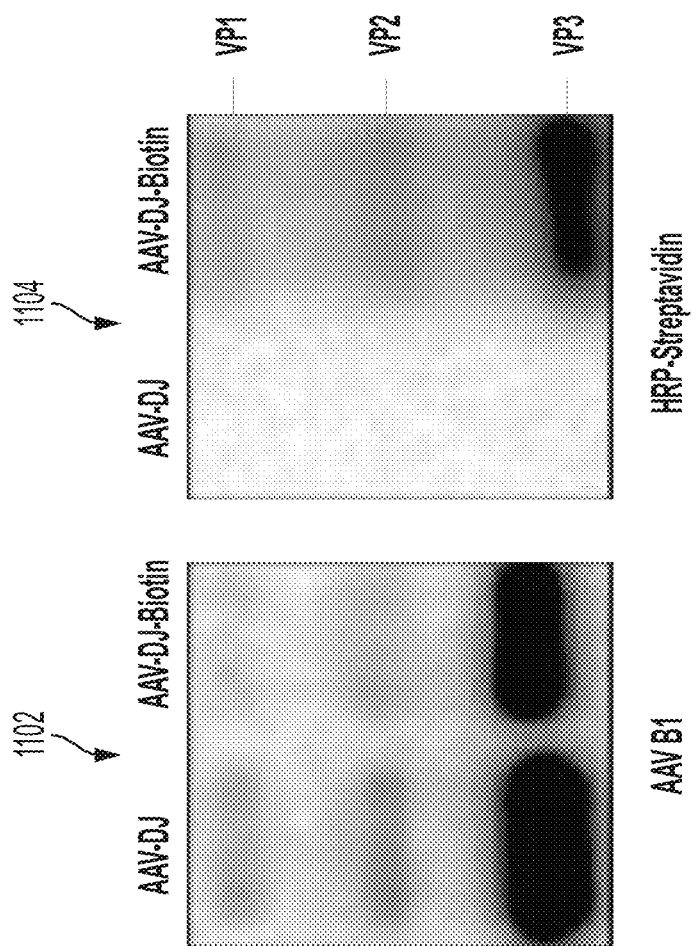
FIG. 11 is a graph showing the biotinylation of AAV according to an exemplary embodiment of the present invention.

To attach AAV to T4, AAV-DJ, virus particles were first biotinylated by activation with biotin-NHS. AAV-DJ contains three AAV capsid proteins, VP1, VP2, and VP3. The biotinylation of all three AAV capsid proteins is confirmed as shown in FIG. 11. In FIG. 11, column 1102 shows the detection of AAV capsid proteins and column 1104 shows the detection of biotin.

Figure 12:
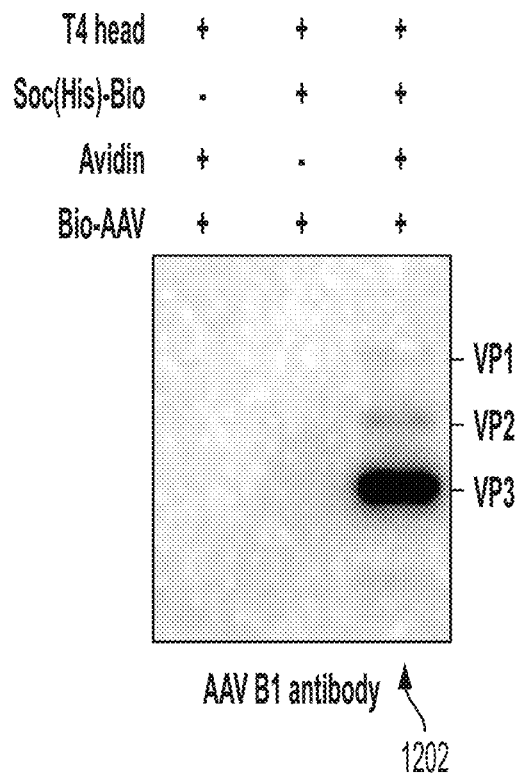
FIG. 12 is a graph showing the amount of unbounded AAV at different AAV to T4 ratio form of chewable tablet according to an exemplary embodiment of the present invention.
Figure 13:
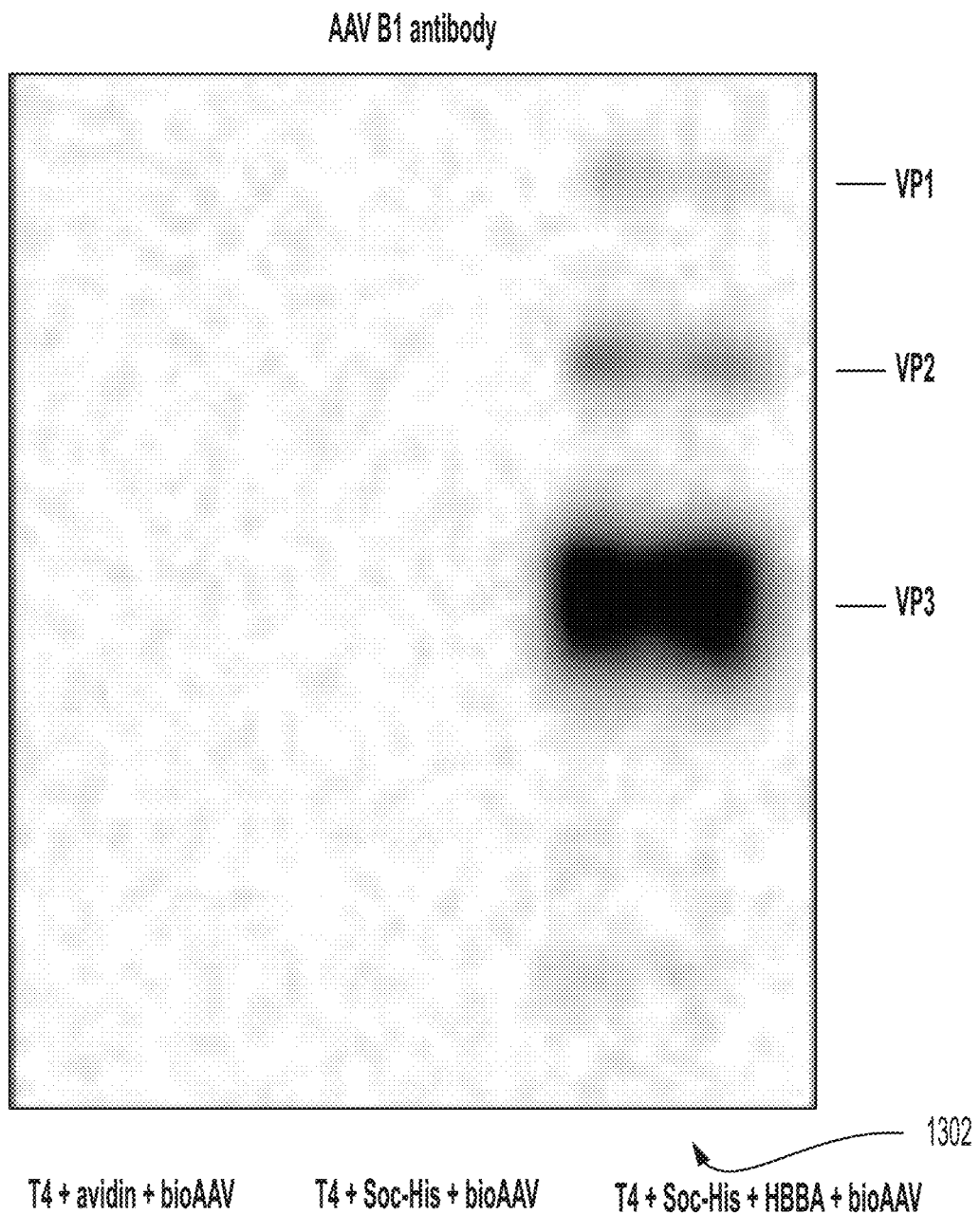
FIG. 13 is an electron micrograph showing the attachment of AAV to T4 according to an exemplary embodiment of the present invention.

The biotinylated AAV-DJ particles are then attached to the TSA and THA bridges through the binding of avidin and the biotin on AAV-DJ particles (FIGS. 12 and 13). FIG. 12 confirms the efficient attachment of AAV to TSA, with column 1202 showing the detection of AAV capsid proteins. FIG. 13 confirms the efficient attachment of AAV to THA, with column 1302 showing the detection of AAV capsid proteins.

Figure 14:
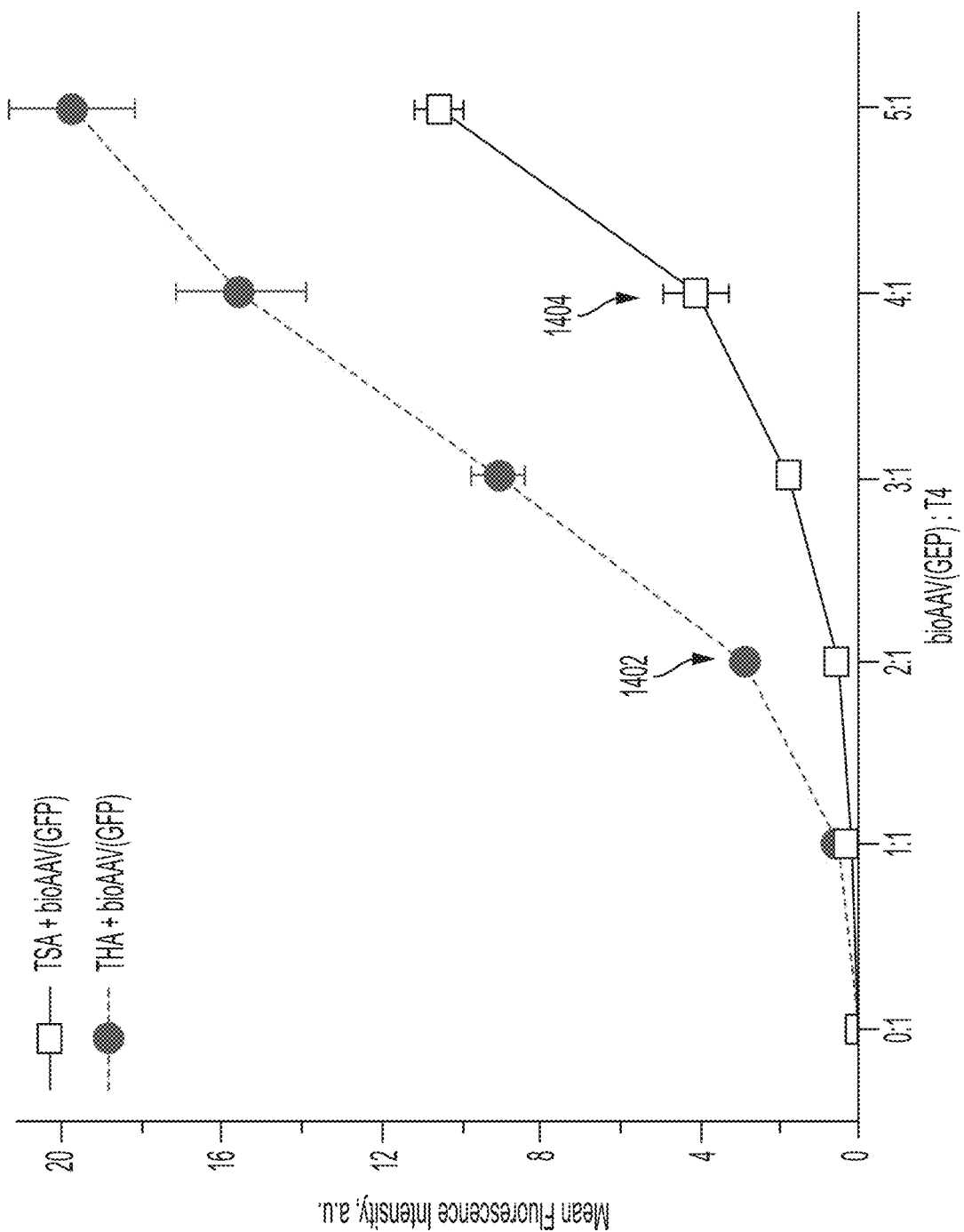
FIG. 14 is a schematic diagram of DNAs packaged in T4 or AAV according to an exemplary embodiment of the present invention.
Figure 15:
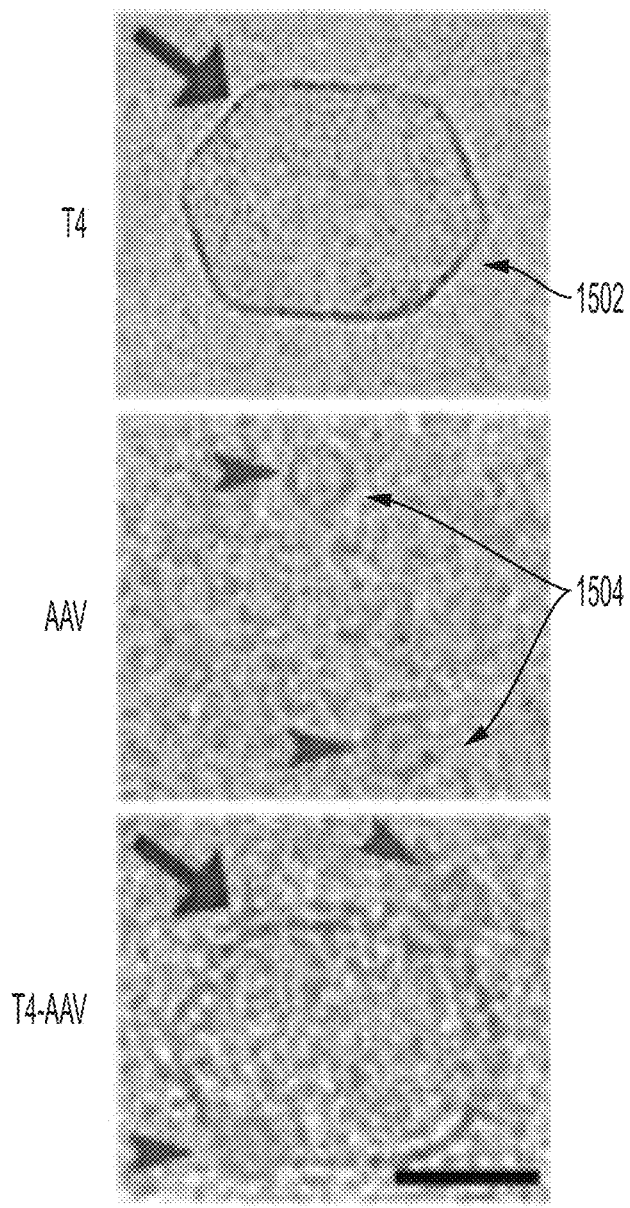
FIG. 15 a graph illustrating how luciferase DNA delivery and expression increase with increasing AAV to T4 ratio using T4(luci)-Soc-AAV particle according to an exemplary embodiment of the present invention.

The conjugation of AAV to T4 is also monitored through the amount of unbound AAV. After increasing ratios of bioAAV(GFP) added to TSA or THA, unbound bioAAV (GFP) is collected and transduced into HEK293 cells to have the GFP gene carried by bioAAV expressed. Thus, the fluorescence intensity is an indication of the amount of GFP expression and the amount of unbound AAV. FIG. 14 shows the quantification of unbound bioAAV GFP expression. The sharp increase of the amount of unbound AAV at points 1402 and 1404 suggests saturated conjugation of AAV to T4. On average, up to four AAV particles are conjugated to one T4 capsid through TSA bridges, while up to two AAV particles are conjugated to one T4 capsid through THA bridges (FIG. 14). Further addition of AAV resulted in the elution of increasing amounts of the virus in the flow-through. The efficient assembly of T4-AAV is also confirmed by transmission electron microscopy (TEM), as shown in FIG. 15. In FIG. 15, the blue arrow shows T4 1502 and the red arrows show the AAV 1504 attached to the surface of T4.

Genes are Remarkably More Efficiently Delivered by T4 when AAV is Attached

It is previously shown that transduction into mammalian cells (HEK293) by T4 heads alone is very inefficient[10]. The present invention compared the delivery efficiency of T4 heads along and T4-AAV when the genes are packaged in T4.

In one embodiment, plasmids containing luminance genes are packaged in T4 capsid with AAV attached through TSA bridges, and delivered to HEK293 cells. The delivery efficiency is measured by relative luminescence unit.

Figure 16:
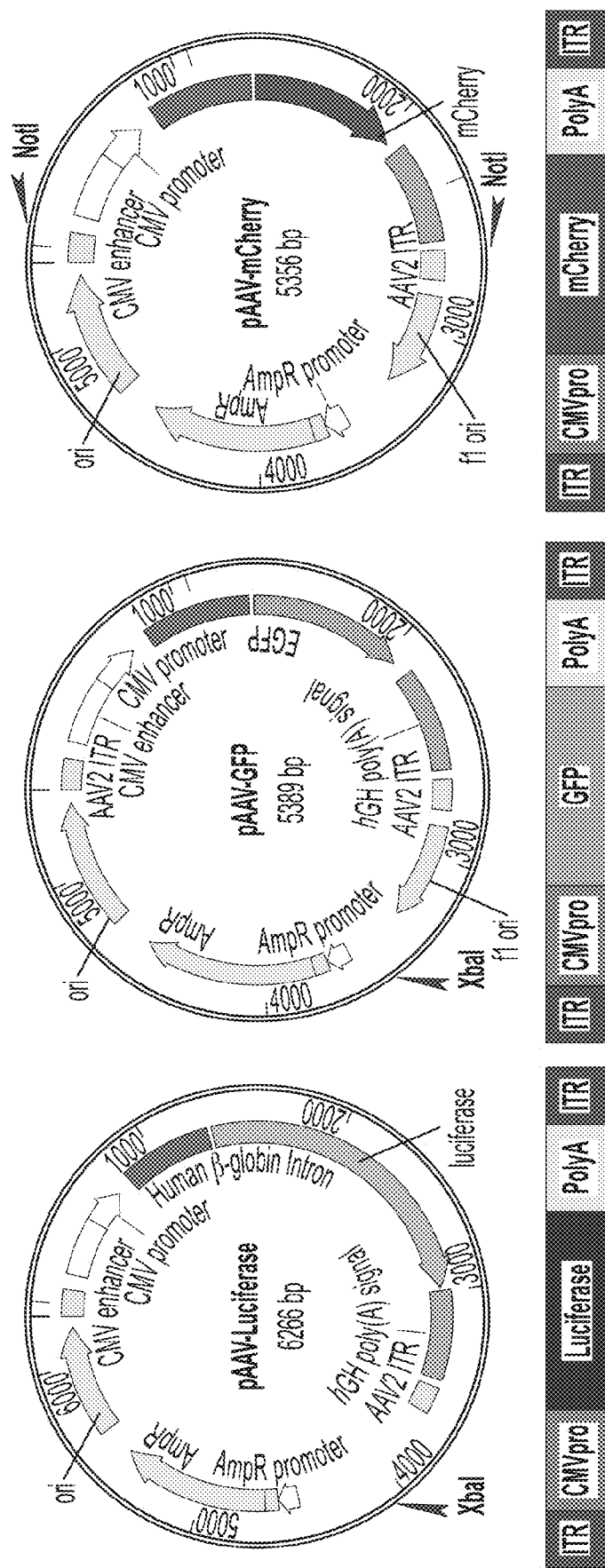
FIG. 16 a graph illustrating how luciferase DNA delivery and expression increase with increasing T4-Soc-AAV to cells ratio according to an exemplary embodiment of the present invention.

As shown in FIG. 16, the nucleic acid packaged into the T4 capsid using the DNA packaging motor comprises three different plasmids containing luciferase (Luci), GFP, or mCherry genes under the control of the CMV promoter.

Figure 17:
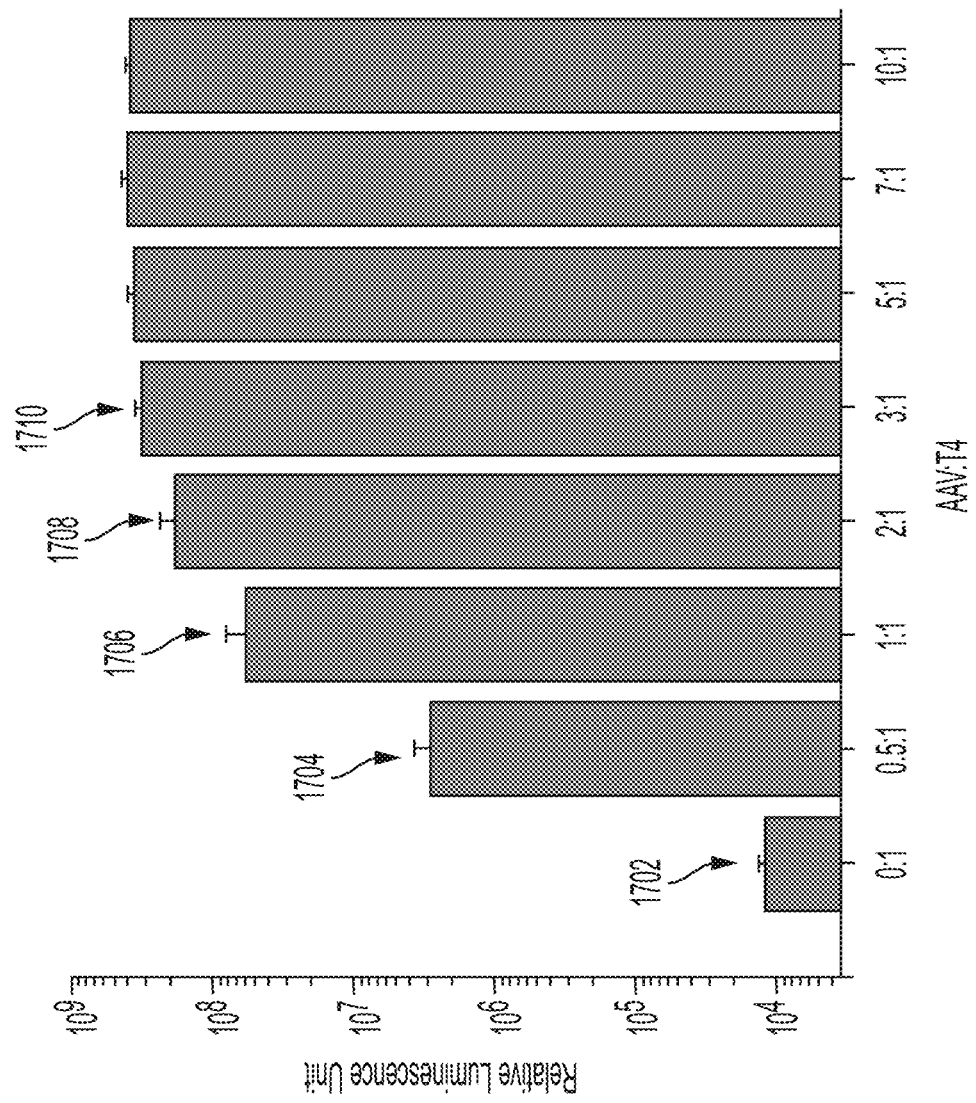
FIG. 17 a graph illustrating the increased luciferase DNA delivery and expression with the attachment of AAV according to an exemplary embodiment of the present invention.
Figure 18:
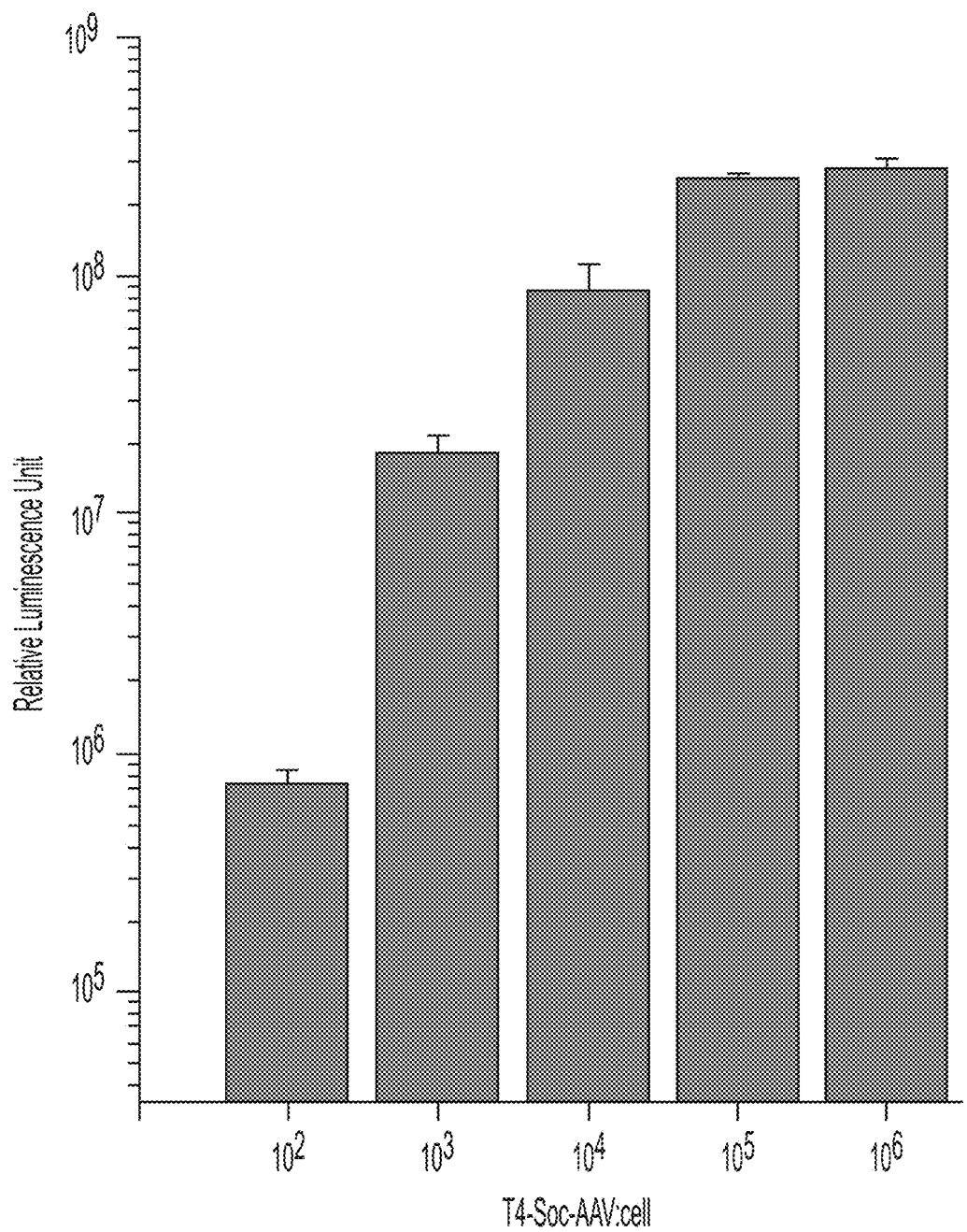
FIG. 18 a graph illustrating how luciferase DNA delivery and expression increase with increasing T4-Hoc-AAV to cells ratio according to an exemplary embodiment of the present invention.

In one preferred embodiment, luciferase DNA is delivered into cells using T4(luci)-Soc-AAV. The delivery efficiency is indicated by relative luminescence unit. FIG. 17 shows the relative luminescence units of T4 head alone 1702 and T4-AAV vector with different ratio of AAV to T4 such as 0.5:1 (1704), 1:1 (1706), 2:1 (1708), and 3:1 (1710). As shown in FIG. 17, attachment to AAV through TSA bridges results in at least 40,000-fold increase in transduction efficiency. Additionally, the delivery efficiency, as indicated by the amount of luciferase activity, is proportional to the number of Soc-bridged T4-AAV particles added per cell, which reached a maximum at $10^5$ particles per cell (FIG. 18).

Figure 19:
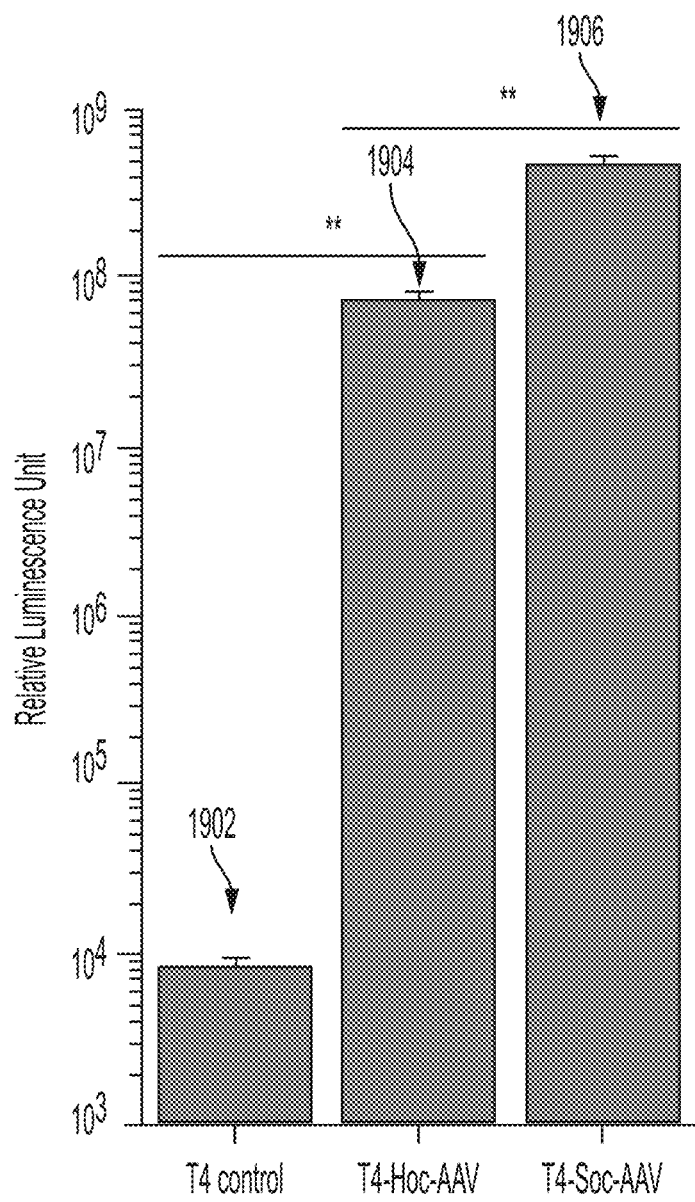
FIG. 19 a micrograph illustrating GFP and mCherry DNA delivery and expression in cells according to an exemplary embodiment of the present invention.
Figure 20:
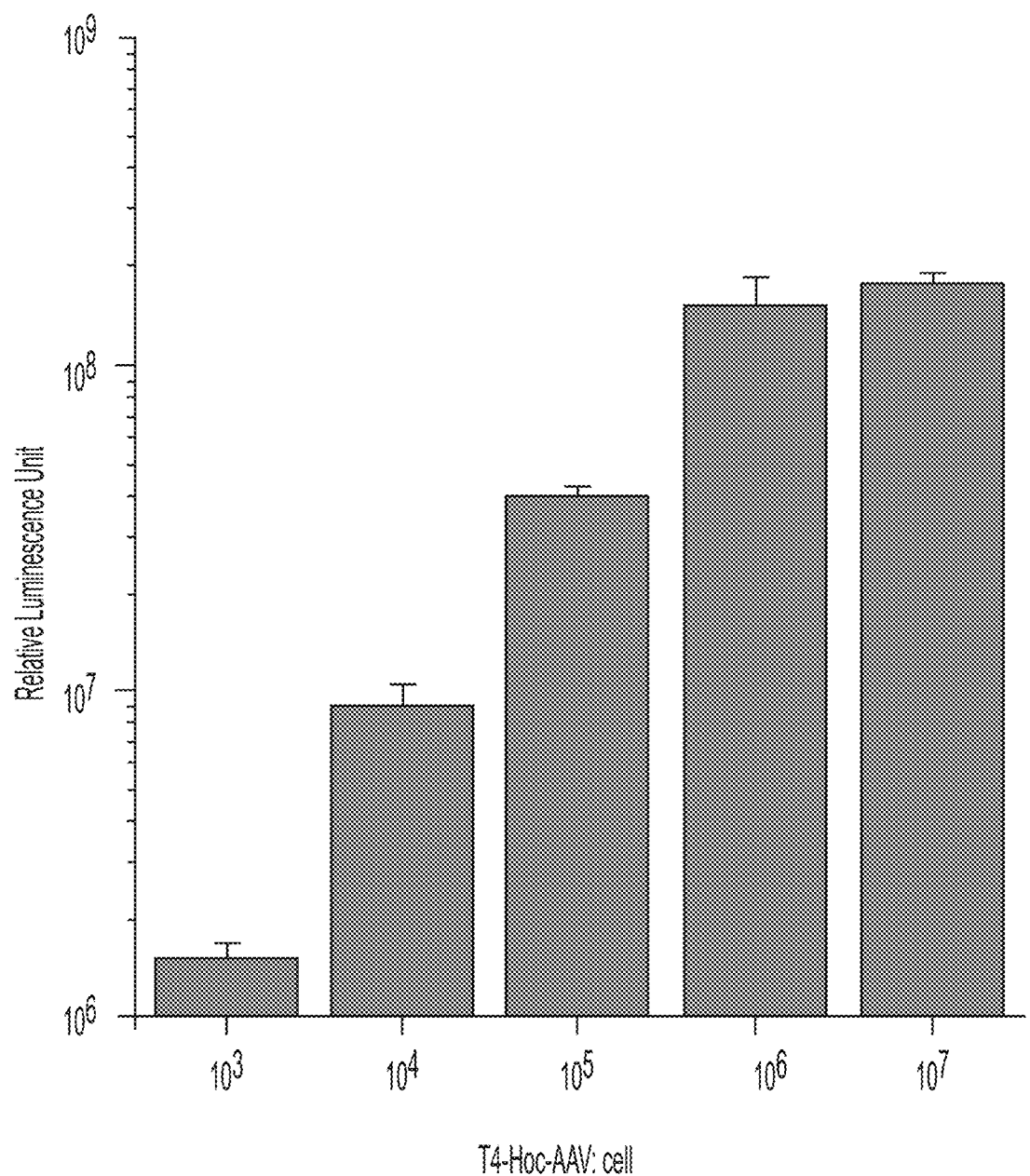
FIG. 20 a schematic diagram of β-gal-Soc-T4(luci)-AAV (GFP) particle according to an exemplary embodiment of the present invention.

In another preferred embodiment, luciferase DNA is delivered into cells using T4(luci)-Hoc-AAV. FIG. 19 shows the relative luminescence units of T4 head alone 1902 and T4-AAV vector bridged by Hoc 1904 and Soc 1906. As shown in FIG. 19, attachment to AAV through HSA bridges results in 10,000-fold increase in transduction efficiency compared to T4 head alone. Additionally, the delivery efficiency, as indicated by the amount of luciferase activity, is also proportional to the number of Hoc-bridged T4-AAV particles added per cell, which reached a maximum at $10^6$ particles per cell (FIG. 20).

Genes are Efficiently Delivered Through Both T4 and AAV

An advantage of the T4-AAV hybrid vector is that both T4 and AAV can be simultaneously used to deliver genes. T4 delivers genes in the form of double-stranded DNA[23], whereas AAV delivers genes in the form of single-stranded DNA, the natural state of the packaged AAV genome[15].

In one embodiment, mCherry DNA (red fluorescence) is packaged into T4 capsid and GFP DNA (green fluorescence) is packaged into AAV, and both are conjugated through the Soc bridges. Then, these T4(mCherry)-AAV(GFP) nanoparticles are added to HEK293 cells for delivery and expression both green and red fluorescence, and the fluorescence signals are evenly distributed throughout the cells (2102 in FIG. 21). Importantly, the signals highly merge, demonstrating the expression of both signals in the same cell because of co-delivery of both the T4-associated mCherry and AAV-associated GFP by the T4-AAV hybrid vector.

Figure 21:
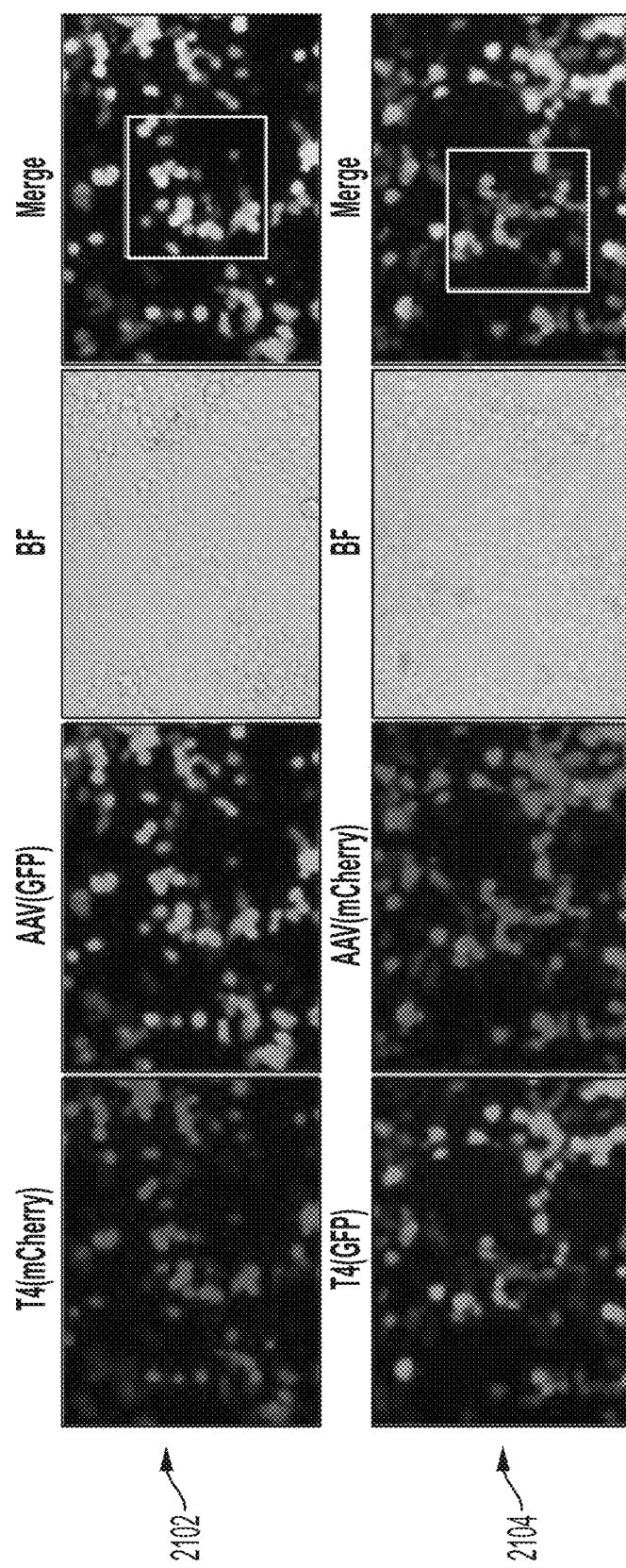
FIG. 21 a graph illustrating how luciferase DNA delivery and expression increase with increasing AAV to T4 ratio using β-gal-Soc-T4(luci)-AAV(GFP) particle according to an exemplary embodiment of the present invention.

In another embodiment, GFP DNA (green fluorescence) is packaged into T4 capsid and mCherry DNA (red fluorescence) is packaged into AAV, which are conjugated also through the Soc bridges, forming the T4(GFP)-AAV (mCherry) particles. after the T4(GFP)-AAV(mCherry) particles are added to HEK293 cells, both green and red fluorescence signals are also evenly distributed and highly merged (2104 in FIG. 21).

In both embodiments, the correlation coefficients of green and red fluorescence signals are quantified using linear Pearson (rp) and nonlinear Spearman's rank (rs). The results show high $r_p$ and $r_s$ values for both (for T4(mCherry)-AAV (GFP): $r_p$=0.881, $r_s$=0.884; for T4(GFP)-AAV(mCherry): $r_p$=0.856, $r_s$=0.902), demonstrating high co-expression of the fluorescence genes delivered by T4 and AAV.

T4-AAV Efficiently Deliver Both Genes and Proteins Simultaneous

The T4-AAV vector is also advantageous for its ability to deliver both proteins and genes, further expanding the therapeutic potential of the hybrid nanoparticle.

Figure 22:
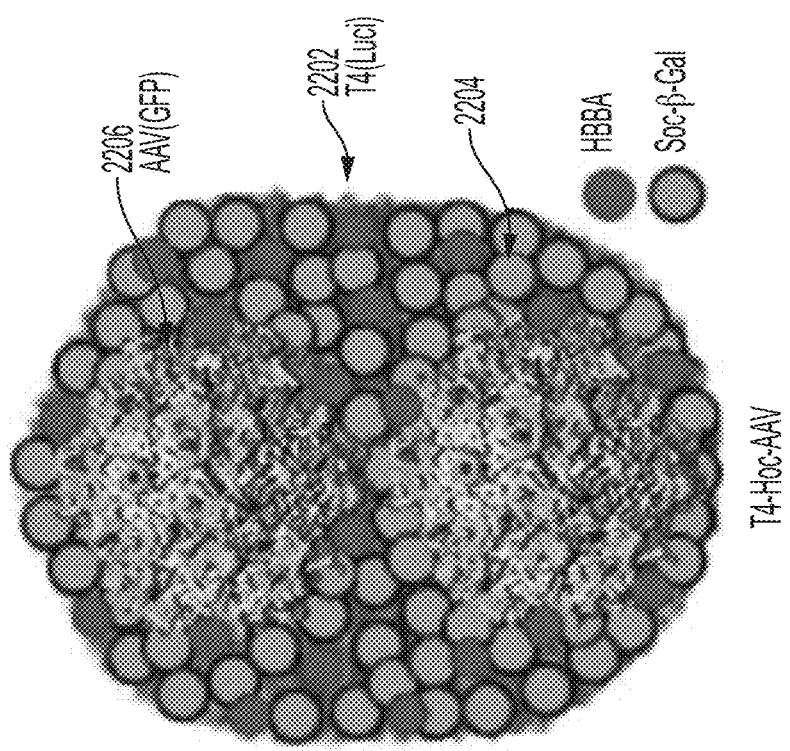
FIG. 22 a graph illustrating how GFP DNA delivery and expression increase with increasing AAV to T4 ratio using β-gal-Soc-T4(luci)-AAV(GFP) particle according to an exemplary embodiment of the present invention.

In one embodiment, approximately 250 copies the 116 kDa β-galactosidase from E. coli fused to Soc (Soc-β-gal) 2204 are displayed on the T4 head 2202; ~9 molecules of ~6.2 kb luciferase plasmid (not shown) are packaged in T4 head 2202; GFP DNA (not shown) is packaged in AAV 2206, which attached to T4 through Hoc bridges (FIG. 22). The resultant (β-gal-Soc-T4(luci)-AAV(GFP) particles are transduced into HEK293 cells.

Figure 23:
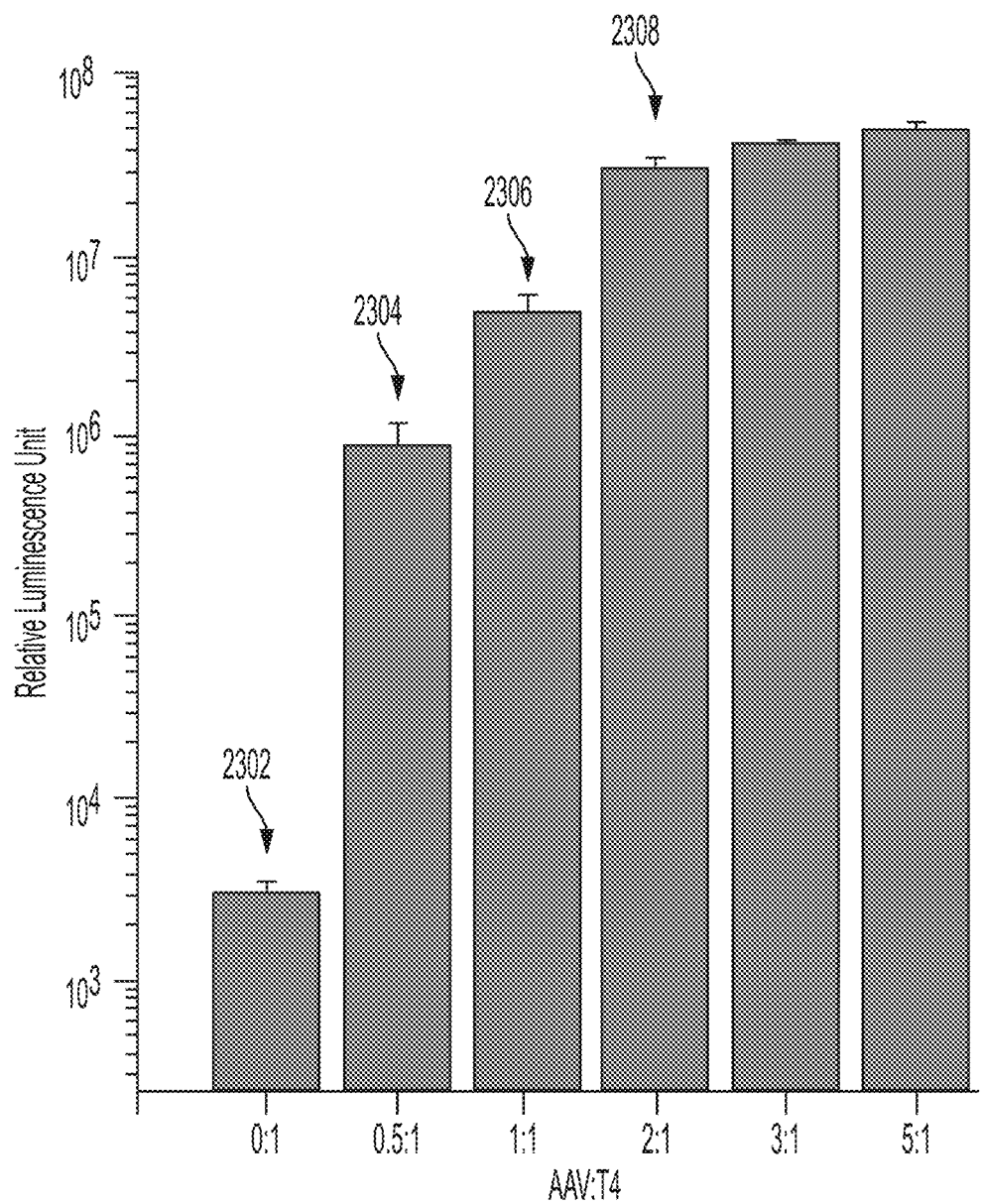
FIG. 23 a graph illustrating how β-galactosidase protein delivery increases with increasing Soc-β-gal to T4-HocAAV ratio using β-gal-Soc-T4(luci)-AAV(GFP) particle and how the attachment of AAV enhances β-galactosidase protein delivery according to an exemplary embodiment of the present invention.

FIG. 23 shows the relative luminescence unit, which is an indication of delivery efficiency, as a result of the luciferase delivery by T4 head alone 2302, and β-gal-Soc-T4(luci)-AAV(GFP) particles with different ratio of AAV to T4 such as 0.5:1 (2304), 1:1 (2306) and 2:1 (2308). As shown in FIG. 23, attachment to AAV through HSA bridges results in 10,000-fold increase in transduction efficiency compared to T4 head alone.

Figure 24:
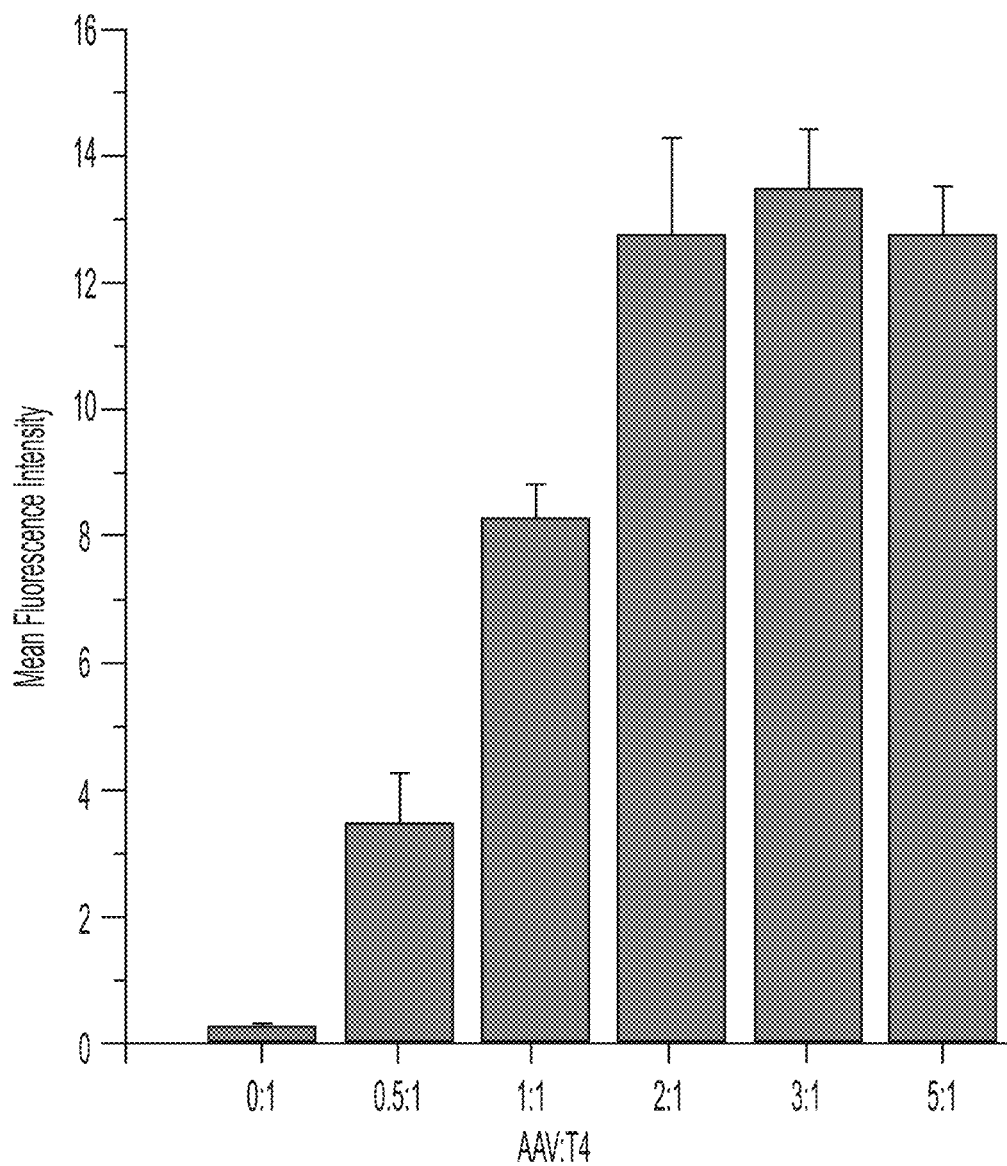
FIG. 24 a micrograph illustrating the delivery of GFP and NLS-GFP proteins and the delivery and expression of mCherry DNA using GFP-T4(mCherry)-AAV and NLS-GFP-T4(mCherry)-AAV particles according to an exemplary embodiment of the present invention.

In FIG. 24, the expression of AAV-associated GFP shows a clear dose dependence on the ratio of AAV to T4 and peaks at the ratio of 3:1.

Figure 25:
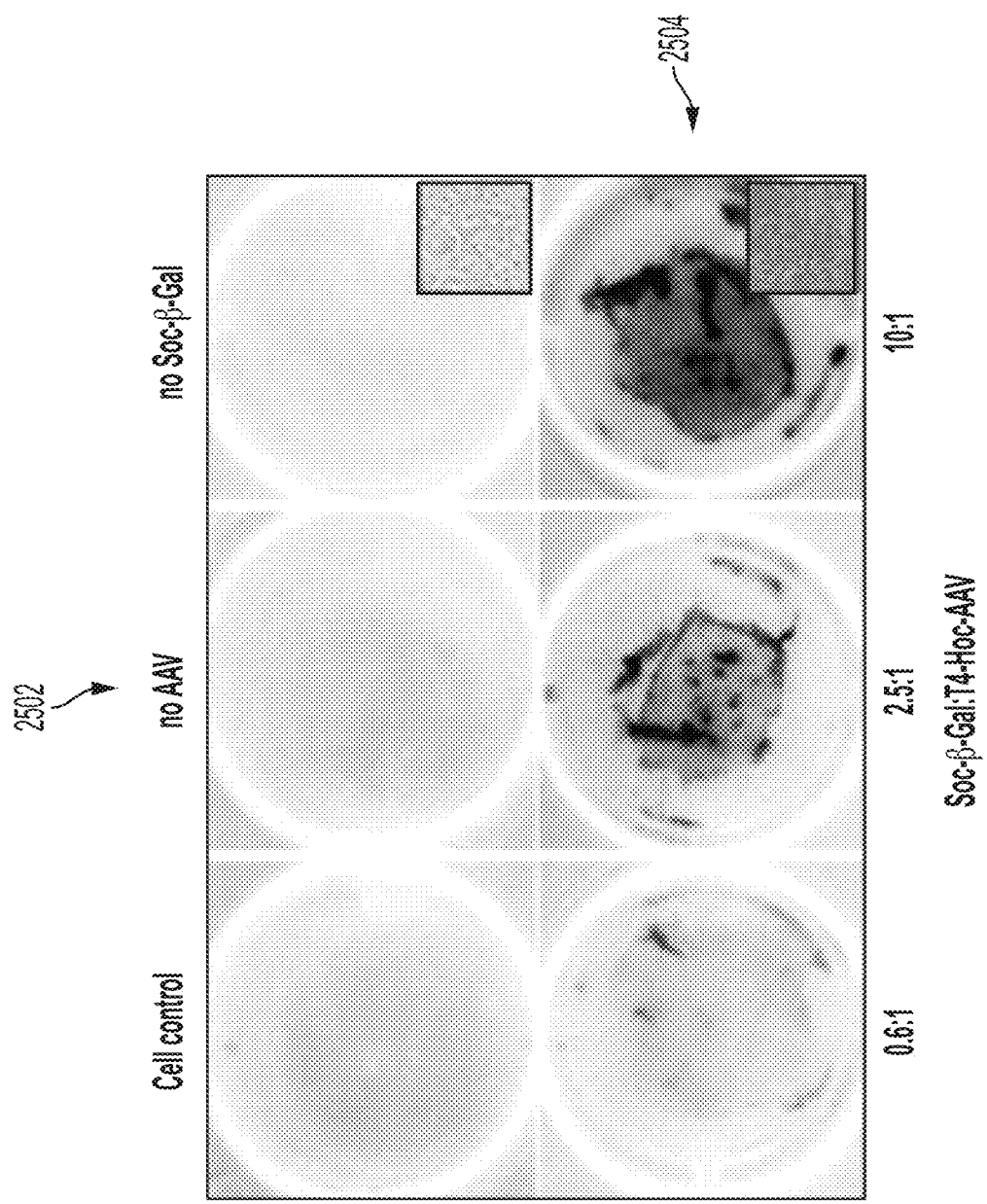
FIG. 25 a schematic diagram of ITRs-Luci DNA packaged in T4 or AAV according to an exemplary embodiment of the present invention.

The expression of β-galactosidase enzyme delivered by T4 is tested using X-Gal substrate. The appearance of the blue color of the cleaved X-Gal substrate indicates the successful expression of the functional β-galactosidase enzyme. FIG. 25 shows the intensity of the blue color, when delivered by T4 head alone 2502 and R-gal-Soc-T4(luci)-AAV(GFP) particles with different ratio of Soc-β-gal to T4-Hoc-AAV 2504. As shown in FIG. 25, the intensity of the color is proportional to the copy number of the displayed Soc-β-gal protein. The result confirms that the attachment of AAV also leads to enhanced delivery of proteins displayed on the surface of T4.

Figure 26:
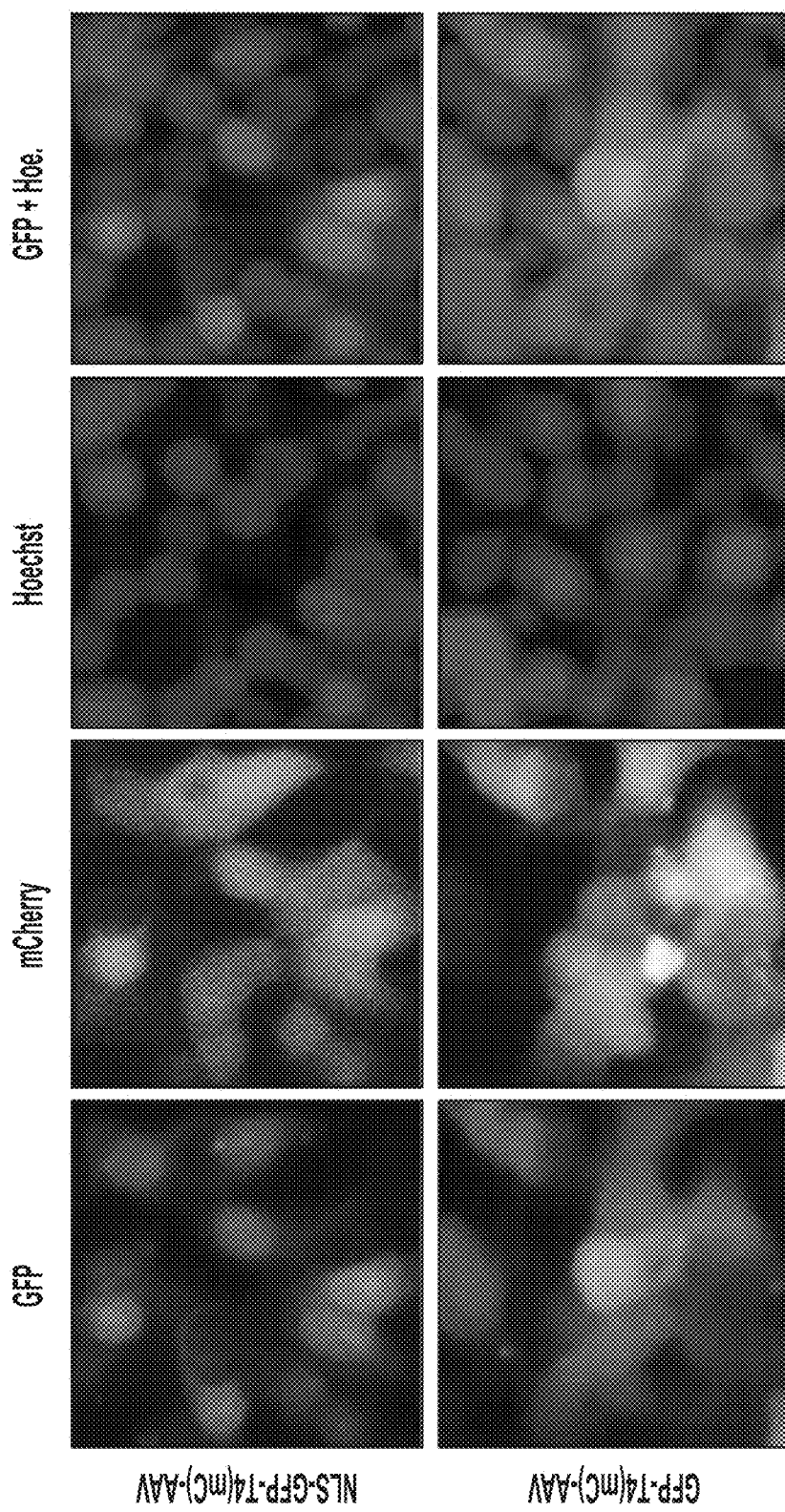
FIG. 26 an image of ITRs-Luci DNA delivery and expression in mice showing that AAV enhanced the delivery and in vivo persistence of the packaged DNA according to an exemplary embodiment of the present invention.

In another embodiment, the T4 capsid was displayed with either GFP or GFP fused to the nuclear localization signal (NLS), packaged with mCherry plasmid DNA and attached to AAV. These T4-AAV nanoparticles were then transduced into HEK293 cells. As shown in FIG. 26, the green fluorescence signal and mCherry signal are detected in both GFP-T4(mCherry)-AAV and NLS-GFP-T4(mCherry)-AAV transduced cells, confirming the efficient delivery of both proteins and genes by T4-AAV particles.

Furthermore, no measurable impact on cell viability was observed following transduction by T4-AAV particles, whether Soc-bridged or Hoc-bridged, even when added to a level of $10^6$ T4-AAV vectors per cell.

Replacing AAV with a Variant Lead to Failure in Enhancing Delivery Efficiency

Figure 27:
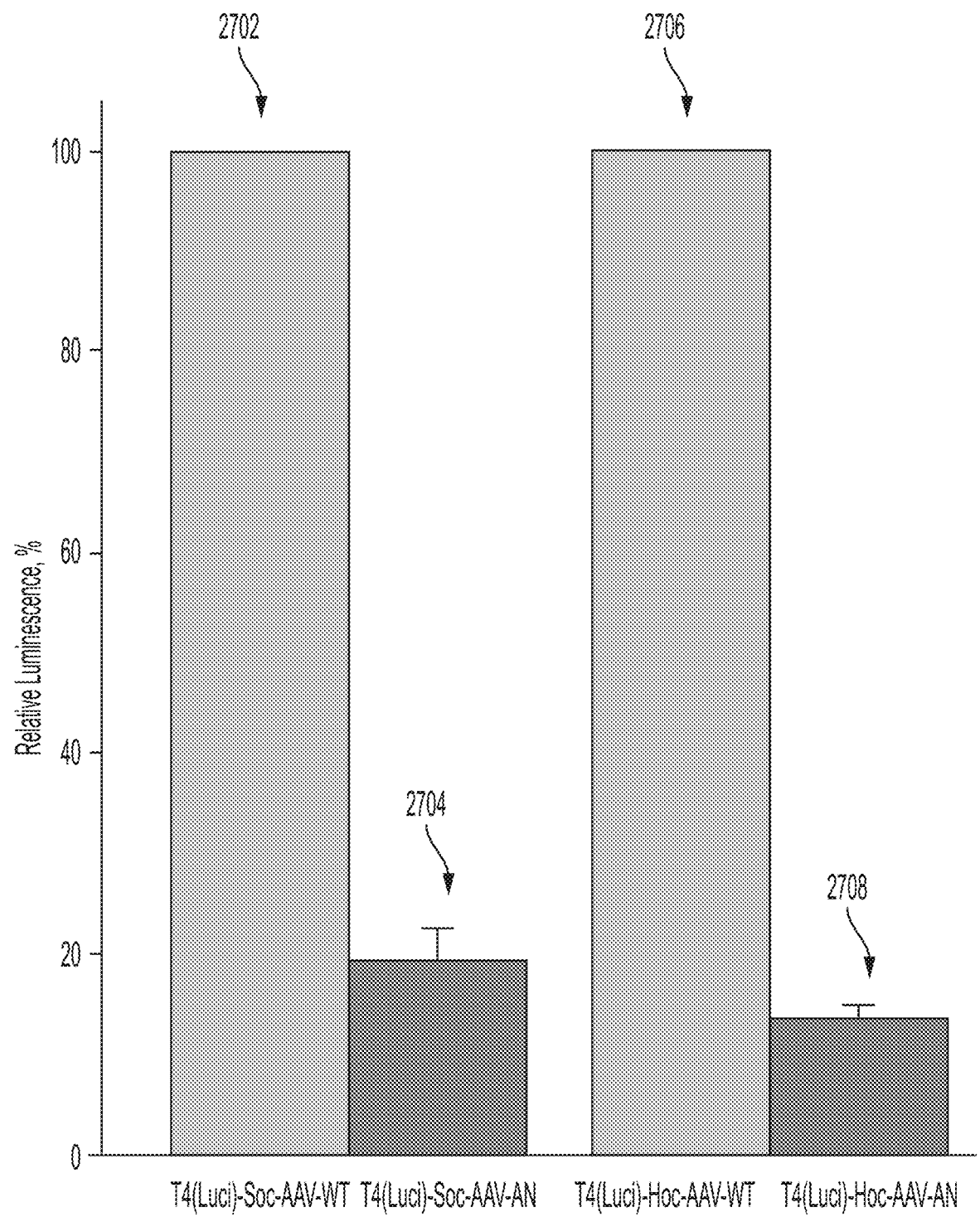
FIG. 27 a graph showing the delivery and expression and in vivo persistence of ITRs-Luci DNA in mice according to an exemplary embodiment of the present invention.

In one embodiment, a phospholipase A2 (PLA2) of AAV VP1 capsid protein is mutated, producing AAV-PLA2 mutant. The T4-AAV nanoparticles are assembled by attaching the AAV-PLA2 mutant to T4 either through SBA bridges or through HBBA bridges. Luciferase DNA is packaged in T4, producing the T4(Luci)-Soc-AAV-AN and T4(Luci)-Hoc-AAV-AN hybrid vectors, and delivered to HEK293 cells. FIG. 27 shows the relative luminescence of T4(Luci)-Soc-AAV-AN 2704 and T4(Luci)-Hoc-AAV-AN 2708, compared with T4(Luci)-Soc-AAV-WT 2702 and T4(Luci)-Hoc-AAV-WT 2706, which do not have the PLA2 mutation. The results confirm that the T4-AAV with wild-type AAV is at least 5-fold more efficient than T4-AAV with PLA2 mutant in delivery genes packaged in T4. In other words, T4(Luci)-Soc-AAV-AN (contain PLA2 mutation) preserves 20% of transduction efficiency of T4(Luci)-Soc-AAV-WT, and is therefore still more efficient in delivering nucleic acid than T4 head alone.

Figure 28:
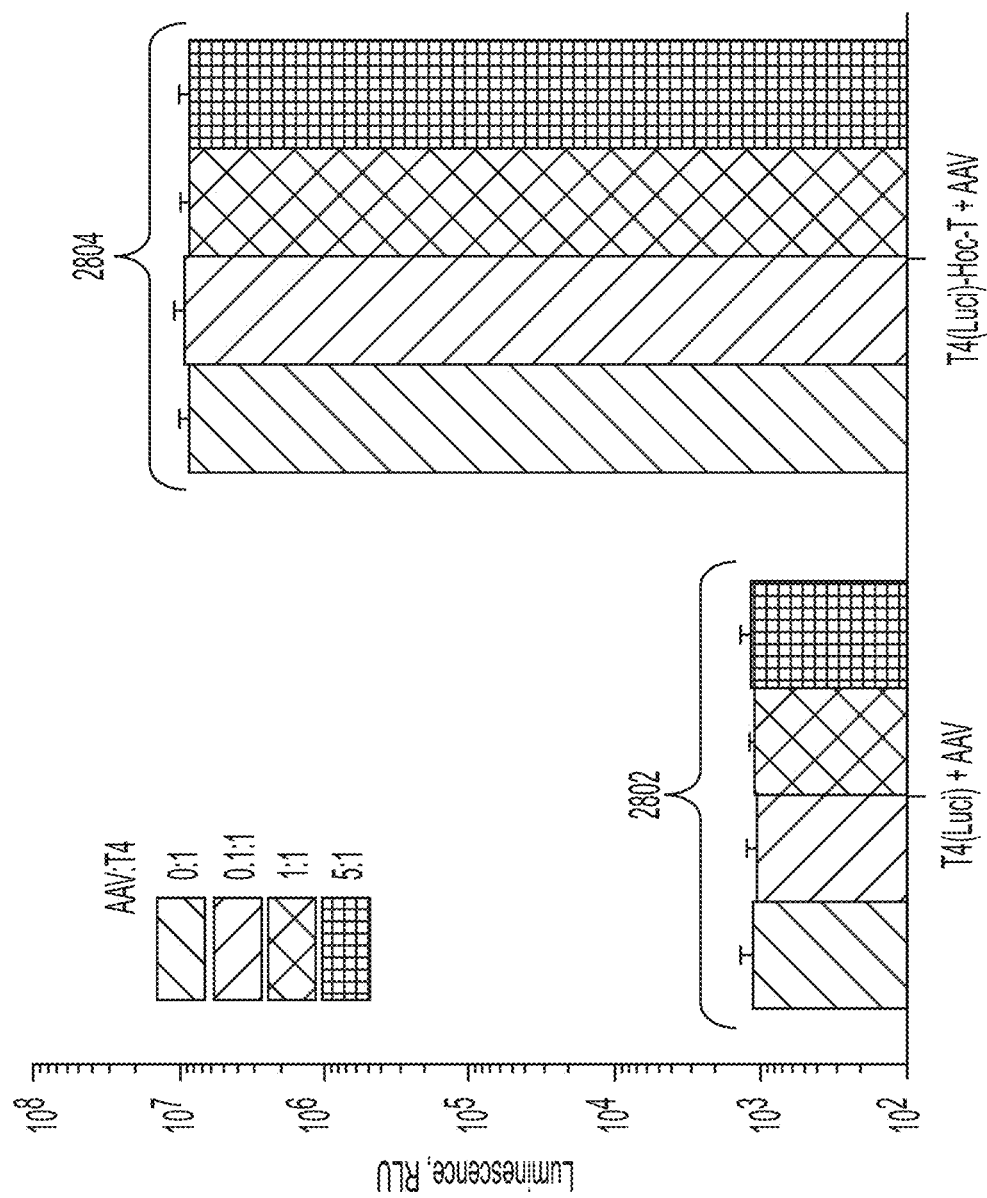
FIG. 28 an image of ITRs-Luci DNA delivery and expression in mice with reduced dose of T4-AAV showing that AAV enhanced the delivery and in vivo persistence of the packaged DNA according to an exemplary embodiment of the present invention.

Absence of Biotin-Avidin Cross Bridge Leads to Failure in Enhancing Delivery Efficiency In one embodiment, T4 is mixed with AAV without binding by biotin-avidin cross bridge. Then, luciferase DNA is packaged in T4 and delivered to HEK293 cells. FIG. 28 shows the relative luminescence unit of T4 and AAV mixture 2802, at different T4 to AAV ratio. In the absence of biotin-avidin cross bridge, the result confirms no enhancement of T4 delivery compared to T4 alone. The attachment of peptide T improves the delivery of Luci gene by T4. However, the addition of AAV to the mixture also does not further improve the delivery efficiency of T4(Luci)-Hoc-T at different T4 to AAV ratios 2804.

According to the above embodiments, the working ratio ranges and optimal ratios at each step of T4-AAV hybrid vector production is summarized in the table below:

|  | Working range of ratio | Optimal ratio |
| --- | --- | --- |
| Biotin:Soc | 1:1 to 30:1 | 20:1 |
| Soc-biotin:T4 | 0.5:1 to 40:1 | 30:1 |
| Avidin:T4-Soc-biotin | 0.5:1 to 10:1 | 2:1 |
| Biotin:Hoc-BAP | 1:1 to 20:1 | 10:1 |
| Avidin:HBB | 1:1 to 10:1 | 3:1 |
| HBBA:T4 | 1:1 to 40:1 | 30:1 |
| Biotin:AAV | 10:1 to 40:1 | 20:1 |
| BioAAV:TSA | 1:1 to 5:1 | 4:1 |
| BioAAV:THA | 1:1 to 5:1 | 2:1 |
| DNA:T4 | 1:1 to 40:1 | 20:1 |

Efficient In Vivo Gene Delivery by T4-AAV Nanoparticles

In addition to high delivery efficiency, long in vivo persistence is another desired feature of viral vectors. Upon its entry into nucleus, the single stranded AAV genome replicates to produce a double-stranded AAV DNA. The double-stranded AAV DNA is thought to be converted to head-to-tail concatemers via intra- or inter-molecular recomposition at the ITRs and persist as episomes for long-term transgene expression. Studies on various AAV transduced tissues including liver and muscle have shown that the concatemers persist for a long period of time, up to 22 months[15, 26]. Previous studies also have shown that the ITRs significantly enhanced the in vivo persistence of T4-packaged DNAs[10].

In one embodiment, the AAV inverted terminal repeats (ITRs) is engineered to flank the transgene of packaged DNAs.

Figure 29:
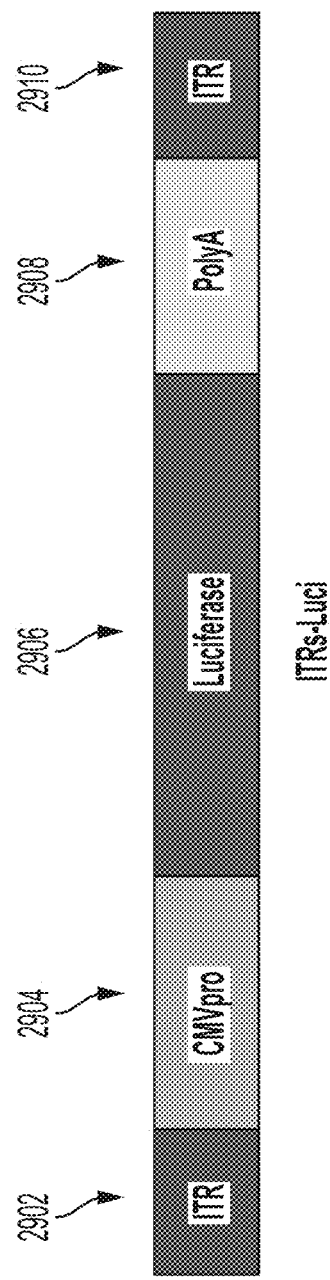
FIG. 29 a graph showing the delivery and expression and in vivo persistence of ITRs-Luci DNA in mice with reduced dose of T4-AAV according to an exemplary embodiment of the present invention.

In a preferred embodiment, the transgene is ~9 ITR-Luci DNA molecules packaged in T4 head, which is attached to AAV either through Soc or Hoc cross-bridges. The resulting T4(ITRs-Luci)-Soc/Hoc-AAV(GFP) particles are then injected into mice. As shown in FIG. 29, the sequences consisting of ITR-Luci DNA molecule are connected in the following order: ITR 2902, CMV promoter (CMVpro) 2904, luciferase gene 2906, poly A 2908, and ITR 2910.

In one embodiment, ~2×$10^{11}$ T4(ITRs-Luci)-Soc/Hoc-AAV(GFP) particles are injected into mice intramuscularly (i.m.). The expression of luciferase in mice is monitored by whole-body imaging and quantified by measuring photon flux for 60 days.

Figure 30:
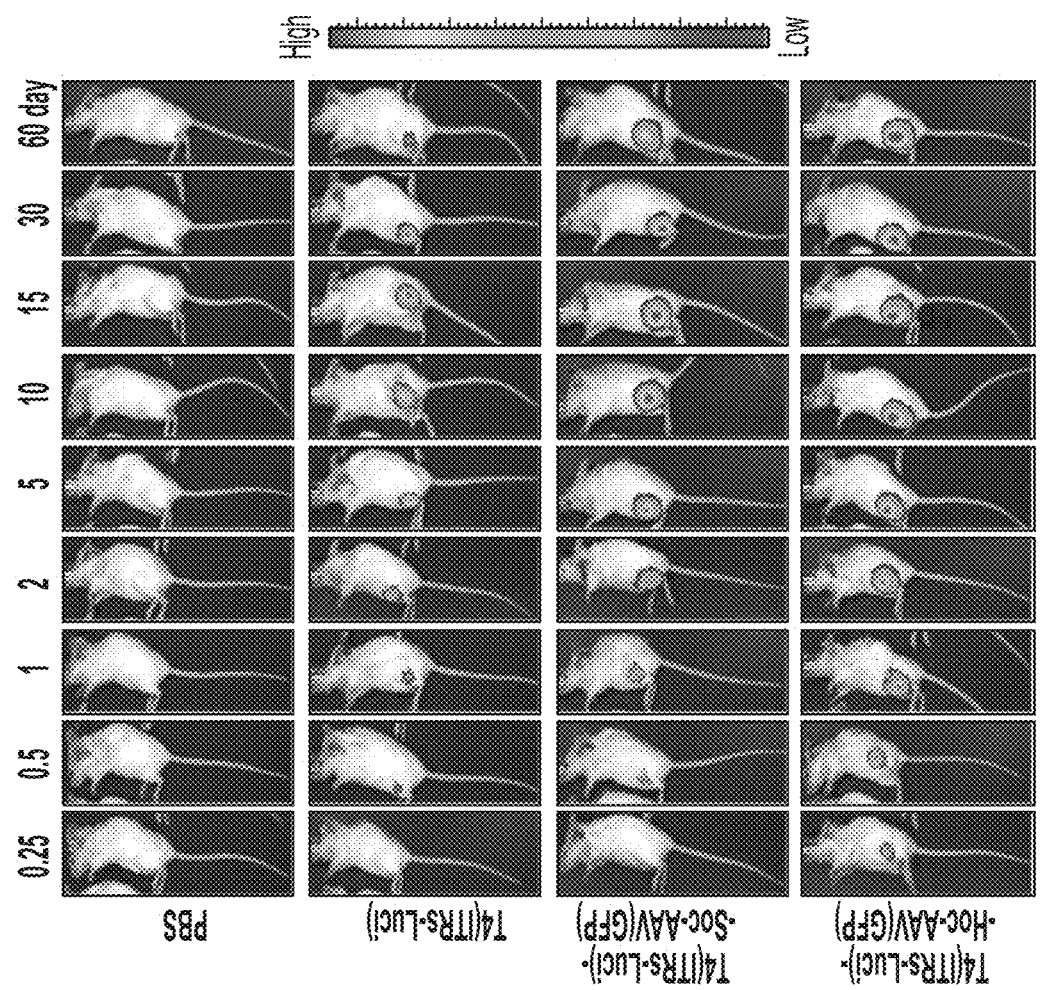
FIG. 30 a schematic diagram of ITRs-HA4900 DNA packaged in T4 or AAV according to an exemplary embodiment of the present invention.
Figure 31:
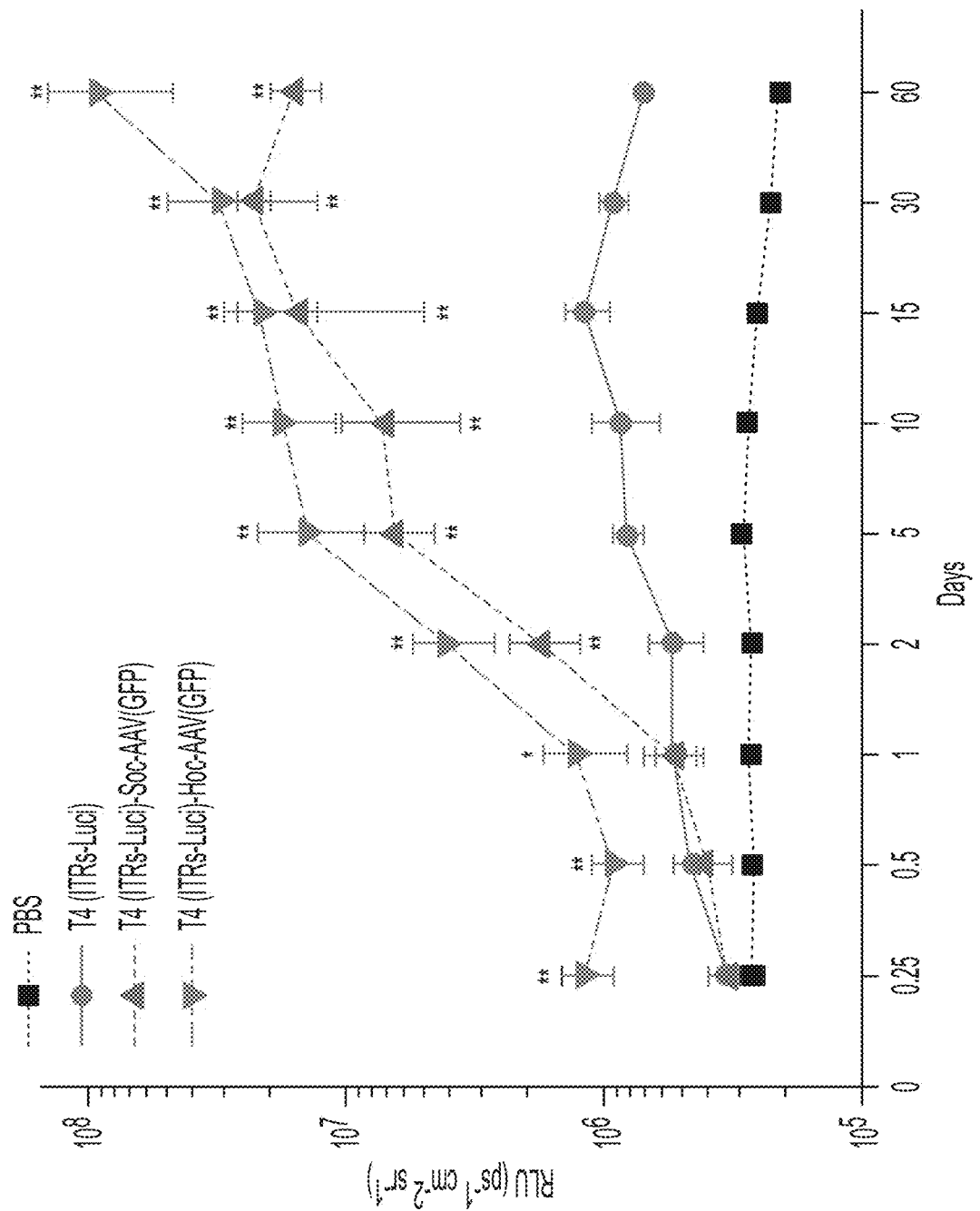
FIG. 31 a graph showing the delivery and expression of HA4900 DNA packaged in T4 according to an exemplary embodiment of the present invention.

As shown in FIG. 30, the luciferase signals are detectable at the local injection site, confirming a single injection of T4-AAV nanoparticles resulted in efficient and prolonged expression of luciferase in mice. T4-Soc-AAV particles resulted in ~25-fold enhancement of the luciferase signal on Day 30 when compared with T4 particles lacking AAV (FIGS. 30 and 31). The signal reached a peak at day 30 and retained at a high level even on day 60. By contrast, the signal reached a peak at day 15 and nearly disappeared by day 60 in mice that received T4 particles lacking AAV (FIGS. 30 and 31). The Hoc-bridged T4-AAV particles generated pronounced luciferase signals that is-130-fold higher than T4 lacking AAV on Day 60.

Figure 32:
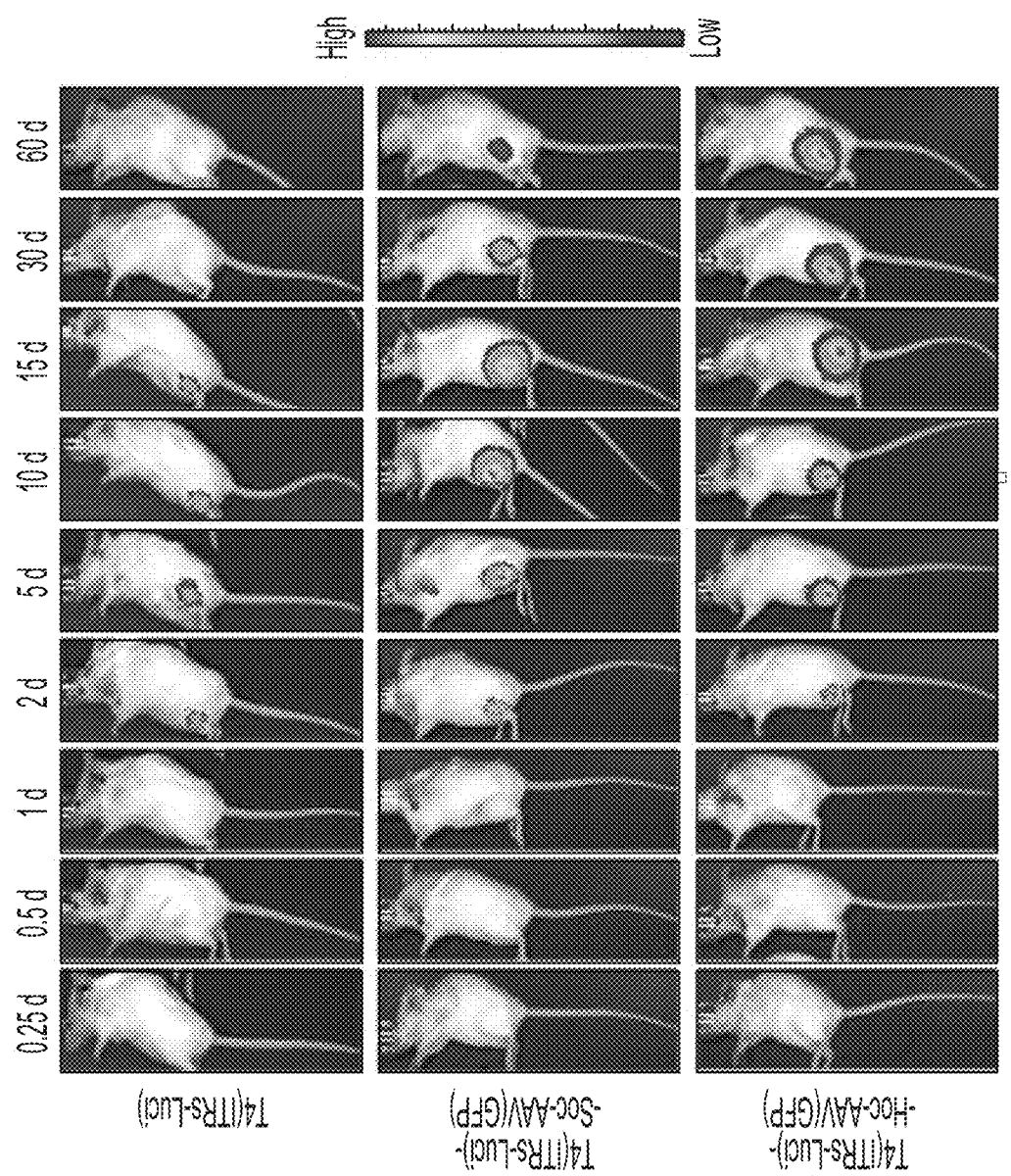
FIG. 32 a graph showing the attachment of AAV to TSA according to an exemplary embodiment of the present invention.
Figure 33:
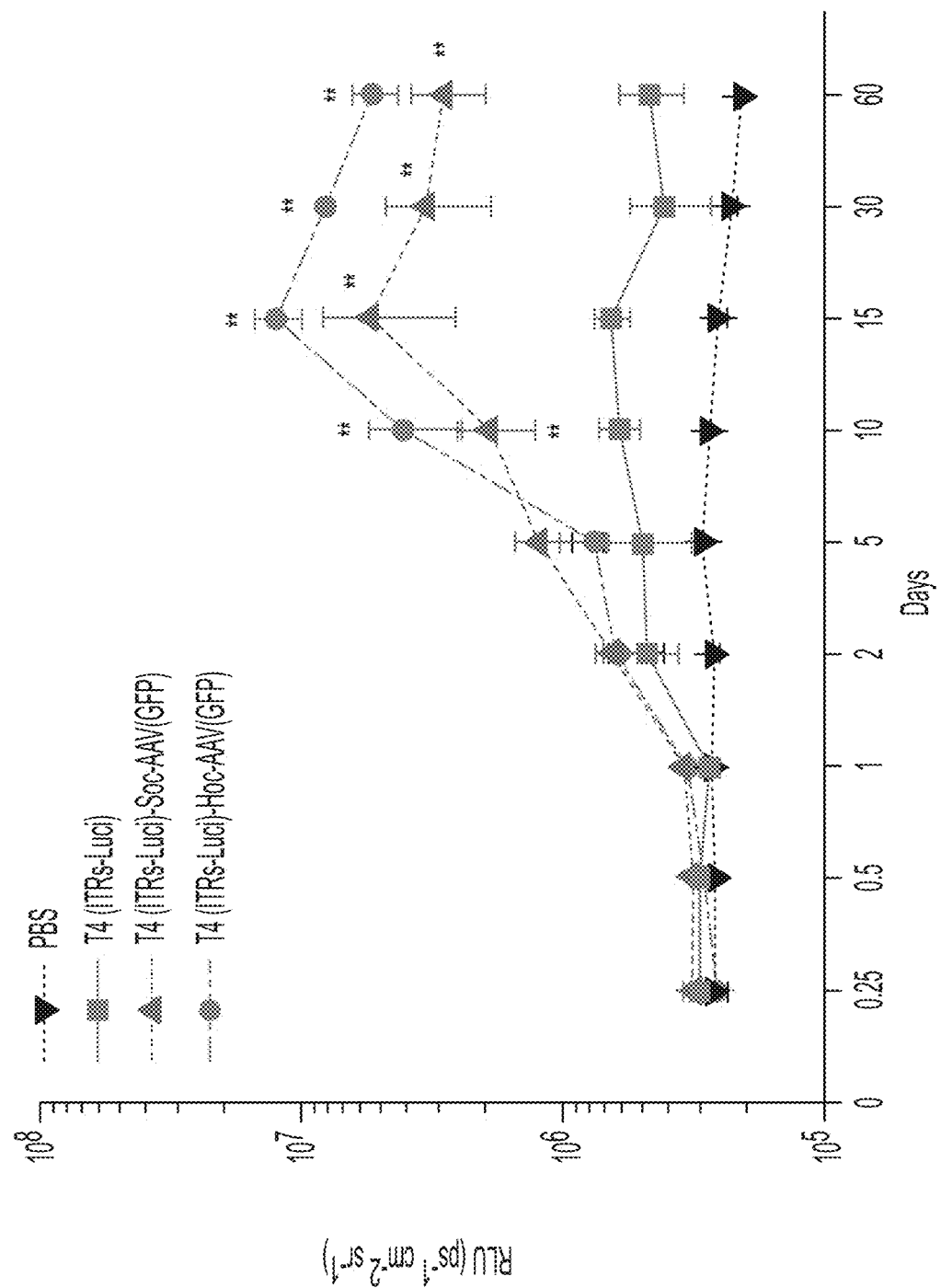
FIG. 33 a graph showing the attachment of AAV to THA according to an exemplary embodiment of the present invention.

In one embodiment, ~5×10$^{11}$ T4(ITRs-Luci)-Soc/Hoc-AAV(GFP) particles are injected into mice intramuscularly (i.m.). The results also confirmed that the conjugated T4-AAV facilitated more efficient delivery of T4 cargo into mice cells resulting in enhanced gene expression for a longer period when compared to T4 alone (FIGS. 32 and 33). The T4-AAV hybrid vector might therefore provide an attractive strategy for therapeutic applications.

Multivalent DNA Vaccine and Protein Antigen Delivered by T4-AAV Efficiently Induced Protective Immune Responses DNA vaccines are attractive candidates for vaccine development due to their overall safety and facile production. Formulating DNA vaccines to protect the DNA from degradation and developing efficient delivery technology play a key role in the final efficacy of DNA vaccines[29]. Additionally, the immune responses elicited by DNA vaccine were dramatically enhanced by a homologous protein boost[30]. Thus, in the present invention, T4-AAV hybrid vector, which can efficiently deliver both DNA and proteins and can also sustain the expression of the delivered genes up to 60 days, is used as a multifunctional genetic and protein (prime-boost) vaccine delivery platform.

Influenza virus is the pathogen causing flu. The hemagglutinin (HA) "stem" region of the influenza virus envelope protein is a very attractive "universal" vaccine candidate[31].

Figure 34:
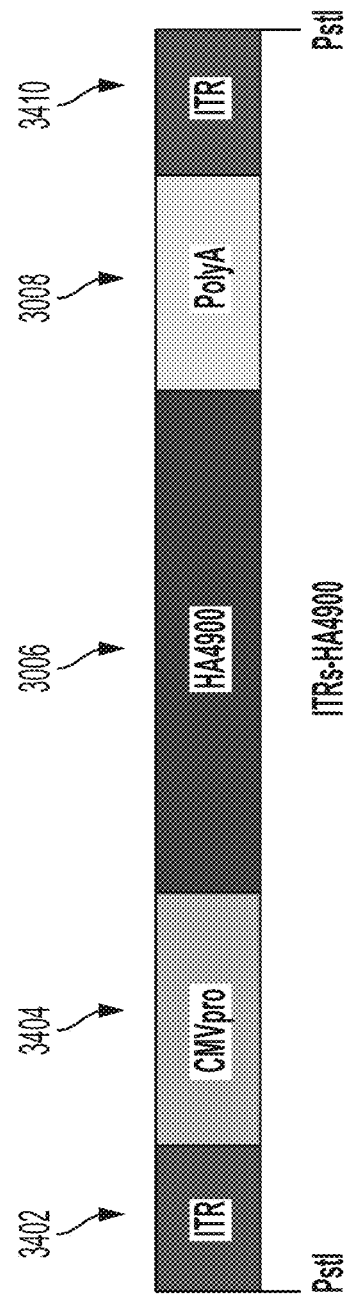
FIG. 34 a graph comparing the delivery efficiency of luciferase DNA packaged in T4 with either wild type AAV or AAV with PLA2 mutation bridged wither by Soc or Hoc according to an exemplary embodiment of the present invention.
Figure 35:
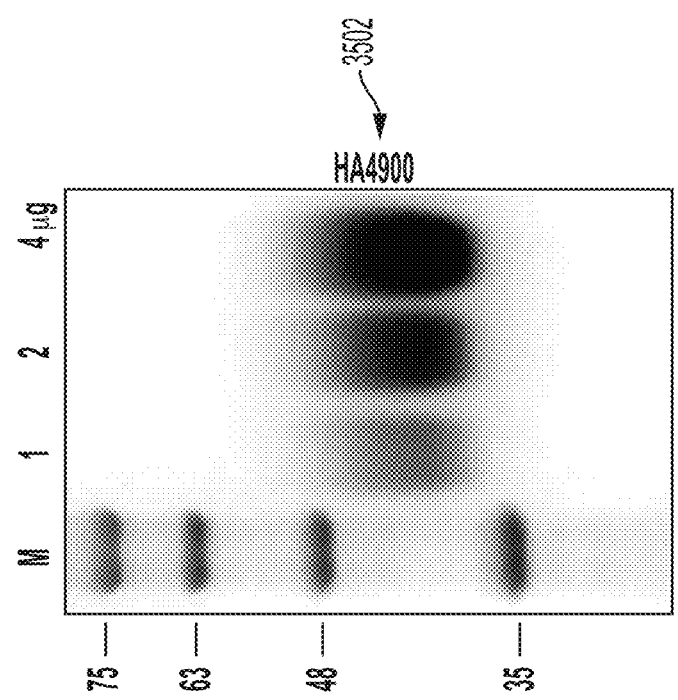
FIG. 35 a graph showing the delivery efficiency of luciferase DNA packaged in T4 with AAV mixed but not attached according to an exemplary embodiment of the present invention.

In one embodiment, the present invention provides a T4-AAV delivery vector containing the HA-stem (HA4900). This DNA was packaged into T4 heads at ~10 molecules per capsid at a packaging ratio of 30:1. As shown in FIG. 34, the packaged DNA molecule contains sequences in the following order: ITR 3402, CMV promoter 3404, HA4900 3406, poly A 3408, and ITR 3410. Transduction of these particles into HEK293 cells results in efficient expression and secretion of the HA4900 antigen into the culture medium (FIG. 35). In FIG. 35, row 3502 shows that HA4900 protein is recovered from cell culture media.

In one embodiment, mice are immunized i.m. with ~2×10$^{11}$ Hoc-bridged T4(HA4900)-AAV(VRC01) particles using a prime-boost scheme without any external adjuvant. VRC-HIVMAB060-00-AB (VRC01) is a broadly neutralizing HIV-1 monoclonal antibody (mAb) isolated from the B cells of an HIV-infected patient. The transduction of VRC01 can also be detected in mice (data not shown), indicating the capability of T4-AAV hybrid vector to package and deliver two different genes.

Figure 36:
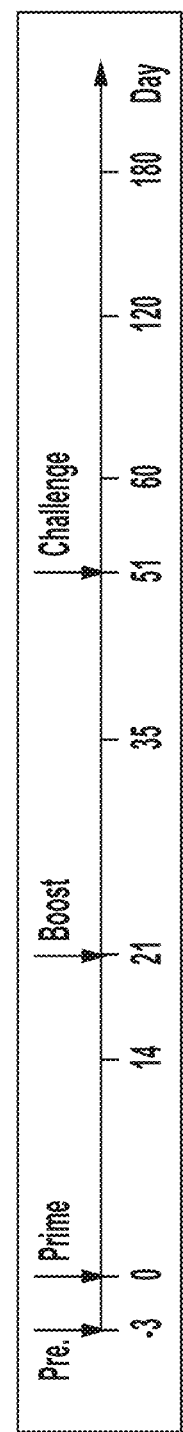
FIG. 36 a graph showing the prime-boost scheme according to an exemplary embodiment of the present invention.

FIG. 36 shows the experimental design of prime-boost scheme. Briefly, 21 days after the prime injection, the mice receive the boost injection. In some embodiments, the mice are also challenged with Yersinia pestis (Y. pestis) CO92 on Day 51. To evaluate the immune responses induced by injection of T4-AAV particles carrying pathogen DNA, IgG titers are measured. In mice, the IgG2a titers reflect TH1 (type 1 T helper cells) immune responses whereas the IgG1 titers reflect TH2 (type 2 T helper cells) immune responses.

Figure 37:
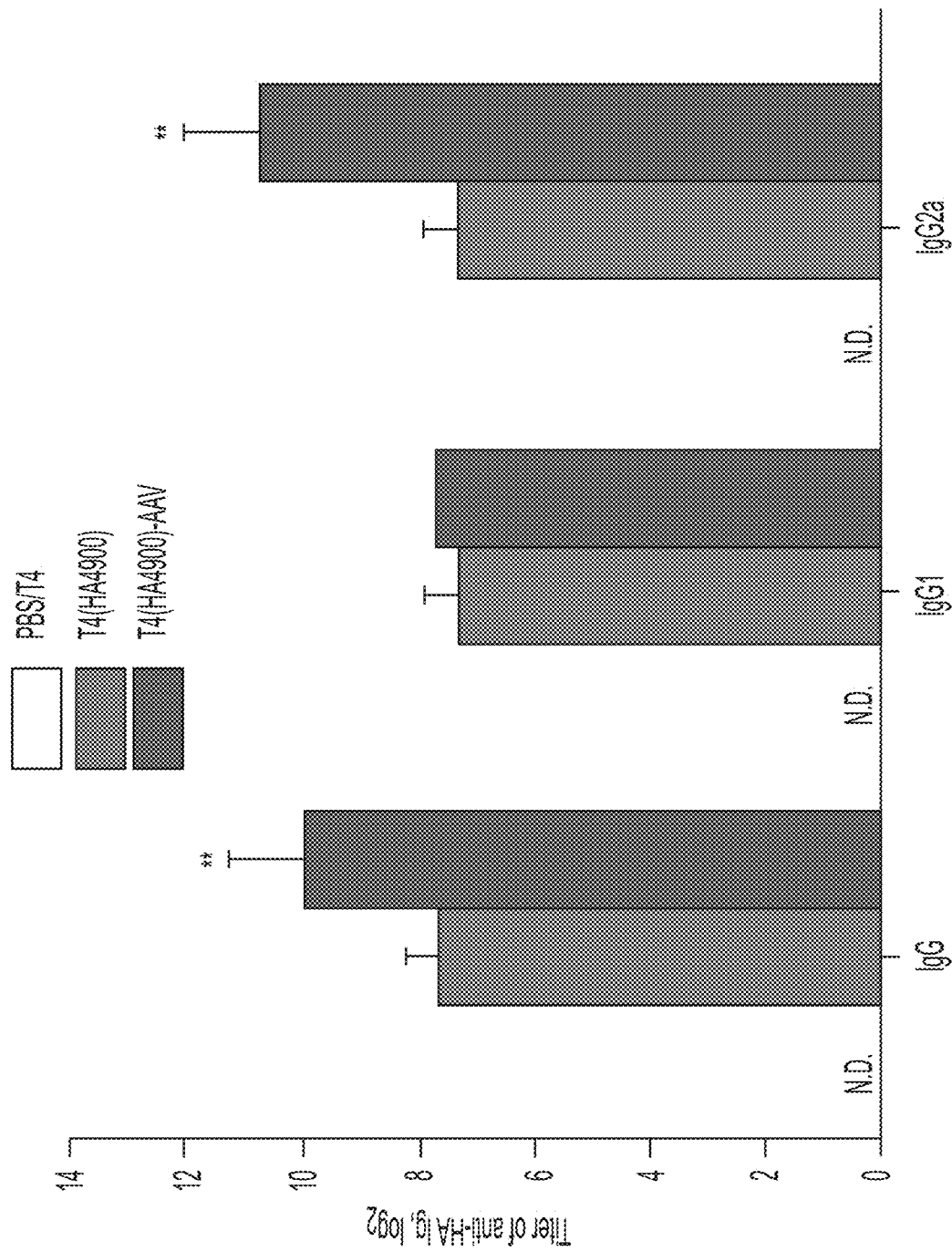
FIG. 37 a graph showing the anti-HA IgG titer on Day 14 induced by T4(HA4900) with or without AAV attached according to an exemplary embodiment of the present invention.
Figure 38:
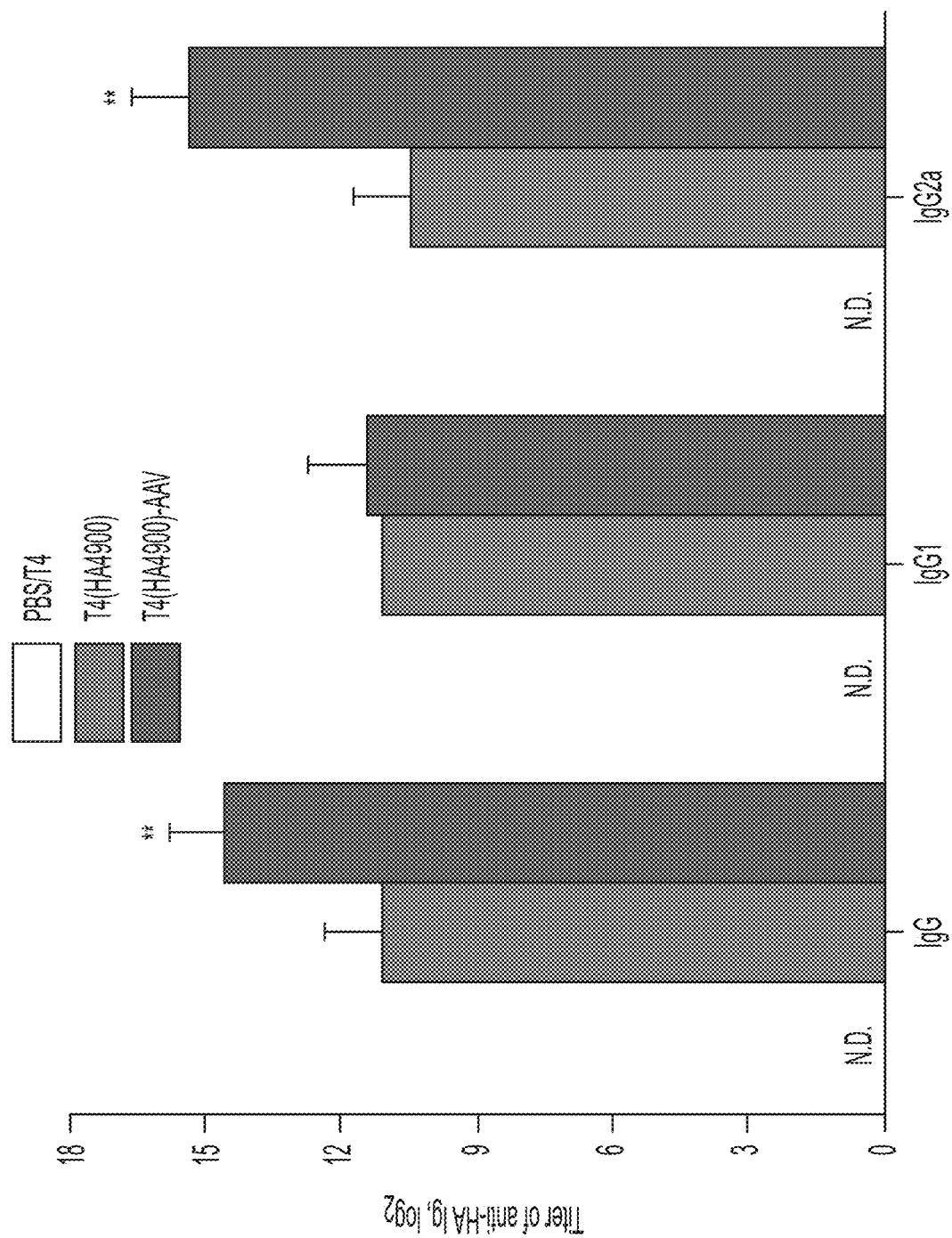
FIG. 38 a graph showing the anti-HA IgG titer on Day 35 induced by T4(HA4900) with or without AAV attached according to an exemplary embodiment of the present invention.
Figure 39:
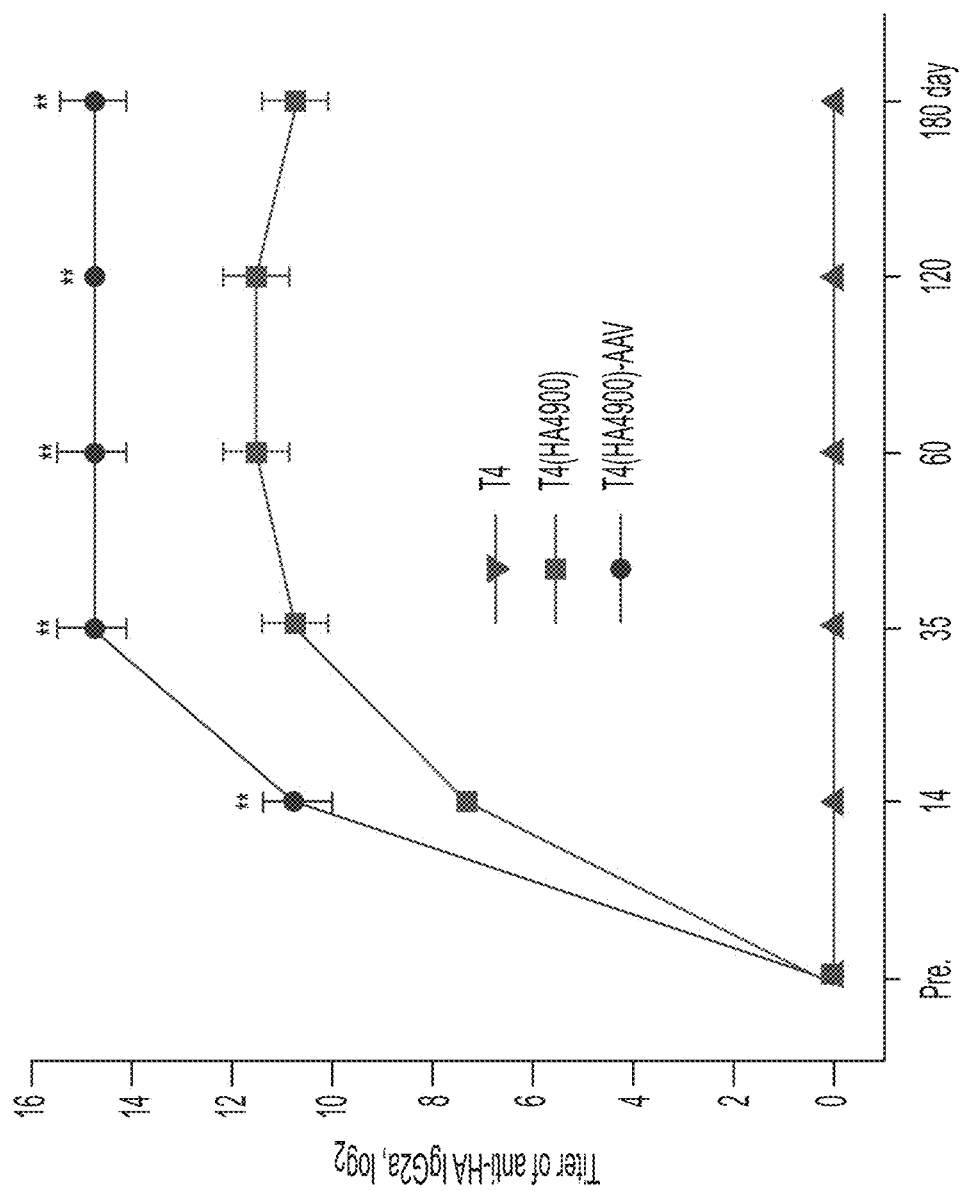
FIG. 39 a graph showing the anti-HA IgG titer from Day 0 to Day 180 induced by T4(HA4900) with or without AAV attached according to an exemplary embodiment of the present invention.

In one embodiment, the mice receive a prime injection and a boost injection on Day 21. The immune response shown as IgG titer is determined on Day 14, Day 35, Day 60, Day 120 and Day 180. A single injection of T4(HA4900) elicited anti-HA IgG titers in mice (Day 14) (FIG. 37), which were further boosted with a second injection (Day 35) (FIG. 38). FIGS. 37 and 38 show the IgG titers on day 14 and day 35, respectively. While PBS and T4 controls induce no immune responses, attachment of AAV induces high IgG titers, thus stronger immune responses, compared to T4 carrying HA4900 without AAV attached. The results confirm that conjugation to AAV significantly improved T4(HA4900) delivery that in turn resulted in increased antigen expression and stronger immunity against an infectious agent. FIGS. 37 and 38 also show the titers of IgG subclasses, IgG1 and IgG2a. The T4(HA4900)-AAV sera contained ~25-fold higher subclass IgG2a titers. FIG. 6E shows the durability of the anti-HA IgG2a titers, which remains stable even at 6-month after immunization. Moreover, the IgG titer of T4(HA4900)-AAV remains higher than that induced by T4 alone throughout 180 days after the prime injection (FIG. 39). These data suggest that the T4-AAV nanoparticles elicit stronger TH1-biased immune responses when compared to T4 head alone.

Strong and durable humoral immune activities are usually characterized by germinal center response and long-lived plasma and memory B cells and are highly dependent on the help of CD4+ follicular helper T cells (Tfh)[33]. CXCL13 [chemokine (C-X-C motif) ligand 13] chemokine is a recognized plasma biomarker for the activities of germinal center and Tfh cells in lymphoid tissue[34].

Figure 40:
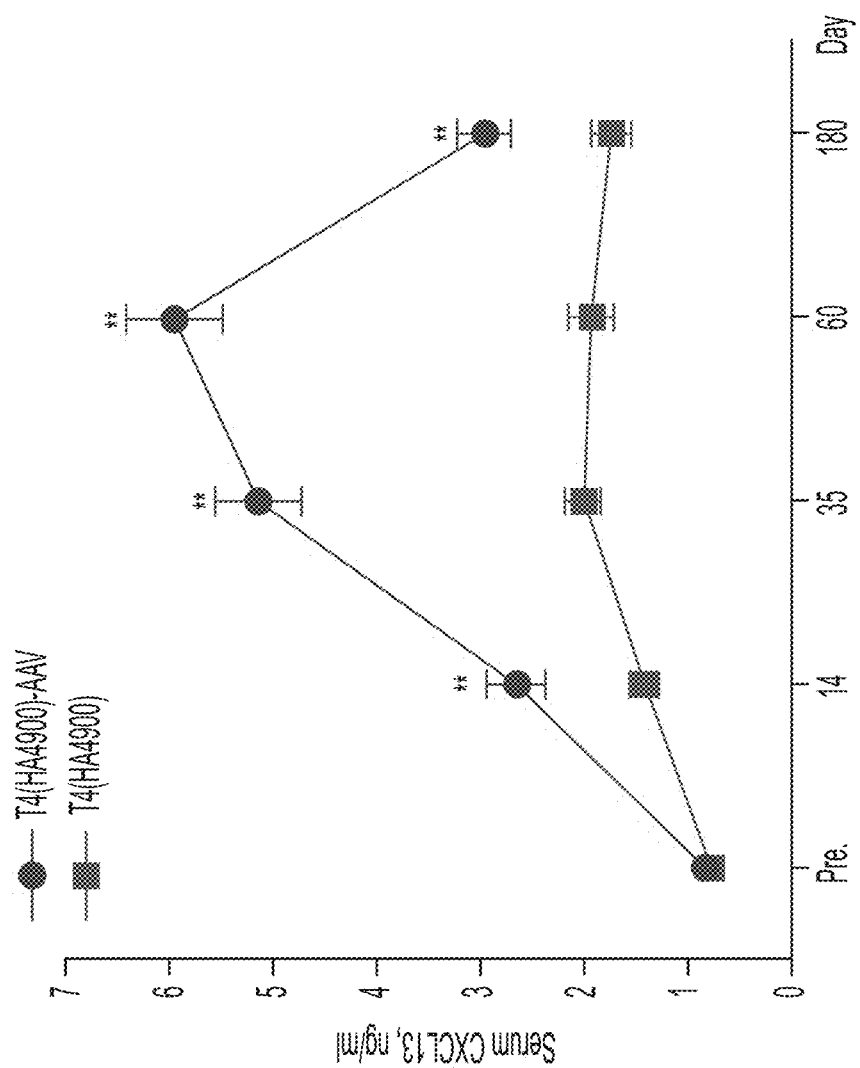
FIG. 40 a graph showing the serum CXCL13 from Day 0 to Day 180 induced by T4(HA4900) with or without AAV attached according to an exemplary embodiment of the present invention.

FIG. 40 shows the serum CXCL13 level throughout 180 days after immunization with T4-AAV nanoparticles. As shown in FIG. 40, T4(HA4900)-AAV immunized mice had ~4 times higher serum concentrations of CXCL13 when compared to T4(HA4900) immunized mice, indicating enhanced activities of germinal center and Tfh cells elicited by the hybrid vector.

Y. pestis is the pathogen causing plague. Plague antigen F1mutV is known to elicit durable immune responses against plague.

In another embodiment, the present invention provides a method of immunizing mice using hybrid T4(HA4900)-AAV nanoparticles comprising: ~10 molecules HA4900 DNA packaged in T4, ~590 molecules of F1mutV displayed on the surface of T4 as a Soc fusion protein, AAV attached to T4 through Hoc-bridge. The mice are immunized following the prime-boost scheme, with a boost injection 21 days after the prime injection.

Figure 41:
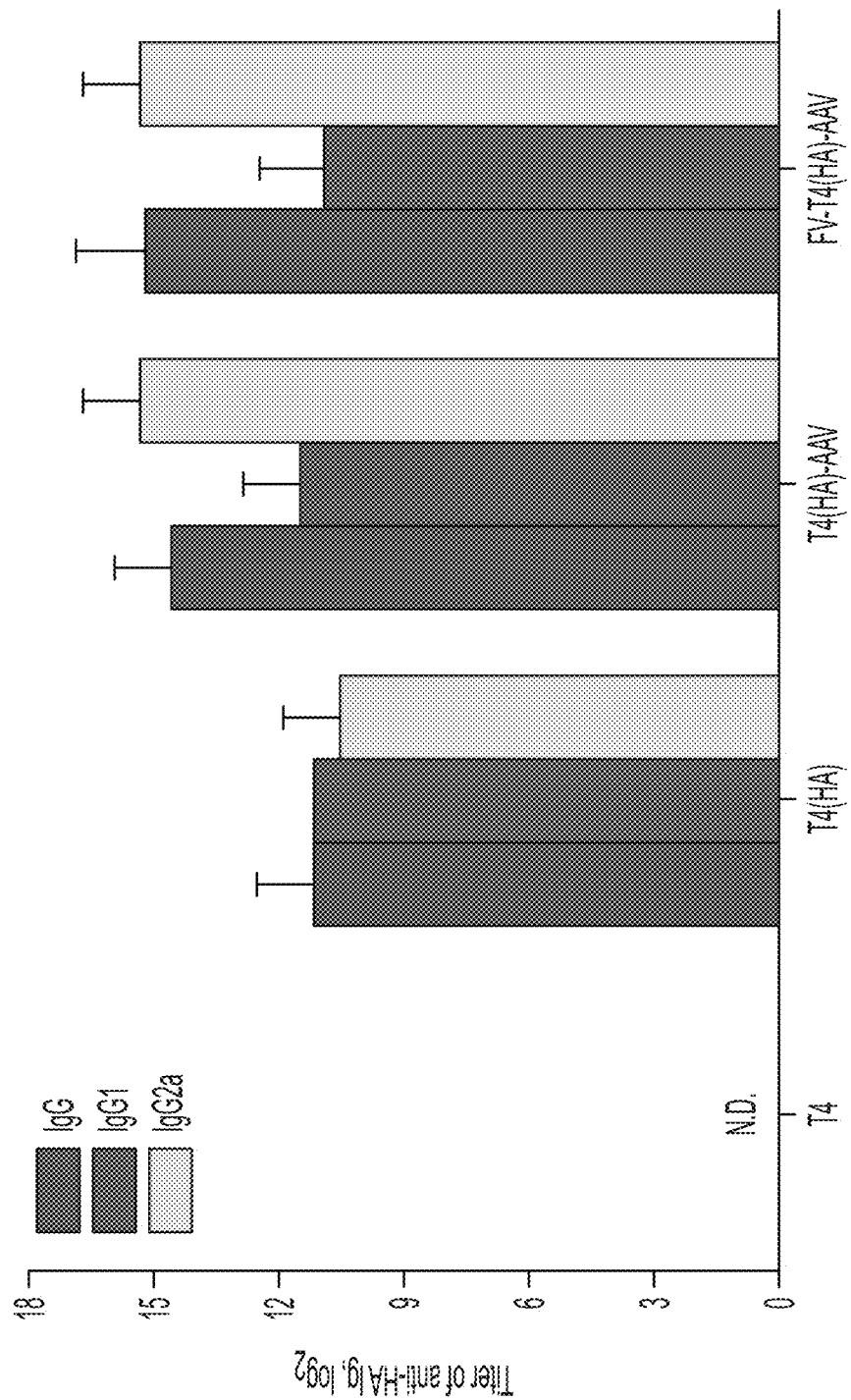
FIG. 41 a graph showing the anti-HA IgG titer induced by T4(HA4900) with or without AAV attached and with or without F1mutV attached according to an exemplary embodiment of the present invention.
Figure 42:
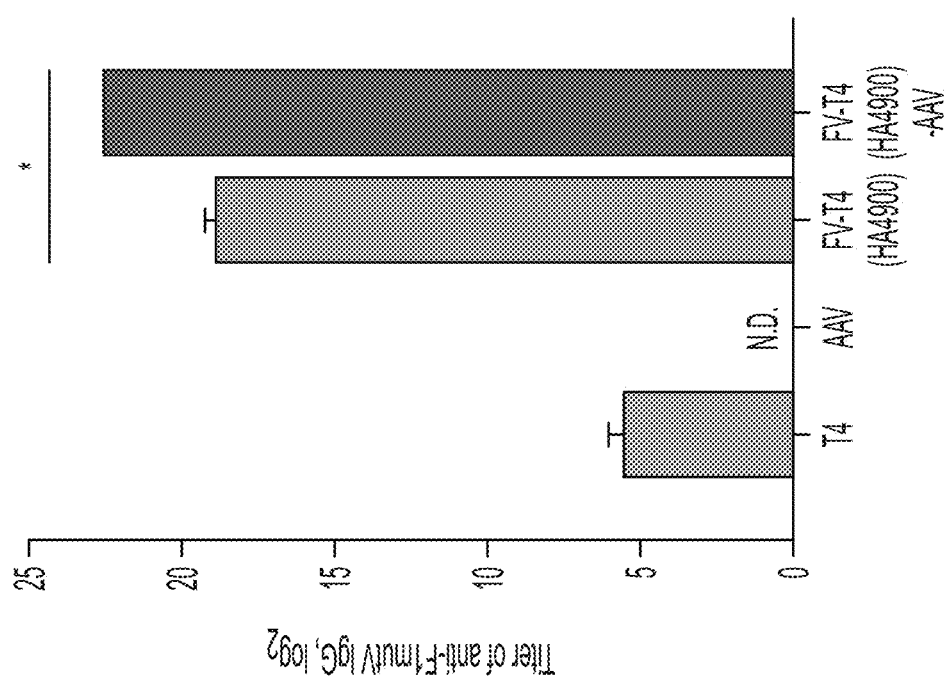
FIG. 42 a graph showing the anti-F1mutV IgG titer induced by F1mutV-T4(HA4900) with or without AAV attached according to an exemplary embodiment of the present invention.

FIG. 41 shows the IgG titers, confirming the attachment of AAV leads to enhanced anti-HA IgG, in particularly IgG2a, titer. Additionally, as shown in FIG. 42, F1mutV-T4 (HA4900)-AAV also stimulated higher total anti-F1mutV IgG titers than F1mutV-T4(HA4900), confirming attachment of AAV also enhance immune responses against protein antigen delivered by T4.

In another embodiment, the mice are immunized with F1mutV-T4(HA4900)-AAV vector using the prime-boost scheme and then challenged at the challenge dose of 295 LD50 [1 LD50=100 colony-forming units (CFU) in Balb/c mice] of the most lethal Y. pestis CO92 on Day 51.

Figure 43:
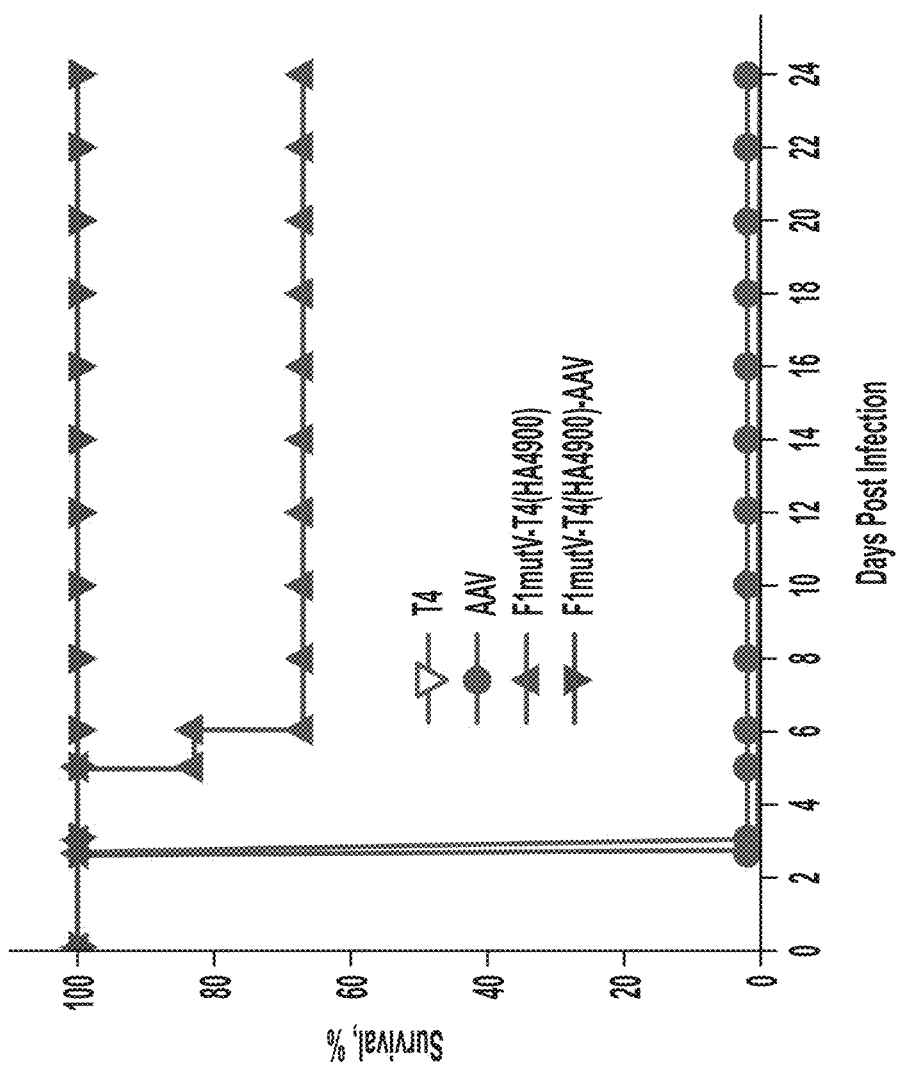
FIG. 43 a graph showing survival rate of mice immunized with F1mutV-T4(HA4900) with or without AAV attached according to an exemplary embodiment of the present invention.
Figure 44:
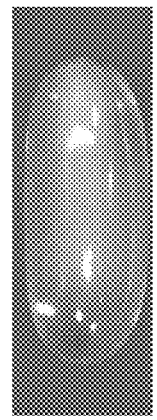
FIG. 44 is an image showing a composition formulated in the dosage form of a soft gel according to an exemplary embodiment of the present invention.
Figure 45:
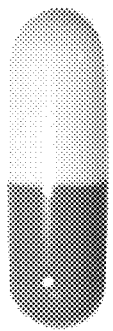
FIG. 45 is an image showing a composition formulated in the dosage form of a hard capsule according to an exemplary embodiment of the present invention.
Figure 46:
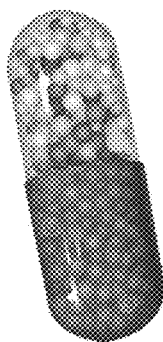
FIG. 46 is an image showing a composition formulated in the dosage form of a hard capsule with compounds coated differently according to an exemplary embodiment of the present invention.
Figure 49:
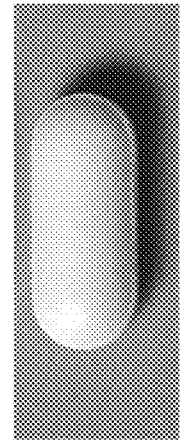
FIG. 49 is an image showing a composition formulated in the dosage form of caplet according to an exemplary embodiment of the present invention.
Figure 48:
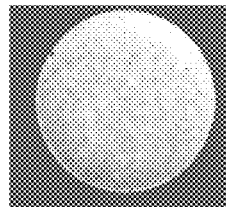
FIG. 48 is an image showing a composition formulated in the dosage form of chewable tablet according to an exemplary embodiment of the present invention.
Figure 47:
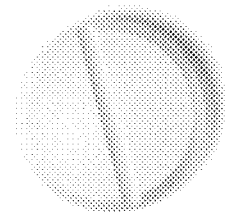
FIG. 47 is an image showing a composition formulated in the dosage form of a tablet according to an exemplary embodiment of the present invention.
Figure 50:
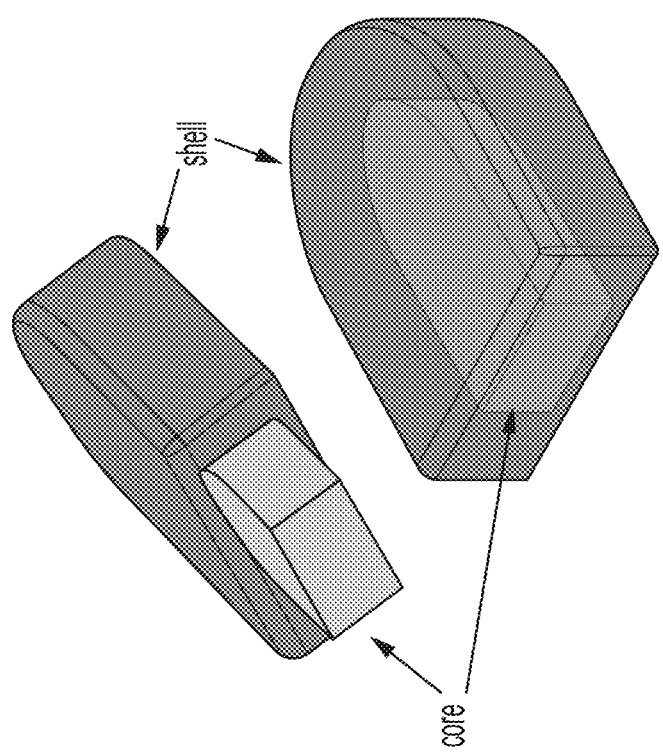
FIG. 50 illustrates a dosage form of a caplet comprising a core encased in a shell according to an exemplary embodiment of the present invention.

FIG. 43 shows the survival rate of mice challenged with Y. pestis CO92. The high survival rate indicates enhanced protection by immunization. As shown in FIG. 43, the F1mutV-T4(HA4900)-AAV vector showed complete protection whereas the unconjugated F1mutV-T4(HA4900) vector showed partial 67% protection. Thus, the results confirmed that attachment of AAV improved the immune response induced by antigen delivered by T4.

In another embodiment, the mice are immunized with F1mutV-T4-AAV(HA4900) vector using the prime-boost scheme and then challenged at the challenge dose of 295 LD50 [1 LD50=100 colony-forming units (CFU) in Balb/c mice] of the most lethal *Y. pestis* CO92 on Day 51.

However, the attachment of AAV fails to lead to enhanced immune responses against HA, compared to T4 head alone (data not shown).

In the present invention, no signs of adverse or toxicity-related effects such as changes in serum alkaline phosphatase, weight loss, or temperature change were evident in any of the mice immunized with T4-AAV nanoparticles.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Plasmid Construction

The plasmids pET-28b-Soc, pET-28b-Soc-β-gal, and pET-28b-F1mutV-Soc were constructed as previously described[10, 12]. For the construction of pET-28b-BAP-Hoc, two rounds of PCR were performed to amplify BAP-Hoc using three primers: FW1=ATCGAGTGGCACGAG-GGTCTTTCGATGACTTTTACAGTTGATATAACTCC (SEQ ID NO: 1), FW2=TTCTAGCTAGCGGTCTT-AACGACATCTTCGAGGCACAGAAGATCGAG-TGGCACG AGGGTCT TCG (SEQ ID NO: 2), and RW=ATAAAGCTTTTATGGATAGGTATAGATGATAC-CAGTTTC (SEQ ID NO: 3). The first round of CR was performed by fusing Hoc to part of the BAP sequence using the FW1 and RW primers Full-length BAP-Hoc was obtained by the second round of PCR using the FW2 and RW primers and then digested with NheI and HindIII. The digested BAP-Hoc fragment was sub-cloned into the ET-28b vector. The BirA-expressing plasmid pET-21a-BirA was purchased from Addgene® plasmid #20857). Plasmids pAAV-DJ, pAAV-Helper, pAAV-GFP, pAAV-luciferase, and pAAV-mCherry were purchased from Cell Biolabs™. To clone DJ-H75A-D76N mutant, upstream fragment was amplified using the primers AN-F (CGCGGAAGCTTCGATCAACTACGCAGACAG) (SEQ ID NO: 4) and HD-AN-R (GTTTGCCTCGAGGGCC-GCGGCGTCTGCCTC) (SEQ ID NO: 5) and the template pAAV-DJ, and downstream fragment was amplified using the primers HD-AN-F (CCGCGGCCCTCGAGGC-AAACAAAGCCTACGACCGGCAGCTCGACA) (SEQ ID NO: 6) and AN-R (GAGAACGTACGGCAGC-TGGTACTCCGAGTC) (SEQ ID NO: 7). Then, the two fragments were mixed in equal amounts and used this as a template to amplify DJ-H75A-D76N using the primers AN-F and AN-R. The PCR products were subsequently cloned into the pAAV-DJ vector at the HindIII/BsiWI restriction sites to construct pAAV-DJ-H75A-D76N. Influenza HA4900 DNA fragment was synthesized by Invitrogen® according to a recent report[31] and then sub-cloned into the pAAV vector after digestion with EcoRI and HindIII. All the constructed plasmids were sequenced to confirm correct fragment insertion (Retrogen®, CA).

Example 2

Protein Expression and Purification.

The recombinant proteins expressed in *Escherichia coli* (*E. coli*) BL21 (DE3) RIPL cells were purified according to previously described protocols[10, 12]. Influenza HA4900 was purified from HEK293F suspension cells (Thermo Fisher Scientific®, MA) according to previous reports[31]. Briefly, the pAAV-ITRs-HA4900 plasmid was transiently transduced into HEK293F cells maintained in FreeStyle® 293 expression medium (Thermo Fisher Scientific®, MA) using the 293Fectin™ transfection reagent (Thermo Fisher Scientific®, MA). The cells were then incubated at 37° C. and 8% $CO_2$ while shaking at 130 rpm overnight. After 12 h, an equal volume of fresh medium supplemented with sodium butyrate solution (enhancing protein expression, 2 nM final concentration) (Sigma-Aldrich®, MO) was added to the cells. On day 7, the pure supernatants were harvested by centrifugation and filtered over 0.22-µm filters (Sartorius Stedim Biotech, Germany). Proteins were purified using HisTrapHP and gel filtration columns (GE Healthcare™, IL).

Example 3

Production of the T4 Head and AAV

The 10-amber 13-amber hoc-del soc-del T4 heads were purified according to previously described protocols[6]. *E. coli* P301 (sup-) cells (500 mL) infected with this mutant were lysed in 40 mL of Pi-Mg buffer (26 mM $Na_2HPO_4$/68 mM NaCl/22 mM $KH_2PO_4$/1 mM $MgSO_4$, pH 7.5) containing 10 µg/mL DNaseI and chloroform (1 mL) and incubated at 37° C. for 30 min. The lysate was subjected to two low-speed (6,000×g for 10 min) and high-speed (35,000×g for 45 min) centrifugations, and the final heads pellet was resuspended in 200 µL of Tris.Mg buffer (10 mM Tris.HCl, pH 7.5/50 mM NaCl/5 mM $MgCl_2$) and purified by CsCl density gradient centrifugation. The major head band sedimented at about ⅓ from the bottom of a 5-mL gradient was extracted and dialyzed overnight against Tris-Mg buffer. The heads were further purified by DEAE-Sepharose chromatography. The peak heads fractions were concentrated and stored at −80° C.

The rAAV-DJ was produced using the triple-plasmid transfection method (Cell Biolabs®, CA) according to the manufacturer's instructions. Briefly, plasmids, including an adenovirus helper plasmid (pHelper), a rep/cap plasmid expressing rep and cap (pAAV-DJ or pAAV-DJ-H75A-D76N), and a transgene plasmid carrying the AAV transgene cassette (AAV genome) (pAAV-GFP, pAAV-mCherry, pAAV-luciferase, pAAV-HA4900, or pAAV-VRCO1) (1:1:1), were co-transfected into HEK293 cells expressing adenovirus E1a and E1b proteins using polyethyleneimine (PEI) (Polysciences, PA). After 72 h, cells were harvested by centrifugation at 1,140×g for 10 min. The cell pellet was resuspended in lysis buffer (50 mM Tris-HCl, pH 8.5, 0.15 M NaCl) and lysed by three freeze/thaw cycles in dry ice-ethanol and a 37° C. water bath. Benzonase was added to the mixture (50 U/ml final concentration), and the lysate was incubated for 30 min at 37° C. The lysate was clarified by centrifugation at 3,700×g for 20 min, and the virus-containing supernatant was considered to be the crude lysate. Viruses were then purified by discontinuous iodixanol density gradient centrifugation at 500,000 rpm for 16 h at 4° C. (Type 55 Ti rotor, Beckman®, CA) and by HiTrap AVB Sepharose® HP according to the manufacturer's instructions (GE Healthcare™, IL). The peak fractions were dialyzed against PBS-MK buffer (PBS, pH 7.4, 2.5 mMKCl, and 1 mMMgCl$_2$) in Slide-A-Lyzer dialysis cassettes (Thermo Fisher Scientific®, MA). The dialyzed AAV particles were concentrated and stored at −80° C. AAV titers were determined using a QuickTiter AAV Quantitation kit (Cell Biolabs®, CA).

Example 4

In Vitro DNA Packaging and Protein Display of the T4 Head.

For in vitro DNA packaging assays, each 20 µl reaction mixture contained purified T4 heads (~2×10$^{11}$ particles), purified full-length gp17 (~3 µM), and linearized DNA in packaging buffer (30 mM Tris-HCl, pH 7.5, 100 mM NaCl, 3 mM MgCl$_2$, and 1 mM ATP). The mixture was incubated at 37° C. for 30 min, followed by benzonase nuclease addition and incubation at 37° C. for 20 min to remove excess unpackaged DNA. The encapsidated nuclease-resistant DNA was released by treatment with 50 mM ethylenediaminetetraacetic acid (EDTA), 0.5 µg/µl proteinase K (Thermo Fisher Scientific®, MA), and 0.2% SDS for 30 min at 65° C. The packaged DNA was analyzed by 1% (wt/vol) agarose gel electrophoresis followed by staining with ethidium bromide, and the amount of packaged DNA was quantified using Quantity One software (Bio-Rad™, CA). The packaging efficiency was defined as the number of DNA molecules packaged per T4.

In vitro protein display on the T4 head was assessed by the co-sedimentation described previously[8]. Briefly, after encapsidating linearized DNA as described above, T4 heads were incubated with Soc- and/or Hoc-fusion proteins at 4° C. for 45 min. The mixtures were sedimented by centrifugation at 30,000×g for 45 min, and unbound proteins in the supernatants were removed. After washing twice with PBS, the pellets were incubated at 4° C. overnight and then resuspended in PBS for SDS/PAGE analysis or Opti-MEM for transduction. After Coomassie BlueR250 (Bio-Rad™, CA) staining and destaining, the protein bands on SDS-PAGE gels were scanned and quantified by laser densitometry (PDSI, GE Healthcare™, IL). The densities of the Hoc, Soc, and gp23 bands were determined for each lane separately, and the copy numbers of bound Hoc or Soc fusion molecules per capsid were calculated using gp23 as the internal control (930 copies per capsid).

Example 5

Biotinylation of AAV Vectors and Soc Proteins.

AAV vectors and Soc proteins were biotinylated using EZ-Link™ Sulfo-NHS-LC-biotin according to the manufacturer's instructions (Thermo Fisher Scientific®, MA). Purified AAV vectors (1×10$^{12}$ particles) were incubated with 500 nmol of Sulfo-NHS-LC-biotin at 37° C. for 2 h in PBS buffer. For Soc protein biotinylation, a 20-fold molar excess of the biotin reagent was used to label 10 mg of Soc in PBS buffer. To remove free biotin, the reaction mixture was dialyzed against PBS-MK buffer in Slide-A-Lyzer® dialysis cassettes (Thermo Fisher Scientific®, MA). Dialyzed bio-AAV and bioSoc were concentrated and stored at −80° C.

Example 6

HBBA Production.

A 15-amino acid biotin acceptor peptide (BAP, GLN-DIFEAQKIEWHE) (SEQ ID NO: 8) was fused to the N-terminus of the Hoc protein. The *E. coli* enzyme biotin ligase (BirA) sequence specifically ligates biotin to BAP. Briefly, His6-tagged BirA and Hoc-BAP were induced in BL21RIPL cells and purified via a HisTrapHP column and SEC. For Hoc-BAP biotinylation, 1 µM recombinant BirA ligase was added to 30 µM Hoc-BAP monomer (in PBS-MgCl$_2$ buffer, pH 7.4) in the presence of 0.3 mM biotin and 5 mM ATP. The reaction proceeded at room temperature (RT) for 3 h. Biotinylation was confirmed by streptavidin-HRP western blot analysis. Free biotin was removed by Zeba™ Desalt spin columns (Thermo Fisher Scientific®, MA). The biotinylation reaction mixture was loaded onto the center of the compact resin bed and centrifuged at 1,000×g for 2 min to collect the desalted sample. Purified Hoc-BAP-biotin was incubated with avidin at a 1:3 ratio for 1 h at 4° C. HBBA was purified by SEC. The peak fractions were concentrated and stored at −80° C.

Example 7

T4-Soc-AAV and T4-Hoc-AAV Vector Production.

For assembly of T4-Soc-AAV vectors on nickel beads, T4-Soc(His6)-Biotin vectors were loaded onto Ni$^{2+}$-NTA agarose beads (Qiagen®, Netherlands). After incubation for 1 h at 4° C., the mixture was centrifuged at 100×g for 30 s and washed five times with binding buffer. Avidin dissolved in binding buffer was then added to the beads. After 20 min of incubation at 4° C., free avidin was removed by washing and centrifugation. Biotinylated AAV vectors were then added to the T4-Soc-SBA immobilized beads and incubated for 30 min. After washing five times with binding buffer, bound T4-Soc-AAV vectors were eluted with elution buffer (50 mM Tris-HCl, pH 8.0, 300 mM NaCl, and 300 mM imidazole). The protocol for assembling T4-Hoc-AAV on nickel beads was similar to that utilized for T4-Soc-AAV. Finally, the eluted vectors were exchanged into PBS-MK buffer.

Example 8

Western Blot Analysis.

AAV or T4-AAV particles were boiled in loading buffer for 10 min, separated by 12% SDS-PAGE, and then transferred to nitrocellulose membranes (Bio-Rad™, CA). Blocking was performed in 5% BSA/PBS-T buffer (PBS, pH 7.4, 0.05% Tween-20) at RT for 1 h with gentle shaking. Blots were then washed three times with PBS-T. Primary antibodies were added to the blots and incubated overnight at 4° C. in PBS with 5% BSA. AAV VP proteins were detected using the AAV capsid protein-specific antibody B1 (diluted 1:50, American Research Products, MA), which recognizes VP1, VP2, and VP3 based on their identical C-terminal regions. After washing with PBS-T three times, a secondary goat anti-mouse HRP-conjugated antibody (Thermo Fisher Scientific®, MA) was applied at a 1:2,000 dilution in 5% BSA/PBS-T for 1 h at RT, followed by rinsing three times with PBS-T. The bio-AAV, bio-Soc, and Hoc-BAP-biotin were directly detected by HRP-conjugated streptavidin (Abcam®, UK). Signals were visualized with an enhanced chemiluminescence substrate (Bio-Rad™, CA) using the Bio-Rad™ Gel Doc XR+ system and Image Lab software according to the manufacturer's instructions (Bio-Rad™, CA).

Example 9

Labeling of T4 Capsid.

To label the T4 capsid with amine-reactive Alexa Fluor® 594 (Thermo Fisher Scientific®, MA), the pelleted T4 heads were resuspended in 0.1 M carbonate buffer, pH 9.0. Alexa Fluor® 594 was added to a final concentration of 0.2 mg/ml. After incubation for 1 h at room temperature with rotation in the dark, unbound dye was removed via buffer exchange into PBS, pH 7.4.

Example 10

TEM.

The T4-AAV complex was applied to the carbon grid for 5 min at room temperature. The grid was then frozen in liquid nitrogen using Gatan® CP3 cryo-plunger. The cryo-EM images of T4, AAV, and T4-AAVcomplex were kindly collected by Dr. Qianglin Fang at Purdue University using a Titan Krios microscope equipped with a charge-coupled device (CCD) camera. AAV particles for this experiment were provided by Dr. Mavis Agbandje-McKenna, University of Florida.

Example 11

Cell Culture.

HEK293 cells were cultured in Dulbecco's Modified Eagle's Medium (DMEM, Gibco®) supplemented with 10% fetal bovine serum (FBS) (Thermo Fisher Scientific®, MA), 1×HEPES (Thermo Fisher Scientific®, MA), and 1% antibiotics (Thermo Fisher Scientific®, MA) (complete DMEM). Cells were passaged with 0.05% trypsin/EDTA at a sub-cultivation ratio of 1:5 at 80-90% confluence and incubated in a humidified atmosphere at 37° C. and 5% $CO_2$.

Example 12

Cell Transduction and the Detection of Gene and Protein Delivery.

HEK293 cells were seeded in 24-well plates at $2.0 \times 10^5$ cells per well in complete DMEM. After 24 h, the cells were incubated with the AAV, bio-AAV, T4 or T4-AAV vectors at different MOIs in antibiotic-free Opti-MEM for 6 h. Thereafter, Opti-MEM was removed and replaced with complete DMEM. The cells were further incubated at 37° C. for an additional 48 h. GFP/mCherry transgene expression was observed by fluorescence microscopy (Carl Zeiss, Germany) at 48 h post-transduction, and the mean fluorescence intensities were quantified by ImageJ software. The nucleus was stained by Hoechst 33342 (Thermo Fisher Scientific®, MA). To analyze luciferase gene delivery into cells by T4 or the T4-AAV, we measured luciferase activity with the Luciferase Assay System (Promega®, WI) according to the manufacturer's instructions. Briefly, growth medium was removed, and cells were rinsed with PBS buffer. After removing the wash buffer, 150 µl of passive lysis buffer was added to each well, followed by gentle shaking at RT for 20 min. Twenty microliters of the cell lysate were then transferred to a 96-well white opaque plate and mixed with 80 µl of Luciferase Assay Reagent, and the luminescence signal was recorded by the Glomax Multi Detection System (Promega®, WI). The activity of the Soc-3-gal enzyme displayed on the T4 head in cells was determined by staining with X-Gal using the β-Galactosidase Staining kit (Sigma-Aldrich®, MO). Triplicate measurements were applied to each group.

Example 13

Co-Localization Analysis.

Images were processed using Zen (Carl Zeiss, Germany) and ImageJ software. To quantify the extent of co-localization for a two-color comparison, the linear Pearson ($r_p$) and nonlinear Spearman's rank ($r_s$) correlation coefficients for pixels that represented the fluorescence signals in the green and red channels were calculated using the ImageJ PSC plugin.

Example 14

Cell Viability Assay.

After transfection for 48 h, cell viability was determined using the CellTiter-Glo® Luminescent Cell Viability Assay Kit (Promega®, WI) following the manufacturer's instructions. Briefly, an equal volume of CellTiter-Glo® Reagent was added to the cell culture in each well. The mixture was placed on an orbital shaker for 2 min to induce cell lysis and then incubated at RT for 10 min to stabilize the luminescence signal, which was recorded by the Glomax Multi Detection System (Promega®, WI). The viability of the untreated cell group was arbitrarily set to 100%, and triplicate measurements were applied to each group.

Example 15

In Vivo Bioluminescence Imaging.

In vivo Bioluminescence Imaging was conducted as previously described[10]. Specifically, $5 \times 10^{10}$ and $2 \times 10^{11}$ T4 or T4-AAV particles were intramuscularly injected into BALB/c mice. At 0.25 day (d), 0.5 d, 1 d, 2 d, 5 d, 10 d, 15 d, 30 d, and 60 d post-administration, 30 µg of RediJect D-Luciferin Ultra (Perkin-Elmer™, MA), a luciferase substrate dissolved in 0.9% saline, was injected intraperitoneally. After 5 min, the mice were lightly anesthetized with 2% isoflurane and placed on an IVIS 200 bioluminescence whole-body imaging workstation (Caliper™). The bioluminescence emission signal was quantified using the camera control program, Living Image software, and displayed in physical units of surface radiance, photons per second per centimeter squared per steradian (photons/second/$cm^2$/sr).

Example 16

Mouse Immunizations.

All animal experiments were approved by the Institutional Animal Care and Use Committee of the Catholic University of America (Washington, D.C.) and the University of Texas Medical Branch (Galveston, Tex.). Mice (BALB/c, female, 6-8 weeks old, Jackson Laboratories, ME) were randomly grouped and allowed to acclimate for 7 days, followed by intramuscular immunizations into their hind legs with vectors (priming on day 0 and boosting on day 21). A group of mock-immunized mice (PBS only) was included as negative control. Blood was drawn from each animal on days 0 (pre-bleed), 14, 21, 35, 60, 120, and 180, and the isolated sera were stored at −80° C.

Example 17

ELISA.

ELISA plates (Evergreen Scientific, CA) were coated with 0.1 μg of protein per well in coating buffer (0.05 M sodium carbonate-sodium bicarbonate, pH 9.6) overnight at 4° C. After washing three times with PBS-T buffer, the plates were blocked with PBS-3% BSA buffer for 1 h at 37° C. The concentrations of antigen-specific IgG/G1/G2a in sera were monitored using a 5-fold dilution series beginning with an initial 100-fold dilution in PBS-1% BSA. The diluted serum samples were added to each well, and the plates were incubated at 37° C. for 1 h and washed five times with PBS-T buffer. The secondary goat anti-mouse IgG-HRP antibody (HRP-conjugated goat anti-mouse IgG1 or IgG2a secondary antibodies were used for IgG1/IgG2a subtypes, Invitrogen®) was then added to each well at a 1:5,000 dilution and incubated for 1 h at 37° C., followed by washing five times with PBS-T buffer. Next, the TMB (3,3',5,5'-tetramethylbenzidine) Microwell Peroxidase Substrate System (KPL) was applied in the dark for color development. After 10 min, the enzymatic reaction was quenched by adding TMB BlueSTOP (KPL) solution, and plates were read within 30 min at 650 nm by an ELISA reader (VERSA max, Molecular Devices). Endpoint titers were presented as the sample dilution resulting in an OD650 equal to twice the mean background (negative serum) of the assay. For CXCL13 quantification in sera, the mouse CXCL13 ELISA kit (Boster Biological Technology, CA) was used by following the manufacturer's instructions.

Example 18

Alkaline Phosphatase (ALP) Assay.

The ALP biochemical parameter was determined in sera of mice immunized with T4, AAV, or T4-AAV. Naive mice were used as control. ALP level was measured using a commercial ALP assay kit (Elabscience®, MD) following the manufacturer's instructions.

Example 19

Mouse Challenges.

The acclimated mice were intramuscularly immunized into their hind legs with T4, AAV, F1mutV-T4(HA4900), or F1mutV-T4(HA4900)-AAV (priming on day 0 and boosting on day 21). Sera were collected from each animal on days 0 (pre-bleeds) and 35 for immunological analyses. On day 42, mice were intranasally challenged with 295 LD50 of *Y. pestis* CO92 bacteria[40]. Animals were monitored and recorded for mortality, body weight, and body temperature.

Example 20

Statistics.

All quantified data are presented as the mean±standard deviation (SD). Statistical analyses were performed by two-tailed Student's t-tests. Significant differences between two groups are indicated by *$p<0.05$ or **$p<0.01$.

Example 21

Use Utilities.

A therapeutically effective amount of the hybrid vector is used as DNA and protein delivery tool or for the vaccination against infectious diseases such as, but not limited to, COVID, flu, HIV, anthrax and plague.

Routes of Administration

A therapeutically effective amount of the hybrid vector carrying DNA molecules or proteins can be administered by a variety of routes. In effecting vaccination of a subject to prevent infectious diseases such as, but not limited to, COVID, flu, HIV, anthrax and plague, the hybrid vector can be administered in any form or mode that makes the hybrid vector bioavailable in an effective amount. For example, the compounds can be administered orally, by inhalation, or by the subcutaneous, intramuscular, intravenous, transdermal, intranasal, rectal, ocular, topical, sublingual, buccal, or other routes.

One skilled in the art of preparing hybrid vector can readily select the proper form and mode of administration depending upon the particular characteristics of the hybrid vector selected, the disorder or condition to be treated, the stage of the disorder or condition, and other relevant circumstances.

Pharmaceutical Compositions

The pharmaceutical compositions are prepared in a manner well known in the pharmaceutical art, wherein the pharmaceutical compositions comprise therapeutically effective amount of compositions of the hybrid vector carrying one or more DNA molecules and proteins. The carrier or excipient may be a solid, semi-solid, or liquid material that can serve as a vehicle or medium for the active ingredient. Suitable carriers or excipients are well known in the art.

The pharmaceutical composition may be adapted for oral or parenteral and may be administered to the subject in the dosage form of tablets, sugar-coated tablets, capsules, delayed-release hard capsules, softgel, chewable tablets, gummy, injection fluids, caplets, powders, granules, syrups, aerosols, inhalants, suppositories, solutions, suspensions, catheters containing the composition, syringes containing the composition, implants containing the composition, transdermal patch, or the like.

In one example, a composition disclosed herein may be formulated in a dosage form of a softgel as shown in FIG. 44. A composition disclosed herein may be formulated in a dosage form of hard capsule as shown in FIG. 45. A composition disclosed herein may also be formulated in a dosage form of a hard capsule wherein each different compound in the composition is coated differently (FIG. 46).

In another example, a composition disclosed herein may be formulated in a dosage form of a tablet as shown in FIG. 47. A tablet comprising a composition disclosed herein may be a chewable tablet as shown in FIG. 48. A composition disclosed herein may also be formulated in a caplet as shown in FIG. 49. A caplet comprising a composition disclosed herein may be formulated as a controlled-release caplet comprising two or more portions, such as a core and a shell, wherein the core is within the shell, as shown in FIG. 50.

In addition to above examples of dosage forms for oral administration, the disclosed composition may also be delivered to a body of a subject such as via injection. A composition may be formulated in a dosage form of an injection fluid and be loaded into an injectable device (e.g., a syringe), to inject into a subject's body. FIG. 51 is an illustration of a treatment delivery apparatus (5110) comprising an injectable drug delivery device (5112) and a composition disclosed herein in the dosage form of an injection fluid (5114). The composition disclosed herein may be delivered through an injection through skin (5120) of a subject and go into the body (5122) of the subject. In select embodiments, the injectable drug delivery device may stay outside (5124) of the subject's body.

Figure 51:
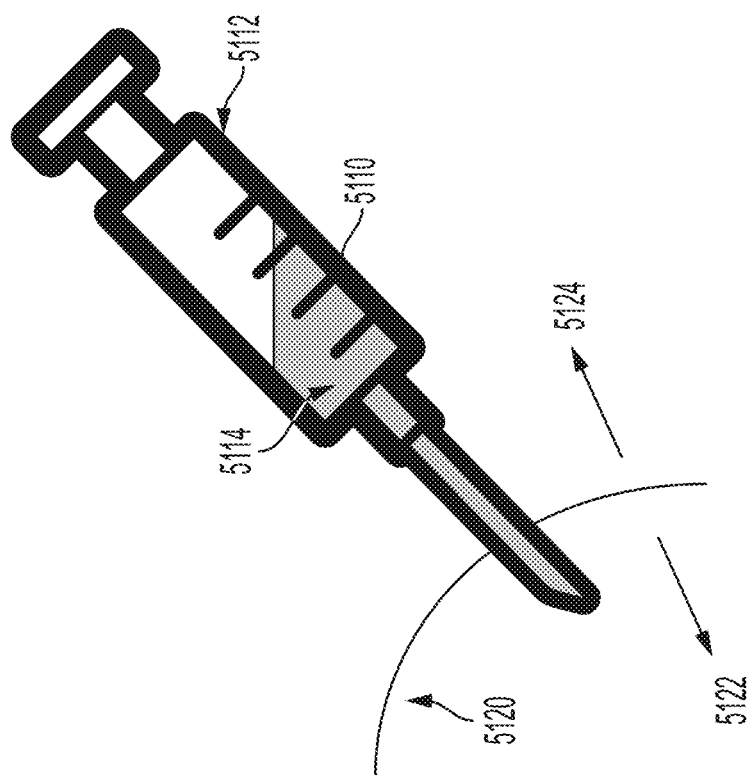
FIG. 51 illustrates a treatment delivery apparatus for delivering a composition disclosed herein comprising an injectable drug delivery device and an injection fluid according to an exemplary embodiment of the present invention.

FIG. 51 represents merely one illustrative embodiment of a composition for delivery into a subject's body. The delivery instrument may not be limited to syringe-type device. One of ordinary skill in the art would readily appreciate that any injectable device suitable for delivering the disclose product(s) or agent of a patient's body may be utilized according to aspects of the present invention.

Figure 52:
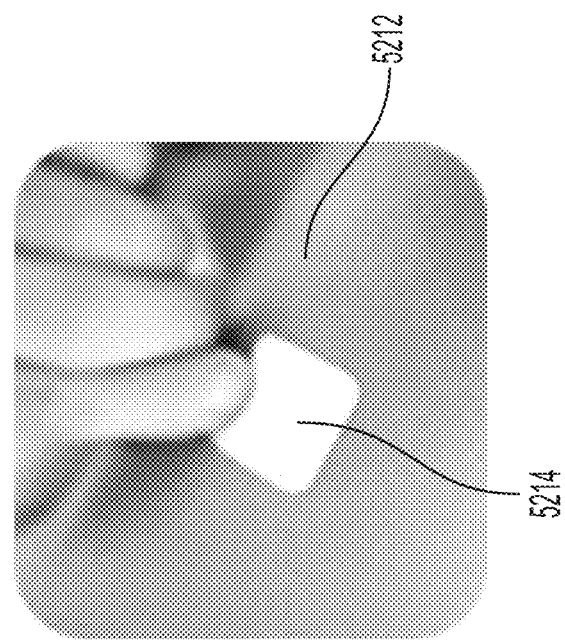
FIG. 52 illustrates a treatment delivery apparatus comprising a transdermal patch for delivering the composition disclosed herein into a subject's body according to an exemplary embodiment of the present invention.

In some examples, a composition disclosed herein may be delivered into a subject's body such as via a transdermal patch. FIG. 52 illustrates a transdermal patch 5214 comprising a composition disclosed herein. Transdermal patch 5214 may comprise an adhesive patch for placing on the skin 5212 of a subject and one or more active layers embedded in the adhesive patch, wherein the one or more active layers comprise a composition disclosed herein in a therapeutically effective amount. Transdermal patch 5214 may be placed on to a subject's body to allow the composition embedded in the adhesive patch be delivered into the subject's bloodstream.

Figure 53:
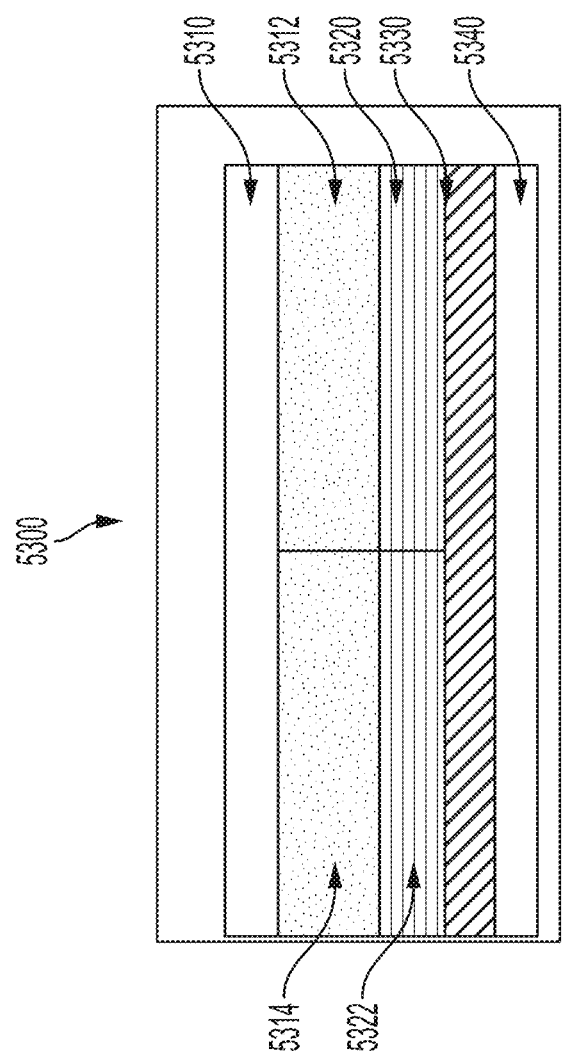
FIG. 53 illustrates a transdermal patch comprising a composition disclosed herein embedded within the transdermal patch according to an exemplary embodiment of the present invention.

In some examples, as shown in FIG. 53, in a transdermal patch 5300, a composition of a therapeutically effective amount of the hybrid vector are formulated into one or more active layers (for example, 5312 and 5314) and embedded under an impermeable backing layer 5310. FIG. 52 and FIG. 53 are only illustrative representations of an exemplary delivery of a disclosed composition into a subject's body through a transdermal patch. One of ordinary skill in the art would readily appreciate that any kind of transdermal patch suitable for delivering the disclosed products described in the present invention may be utilized.

Doses

The composition may be used at appropriate dosages defined by routine testing to obtain optimal pharmacological effect, while minimizing any potential toxic or otherwise unwanted effects.

An effective amount can be readily determined by the attending diagnostician, as one skilled in the art, by the use of conventional techniques and by observing results obtained under analogous circumstances. In determining an effective amount, the dose of a hybrid vector, a number of factors are considered by the attending diagnostician, including, but not limited to: the vector to be administered; the species-its size, age, and general health; the specific disorder involved; the degree of involvement or the severity of the disorder; the response of the individual subject; the mode of administration; the bioavailability characteristics of the preparation administered; the dose regimen selected; the use of other concomitant medication; and other relevant circumstances.

The specific dose administered may be determined by particular circumstances surrounding each situation. These circumstances can include: the route of administration, the prior medical history of the recipient, the symptom being treated, the severity of the symptom being treated, and the age of the recipient. The recipient subject's attending physician should determine the therapeutic dose administered in light of the relevant circumstances.

Also, it is to be understood that the exact dose may be determined, in accordance with the standard practice in the medical arts of "dose titrating" the recipient; that is, initially administering a low dose of the compound, and gradually increasing the dose until the desired therapeutic effect is observed.

It is to be further understood that the dosage regimen can be selected in accordance with a variety of factors. These include type, species, age, weight, sex, diet, and medical condition of the subject; the severity of the condition to be treated; the route of administration; the kidney and liver functions of the subject; the time of administration; the rate of excretion; and the particular hybrid vector employed. A physician of ordinary skill can readily determine and prescribe the effective amount of the drug required to prevent, counter or arrest the progress of the disease or disorder that is being treated.

In one example, this product may be used for administration according to a continuous schedule having a dosing interval selected from one or more of: once daily dosing and/or multiple daily dosing. In one embodiment, this product may be administered to a subject having a need thereof chronically.

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:
1. J. W. Yoo, D. J. Irvine, D. E. Discher, S. Mitragotri, Bio-inspired, bioengineered and biomimetic drug delivery carriers. *Nat. Rev. Drug Discov.* 10, 521-535 (2011).
2. M. P. Stewart, A. Sharei, X. Ding, G. Sahay, R. Langer, K. F. Jensen, In vitro and ex vivo strategies for intracellular delivery. *Nature* 538, 183-192 (2016).
3. M. Giacca, S. Zacchigna, Virus-mediated gene delivery for human gene therapy. *J. Controlled Release* 161, 377-388 (2012).
4. B. Cao, M. Yang, C. Mao, Phage as a Genetically Modifiable Supramacromolecule in Chemistry, Materials and Medicine. *Acc. Chem. Res.* 49, 1111-1120 (2016).
5. M. Karimi, H. Mirshekari, S. M. MoosaviBasri, S. Bahrami, M. Moghoofei, M. R. Hamblin, Bacteriophages and phage-inspired nanocarriers for targeted delivery of therapeutic cargos. *Adv. Drug Deliv. Rev.* 106, 45-62 (2016).
6. Z. Zhang, V. I. Kottadiel, R. Vafabakhsh, L. Dai, Y. R. Chemla, T. Ha, V. B. Rao, A promiscuous DNA packaging machine from bacteriophage T4. *PLoS Biol.* 9, e1000592 (2011).
7. G. Leffers, V. B. Rao, A discontinuous headful packaging model for packaging less than headful length DNA molecules by bacteriophage T4. *J. Mol. Biol.* 258, 839-850 (1996).
8. Q. Li, S. B. Shivachandra, Z. Zhang, V. B. Rao, Assembly of the small outer capsid protein, Soc, on bacteriophage T4: a novel system for high density display of multiple large anthrax toxins and foreign proteins on phage capsid. *J. Mol. Biol.* 370, 1006-1019 (2007).

9. A. Bruttin, H. Brussow, Human volunteers receiving *Escherichia coli* phage T4 orally: a safety test of phage therapy. *Antimicrob. Agents Chemother.* 49, 2874-2878 (2005).

10. P. Tao, M. Mahalingam, B. S. Marasa, Z. Zhang, A. K. Chopra, V. B. Rao, In vitro and in vivo delivery of genes and proteins using the bacteriophage T4 DNA packaging machine. *Proc. Natl. Acad. Sci.* 110, 5846-5851 (2013).

11. P. Tao, M. Mahalingam, J. Zhu, M. Moayeri, J. Sha, W. S. Lawrence, S. H. Leppla, A. K. Chopra, V. B. Rao, A Bacteriophage T4 Nanoparticle-Based Dual Vaccine against Anthrax and Plague. *mBio* 9, (2018).

12. P. Tao, M. Mahalingam, M. L. Kirtley, C. J. van Lier, J. Sha, L. A. Yeager, A. K. Chopra, V. B. Rao, Mutated and bacteriophage T4 nanoparticle arrayed F1-V immunogens from *Yersinia pestis* as next generation plague vaccines. *PLoS Pathog.* 9, e1003495 (2013).

13. P. Tao, X. Wu, V. Rao, Unexpected evolutionary benefit to phages imparted by bacterial CRISPR-Cas9. *Sci. Adv.* 4, eaar4134 (2018).

14. P. Tao, X. Wu, W. C. Tang, J. Zhu, V. Rao, Engineering of Bacteriophage T4 Genome Using CRISPR-Cas9. *ACS Synth. Biol.* 6, 1952-1961 (2017).

15. R. J. Samulski, N. Muzyczka, AAV-Mediated Gene Therapy for Research and Therapeutic Purposes. *Annu. Rev. Virol.* 427-451 (2014).

16. Z. Chen, L. Sun, Z. Zhang, A. Fokine, V. Padilla-Sanchez, D. Hanein, W. Jiang, M. G. Rossmann, V. B. Rao, Cryo-EM structure of the bacteriophage T4 isometric head at 3.3—A resolution and its relevance to the assembly of icosahedral viruses. *Proc. Natl. Acad. Sci.* 114, E8184-E8193 (2017).

17. A. Fokine, M. Z. Islam, Z. Zhang, V. D. Bowman, V. B. Rao, M. G. Rossmann, Structure of the three N-terminal immunoglobulin domains of the highly immunogenic outer capsid protein from a T4-like bacteriophage. *J. Virol.* 85, 8141-8148 (2011).

18. C. Summerford, R. J. Samulski, Membrane-associated heparan sulfate proteoglycan is a receptor for adeno-associated virus type 2 virions. *J. Virol.* 72, 1438-1445 (1998).

19. G. A. Farr, L. G. Zhang, P. Tattersall, Parvoviral virions deploy a capsid-tethered lipolytic enzyme to breach the endosomal membrane during cell entry. *Proc. Natl. Acad. Sci.* 102, 17148-17153 (2005).

20. P. J. Schatz, Use of peptide libraries to map the substrate specificity of a peptide-modifying enzyme: a 13 residue consensus peptide specifies biotinylation in *Escherichia coli. Biotechnology* 11, 1138-1143 (1993).

21. D. Grimm, J. S. Lee, L. Wang, T. Desai, B. Akache, T. A. Storm, M. A. Kay, In vitro and in vivo gene therapy vector evolution via multispecies interbreeding and retargeting of adeno-associated viruses. *J. Virol.* 82, 5887-5911 (2008).

22. G. S. Arnold, A. K. Sasser, M. D. Stachler, J. S. Bartlett, Metabolic biotinylation provides a unique platform for the purification and targeting of multiple AAV vector serotypes. *Mol.* 753 *Ther.* 14, 97-106 (2006).

23. V. B. Rao, M. Feiss, Mechanisms of DNA Packaging by Large Double-Stranded DNA 755 Viruses. *Annu. Rev. Virol.* 2, 351-378 (2015).

24. P. O. Seglen, B. Grinde, A. E. Solheim, Inhibition of the lysosomal pathway of protein degradation in isolated rat hepatocytes by ammonia, methylamine, chloroquine and leupeptin. *Eur. J. Biochem.* 95, 215-225 (1979).

25. Z. Zadori, J. Szelei, M. C. Lacoste, Y. Li, S. Gariepy, P. Raymond, M. Allaire, I. R. Nabi, P. Tijssen, A viral phospholipase A2 is required for parvovirus infectivity. *Dev. Cell.* 1, 291-302 (2001).

26. M. Penaud-Budloo, C. Le Guiner, A. Nowrouzi, A. Toromanoff, Y. Cherel, P. Chenuaud, M. Schmidt, C. von Kalle, F. Rolling, P. Moullier, R. O. Snyder, Adeno-associated virus vector genomes persist as episomal chromatin in primate muscle. *J. Virol.* 82, 7875-7885 (2008).

27. K. T. Gause, A. K. Wheatley, J. Cui, Y. Yan, S. J. Kent, F. Caruso, Immunological Principles Guiding the Rational Design of Particles for Vaccine Delivery. *ACS Nano* 11, 54-68 (2017).

28. J. J. Barr, R. Auro, M. Furlan, K. L. Whiteson, M. L. Erb, J. Pogliano, A. Stotland, R. Wolkowicz, A. S. Cutting, K. S. Doran, P. Salamon, M. Youle, F. Rohwer, Bacteriophage adhering to mucus provide a non-host-derived immunity. *Proc. Natl. Acad. Sci.* 110, 10771-10776 (2013).

29. M. A. Liu, Immunologic basis of vaccine vectors. *Immunity* 33, 504-515 (2010).

30. T. R. Flotte, S. Lu, DNA Vaccination in 2018: An Update. *Hum. Gene Ther.* 29, 963-965 (2018).

31. A. Impagliazzo, F. Milder, H. Kuipers, M. V. Wagner, X. Zhu, R. M. Hoffman, R. van Meersbergen, J. Huizingh, P. Wanningen, J. Verspuij, M. de Man, Z. Ding, A. Apetri, B. Kukrer, E. Sneekes-Vriese, D. Tomkiewicz, N. S. Laursen, P. S. Lee, A. Zakrzewska, L. Dekking, J. Tolboom, L. Tettero, S. van Meerten, W. Yu, W. Koudstaal, J. Goudsmit, A. B. Ward, W. Meijberg, I. A. Wilson, K. Radosevic, A stable trimeric influenza hemagglutinin stem as a broadly protective immunogen. *Science* 349, 1301-1306 (2015).

32. P. Tao, J. Zhu, M. Mahalingam, H. Batra, V. B. Rao, Bacteriophage T4 nanoparticles for vaccine delivery against infectious diseases. *Adv. Drug Deliv. Rev.* (2018). DOI10.1016/j.addr.2018.06.025

33. D. Breitfeld, L. Ohl, E. Kremmer, J. Ellwart, F. Sallusto, M. Lipp, R. Forster, Follicular B helper T cells express CXC chemokine receptor 5, localize to B cell follicles, and support immunoglobulin production. *J. Exp. Med.* 192, 1545-1552 (2000).

34. C. Havenar-Daughton, M. Lindqvist, A. Heit, J. E. Wu, S. M. Reiss, K. Kendric, S. Belanger, S. P. Kasturi, E. Landais, R. S. Akondy, H. M. McGuire, M. Bothwell, P. A. Vagefi, E. Scully, I. P. C. P. Investigators, G. D. Tomaras, M. M. Davis, P. Poignard, R. Ahmed, B. D. Walker, B. Pulendran, M. J. McElrath, D. E. Kaufmann, S. Crotty, CXCL13 is a plasma biomarker of germinal center activity. *Proc. Natl. Acad. Sci.* 113, 2702-2707 (2016).

35. J. J. Moon, B. Huang, D. J. Irvine, Engineering nano- and microparticles to tune immunity. *Adv. Mater.* 24, 3724-3746 (2012).

36. A. Iwasaki, R. Medzhitov, Toll-like receptor control of the adaptive immune responses. *Nat. Immunol.* 5, 987-995 (2004).

37. K. Schwarz, T. Storni, V. Manolova, A. Didierlaurent, J. C. Sirard, P. Rothlisberger, M. F. Bachmann, Role of Toll-like receptors in costimulating cytotoxic T cell responses. *Eur. J. Immunol.* 33, 1465-1470 (2003).

38. P. R. Johnson, B. C. Schnepp, M. J. Connell, D. Rohne, S. Robinson, G. R. Krivulka, C. I. Lord, R. Zinn, D. C. Montefiori, N. L. Letvin, K. R. Clark, Novel adeno- 39. R. Ni, J. Zhou, N. Hossain, Y. Chau, Virus-inspired nucleic acid delivery system: Linking virus and viral mimicry. *Adv. Drug Deliv. Rev.* 106, 3-26 (2016).
40. P. Tao, M. Mahalingam, J. Zhu, M. Moayeri, M. L. Kirtley, E. C. Fitts, J. A. Andersson, W. S. Lawrence, S. H. Leppla, A. K. Chopra, V. B. Rao, A Bivalent Anthrax-Plague Vaccine That Can Protect against Two Tier-1 Bioterror Pathogens, *Bacillus anthracis* and *Yersinia pestis*. *Front. Immunol.* 8, 687 (2017).

All documents, patents, journal articles and other materials cited in the present application are incorporated herein by reference.

While the present invention has been disclosed with references to certain embodiments, numerous modifications, alterations, and changes to the described embodiments are possible without departing from the sphere and scope of the present invention, as defined in the appended claims. Accordingly, it is intended that the present invention is not limited to the described embodiments, but that it has the full scope defined by the language of the following claims, and equivalents thereof.

What is claimed is:

1. A product comprising:
    a first viral vector;
    one or more double stranded DNA molecules packaged in the first viral vector;
    a second viral vector;
    one or more nucleic acid molecules comprising single stranded DNA, double stranded DNA or RNA packaged in the second viral vector; and
    a cross-bridge connecting the second viral vector to the first viral vector;
    wherein the first viral vector is a prokaryotic viral vector; and
    wherein the second viral vector is a eukaryotic viral vector.

2. The product of claim 1, wherein when administered to a biological specimen, an immune response is induced in the biological specimen.

3. A product comprising:
    a first viral vector;
    one or more proteins displayed on the surface of the first viral vector
    a second viral vector; and
    a cross-bridge connecting the second viral vector to the first viral vector;
    wherein the first viral vector is a prokaryotic viral vector;
    wherein the second viral vector is a eukaryotic viral vector; and
    wherein the product, when exposed to cells of a biological specimen, delivers proteins into the cells of the biological specimen.

4. A method of treating a biological specimen, the method comprising:
    administering to the biological specimen a first viral vector;
    a second viral vector; and
    a cross-bridge connecting the second viral vector to the first viral vector;
    wherein the first viral vector is a prokaryotic viral vector;
    wherein the second viral vector is a eukaryotic viral vector; and
    wherein the route of administration is selected from the group consisting of: mixing, orally ingesting, by inhalation, subcutaneous migration, intramuscular injection, intravenous injection, transdermal migration, intranasal inhalation, rectal insertion, ocular, topical migration, sublingual, or buccal.

* * * * *